(12) United States Patent
Cronin et al.

(10) Patent No.: US 10,641,547 B2
(45) Date of Patent: May 5, 2020

(54) POD-BASED SMOOTHIE MAKER

(71) Applicant: Jooster IP AG, Bielbenken (CH)

(72) Inventors: John Cronin, Bonita Springs, FL (US);
Joseph George Bodkin, South Burlington, VT (US); Seth Melvin Cronin, Essex Junction, VT (US); Steven Matthew Philbin, Livermore, CA (US); Dylan Jonathan Wilson, Sarasota, FL (US); Michael Glynn D'Andrea, Burlington, VT (US)

(73) Assignee: VEJO IP AG, Bielbenken BL (CH)

( * ) Notice: Subject to any disclaimer, the term of this patent is extended or adjusted under 35 U.S.C. 154(b) by 0 days.

(21) Appl. No.: 16/414,580

(22) Filed: May 16, 2019

(65) Prior Publication Data

US 2019/0339006 A1    Nov. 7, 2019

Related U.S. Application Data

(63) Continuation-in-part of application No. 16/105,641, filed on Aug. 20, 2018, now abandoned, which is a
(Continued)

(51) Int. Cl.
*F25D 29/00* (2006.01)
*B65D 25/08* (2006.01)
(Continued)

(52) U.S. Cl.
CPC ............ *F25D 29/00* (2013.01); *A23L 2/52* (2013.01); *A47J 31/401* (2013.01); *A47J 31/407* (2013.01);
(Continued)

(58) Field of Classification Search
CPC ...... G07F 13/065; A23G 9/42; G06F 19/3475
See application file for complete search history.

(56) References Cited

U.S. PATENT DOCUMENTS 4,362,033 A   12/1982  Young
4,487,509 A   12/1984  Boyce
(Continued)

FOREIGN PATENT DOCUMENTS

DE   10 2016 005983      11/2017
EP       2 311 748 A1     4/2011
(Continued)

OTHER PUBLICATIONS

Korean Intellectual Property Office, International Search Report for PCT Application No. PCT/US2017/018512, dated Apr. 26, 2017.
(Continued)

*Primary Examiner* — Timothy R Waggoner
(74) *Attorney, Agent, or Firm* — Social IP Law Group LLP; Nikki M. Dossman

(57) ABSTRACT

A method for designing a smoothie pod includes: receiving input from a user via a user device that communicates with a beverage profile system over a communications network, wherein the input is received via a graphical user interface and includes selections of ingredients to be added to the smoothie pod; determining, via the beverage profile system, that a flavor profile of the smoothie pod that is based on the ingredients selected by the user includes at least one flavor type having a percentage of the flavor profile that is outside of an acceptable threshold percentage range of the flavor profile; and presenting a suggestion via the graphical user interface of one or more additional ingredients to be added to the smoothie pod to modify the percentage of the flavor type to be within the acceptable threshold percentage range of the flavor profile.

12 Claims, 44 Drawing Sheets

Related U.S. Application Data continuation of application No. PCT/US2017/018512, filed on Feb. 17, 2017, said application No. 16/414,580 is a continuation-in-part of application No. 16/105,681, filed on Aug. 20, 2018, now Pat. No. 10,464,798, which is a continuation of application No. PCT/US2017/018501, filed on Feb. 17, 2017, said application No. 16/414,580 is a continuation-in-part of application No. 16/105,709, filed on Aug. 20, 2018, which is a continuation of application No. PCT/US2017/018494, filed on Feb. 17, 2017, said application No. 16/414,580 is a continuation-in-part of application No. 16/105,692, filed on Aug. 20, 2018, now Pat. No. 10,336,598, which is a continuation of application No. PCT/US2017/018463, filed on Feb. 17, 2017.

(60) Provisional application No. 62/297,711, filed on Feb. 19, 2016, provisional application No. 62/297,716, filed on Feb. 19, 2016, provisional application No. 62/297,632, filed on Feb. 19, 2016, provisional application No. 62/297,644, filed on Feb. 19, 2016, provisional application No. 62/297,009, filed on Feb. 18, 2016, provisional application No. 62/296,814, filed on Feb. 18, 2016, provisional application No. 62/296,851, filed on Feb. 18, 2016, provisional application No. 62/296,844, filed on Feb. 18, 2016.

(51) Int. Cl.

| | | |
|---|---|---|
| *B65D 51/28* | (2006.01) | |
| *A47J 31/40* | (2006.01) | |
| *A61B 5/11* | (2006.01) | |
| *A61B 5/00* | (2006.01) | |
| *G06F 3/0482* | (2013.01) | |
| *A23L 2/52* | (2006.01) | |
| *G07F 13/06* | (2006.01) | |
| *A47J 31/00* | (2006.01) | |
| *A47J 31/44* | (2006.01) | |
| *A47J 31/52* | (2006.01) | |
| *A63B 24/00* | (2006.01) | |

(52) U.S. Cl.
CPC .......... *A61B 5/1118* (2013.01); *A61B 5/4815* (2013.01); *B65D 25/08* (2013.01); *B65D 51/2807* (2013.01); *G06F 3/0482* (2013.01); *G07F 13/065* (2013.01); *A23V 2002/00* (2013.01); *A47J 31/005* (2013.01); *A47J 31/404* (2013.01); *A47J 31/4407* (2013.01); *A47J 31/521* (2018.08); *A63B 24/0062* (2013.01); *A63B 2024/0065* (2013.01); *A63B 2024/0068* (2013.01); *F25D 2400/361* (2013.01)

(56) References Cited

U.S. PATENT DOCUMENTS

| 5,170,888 | A | 12/1992 | Goncalves |
|---|---|---|---|
| 5,425,579 | A | 6/1995 | Sampson |
| 5,797,313 | A | 8/1998 | Rothley |
| 6,132,078 | A | 10/2000 | Lin |
| 6,962,432 | B2 | 11/2005 | Hofeldt |
| 7,364,348 | B1 | 4/2008 | Jones |
| 7,371,004 | B1 | 5/2008 | Branson, III |
| 7,681,726 | B2 | 3/2010 | O'Donnell |
| 8,403,131 | B2 | 3/2013 | Rovelli |
| 8,851,739 | B2 | 10/2014 | Gonzalez |
| 8,875,751 | B1 | 11/2014 | Nueman, Jr. |
| 9,132,950 | B1 | 9/2015 | Anderson et al. |
| 9,504,974 | B2 | 11/2016 | Ochoa et al. |
| 9,717,264 | B2 | 8/2017 | Herbert |
| 9,775,454 | B2 | 10/2017 | Gonzalez |
| 10,532,866 | B2 | 1/2020 | Teague |
| 2004/0007481 | A1 | 1/2004 | Kiser, Jr. |
| 2005/0133531 | A1 | 6/2005 | Crisp, III |
| 2005/0167296 | A1 | 8/2005 | Shenkar et al. |
| 2005/0284302 | A1 | 12/2005 | Levin |
| 2006/0071000 | A1 | 4/2006 | Weist et al. |
| 2006/0081653 | A1 | 4/2006 | Boland et al. |
| 2006/0198241 | A1 | 9/2006 | Krishnacaitanya et al. |
| 2006/0226035 | A1 | 10/2006 | Smith |
| 2006/0271394 | A1 | 11/2006 | Kelly |
| 2007/0205221 | A1 | 9/2007 | Carpenter |
| 2008/0012701 | A1 | 1/2008 | Kass et al. |
| 2008/0290061 | A1 | 11/2008 | Seelhofer |
| 2009/0105875 | A1* | 4/2009 | Wiles .................... G07F 13/065 700/239 |
| 2010/0025268 | A1 | 2/2010 | Lee |
| 2010/0185322 | A1 | 7/2010 | Bylsma et al. |
| 2011/0089059 | A1 | 4/2011 | Lane |
| 2011/0121306 | A1 | 9/2011 | Stutman |
| 2011/0289044 | A1 | 11/2011 | Harrison |
| 2013/0001111 | A1 | 1/2013 | Knutson |
| 2014/0072679 | A1 | 3/2014 | Balassanian |
| 2014/0114469 | A1 | 4/2014 | Givens et al. |
| 2014/0278229 | A1 | 9/2014 | Hong |
| 2015/0093725 | A1 | 4/2015 | Baarman et al. |
| 2015/0144653 | A1* | 5/2015 | Kline .................... B67D 1/0888 222/1 |
| 2015/0194071 | A1 | 7/2015 | Bennett et al. |
| 2015/0227980 | A1 | 8/2015 | Eberhardt |
| 2015/0239723 | A1 | 8/2015 | Anselmino et al. |
| 2015/0366405 | A1 | 12/2015 | Manchuliantsau |
| 2015/0374175 | A1 | 12/2015 | Gaff |
| 2016/0058245 | A1 | 3/2016 | Smith et al. |
| 2016/0151674 | A1 | 6/2016 | Rauhala |
| 2017/0129665 | A1 | 5/2017 | Rolfes |
| 2017/0193096 | A1* | 7/2017 | Bhatt ................. G09B 19/0092 |
| 2017/0280745 | A1 | 10/2017 | Herbert et al. |
| 2018/0132507 | A1 | 5/2018 | Siegel |
| 2018/0178957 | A1 | 6/2018 | Zalewski |

FOREIGN PATENT DOCUMENTS

| JP | 63-062340 U | 4/1988 |
|---|---|---|
| JP | 2003-317155 A | 11/2003 |
| KR | 10-1006799 B1 | 1/2011 |
| KR | 10-2012-0091677 A | 8/2012 |
| KR | 10-1327549 B1 | 11/2013 |
| KR | 10-2014-0011380 A | 1/2014 |
| KR | 10-2014-0083585 A | 7/2014 |
| WO | 2015-148089 A1 | 10/2015 |
| WO | 2017/143251 A1 | 8/2017 |
| WO | 2017143282 A1 | 8/2017 |
| WO | 2017143292 A1 | 8/2017 |
| WO | 2017200613 A2 | 11/2017 |

OTHER PUBLICATIONS

Korean Intellectual Property Office, Written Opinion of the International Searching Authority for PCT Application No. PCT/US2017/018512, dated Apr. 26, 2017.

Korean Intellectual Property Office, International Search Report for PCT Application No. PCT/US2017/018501, dated Apr. 26, 2017.

Korean Intellectual Property Office, Written Opinion of the International Searching Authority for PCT Application No. PCT/US2017/018501, dated Apr. 26, 2017.

Korean Intellectual Property Office, International Search Report for PCT Application No. PCT/US2017/018463, dated May 31, 2017.

Korean Intellectual Property Office, Written Opinion of the International Searching Authority for PCT Application No. PCT/US2017/018463, dated May 31, 2017.

Korean Intellectual Property Office, International Search Report for PCT Application No. PCT/US2017/018494, dated Dec. 11, 2017.

(56) References Cited

OTHER PUBLICATIONS

Korean Intellectual Property Office, Written Opinion of the International Searching Authority for PCT Application No. PCT/US2017/018494, dated Dec. 11, 2017.
European Patent Office, International Search Report for PCT Application No. PCT PCT/IB2019/056985, dated Dec. 12, 2019. 5 pages.
European Patent Office, Written Opinion for PCT Application No. PCT PCT/IB2019/056985, dated Dec. 12, 2019. 5 pages.

* cited by examiner

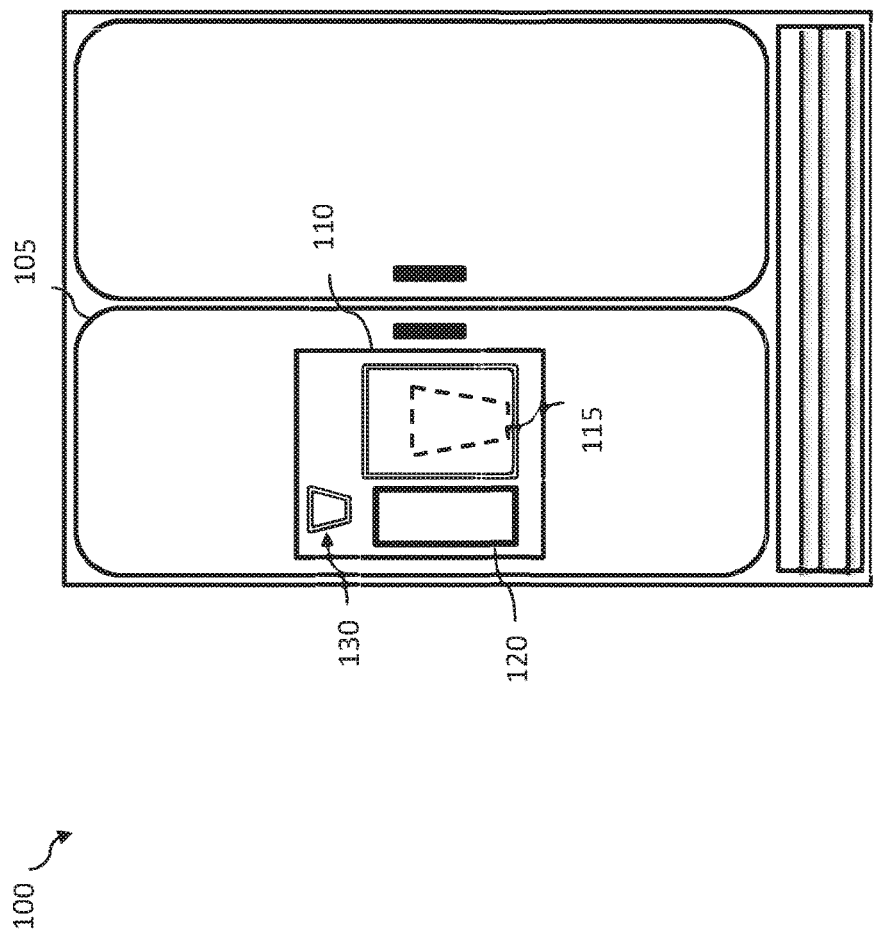

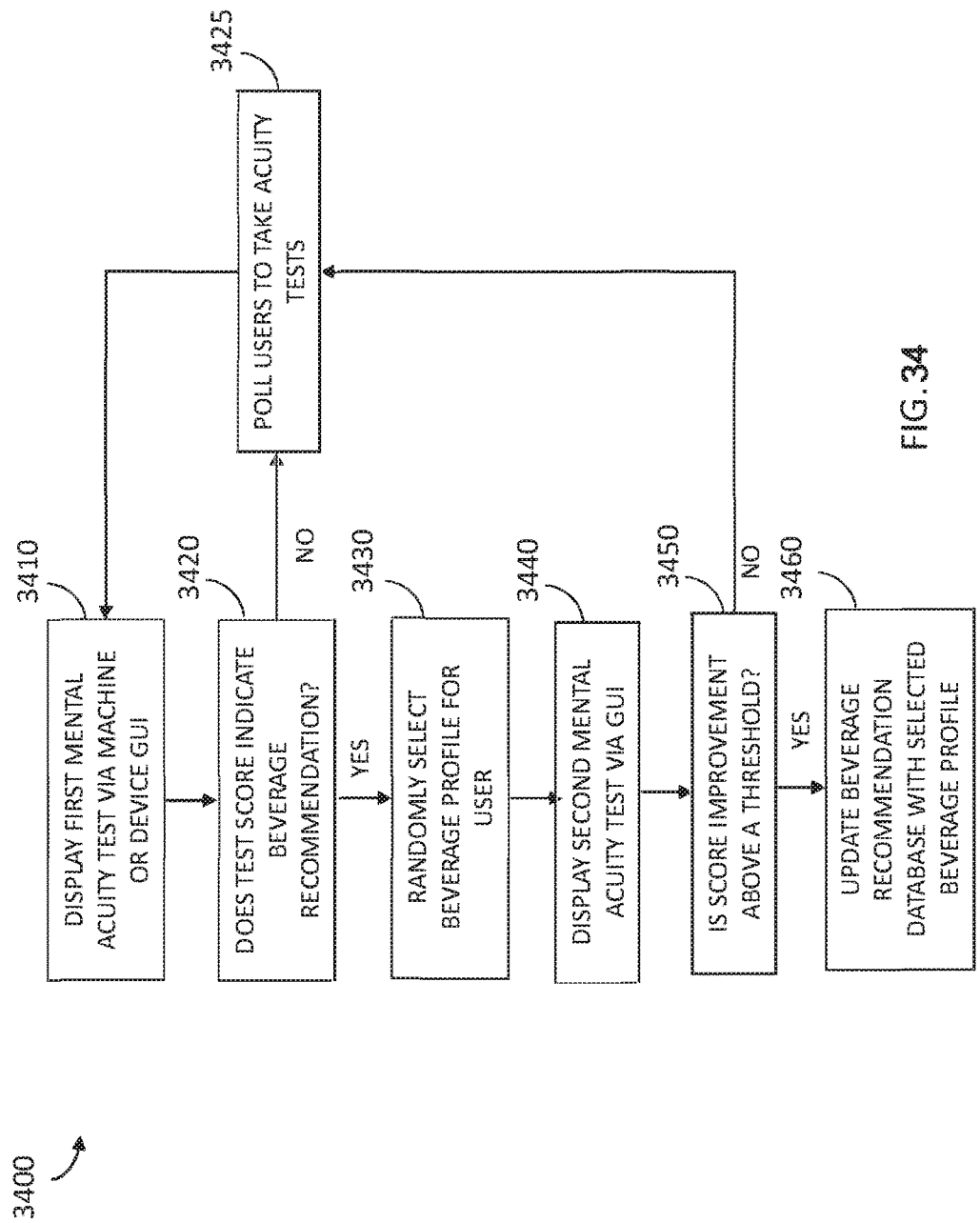

POD-BASED SMOOTHIE MAKER

CROSS-REFERENCE TO RELATED APPLICATION(S)

This application is a continuation-in-part of U.S. patent application Ser. No. 16/105,641, filed on Aug. 20, 2018, entitled "REFRIGERATOR WITH POD-BASED BEVERAGE DISPENSER", which is a bypass continuation of Patent Cooperation Treaty Application No.: PCT/US2017/018512, filed on Feb. 17, 2017, entitled "REFRIGERATOR WITH POD-BASED BEVERAGE DISPENSER", each of which are hereby incorporated by reference in their entirety.

This application is a continuation-in-part of U.S. patent application Ser. No. 16/105,681, filed on Aug. 20, 2018, entitled "RECOMMENDING MODIFICATIONS FOR POD-BASED BEVERAGES", now U.S. Pat. No. 10,464,798, which is a bypass continuation of Patent Cooperation Treaty Application No. PCT/US2017/018501, filed on Feb. 17, 2017, entitled "RECOMMENDING MODIFICATION FOR POD-BASED BEVERAGES", each of which are hereby incorporated by reference in their entirety.

This application is a continuation-in-part of U.S. patent application Ser. No. 16/105,692, filed on Aug. 20, 2018, entitled "PORTABLE, POD-BASED SMOOTHIE MAKER", now U.S. Pat. No. 10,336,598, which is a bypass continuation of Patent Cooperation Treaty Application No.: PCT/US2017/018463, filed on Feb. 17, 2017, entitled "PORTABLE, POD-BASED SMOOTHIE MAKER", each of which are hereby incorporated by reference in their entirety.

This application is a continuation-in-part of U.S. patent application Ser. No. 16/105,709, filed on Aug. 20, 2018, entitled "CUSTOMIZING BEVERAGE PROFILES FOR A USER", which is a bypass continuation of Patent Cooperation Treaty Application No.: PCT/US2017/018494, filed on Feb. 17, 2017, entitled "CUSTOMIZING BEVERAGE PROFILES FOR A USER", each of which are hereby incorporated by reference in their entirety.

Patent Cooperation Treaty Application No.: PCT/US2017/018512, filed on Feb. 17, 2017, entitled "REFRIGERATOR WITH POD-BASED BEVERAGE DISPENSER"; Patent Cooperation Treaty Application No. PCT/US2017/018501, filed on Feb. 17, 2017, entitled "RECOMMENDING MODIFICATION FOR POD-BASED BEVERAGES"; Patent Cooperation Treaty Application No.: PCT/US2017/018463, filed on Feb. 17, 2017, entitled "PORTABLE, POD-BASED SMOOTHIE MAKER"; and Patent Cooperation Treaty Application No.: PCT/US2017/018494, filed on Feb. 17, 2017, entitled "CUSTOMIZING BEVERAGE PROFILES FOR A USER", all claim priority to the following U.S. Provisional Patent Applications: U.S. Provisional Patent Application No. 62/296,814 filed on Feb. 18, 2016, entitled "PROVIDING A USER INTERFACE FOR CUSTOMIZING BEVERAGE PROFILES;" U.S. Provisional Patent Application No. 62/296,844 filed on Feb. 18, 2016, entitled "REFRIGERATOR WITH POD-BASED BEVERAGE DISPENSER;" U.S. Provisional Patent Application No. 62/296,851 filed Feb. 18, 2016, entitled "CUSTOMIZING BEVERAGE PROFILES TO USER SLEEP CYCLES;" U.S. Provisional Patent Application No. 62/297,009 filed Feb. 18, 2016, entitled "RECOMMENDING MODIFICATIONS TO USER-CREATED BEVERAGE PROFILES;" U.S. Provisional Patent Application No. 62/297,644 filed Feb. 19, 2016, entitled "CUSTOMIZING BEVERAGE PROFILES TO USER MENTAL ACUITY;" U.S. Provisional Patent Application No. 62/297,711 filed Feb. 19, 2016, entitled "PORTABLE, POD-BASED SMOOTHIE MAKER;" U.S. Provisional Patent Application No. 62/297,716 filed Feb. 19, 2016, entitled "CUSTOMIZING BEVERAGE PROFILES TO USER WELLNESS PROGRAMS;" and U.S. Provisional Patent Application No. 62/297,632 filed Feb. 19, 2016, entitled "CUSTOMIZING BEVERAGE PROFILES TO USER ACTIVITIES;" each of which are hereby incorporated by reference in their entirety

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

There are numerous retailers, distributors, and companies that attempt to target users with supplements, beverages, and other nutritional foods or drinks. However, most of these products are pre-made and generic to a certain population of users and/or for a certain purpose. For example, companies create sports drinks to assist the performance of a generic user during activities, and retailers sell smoothies that promote certain health benefits to a large population of users.

BRIEF DESCRIPTION OF THE DRAWINGS

Embodiments of the disclosed technology will be described and explained through the use of the accompanying drawings.

FIG. 1A is a diagram illustrating a refrigerator having an integrated pod-based beverage dispenser.

FIG. 34 is a flow diagram illustrating a method for determining a beverage recommendation based on user performance on one or more acuity tests before and after consuming a customized beverage.

DETAILED DESCRIPTION

Refrigerator with Pod-Based Beverage Dispenser

Figure 1B:
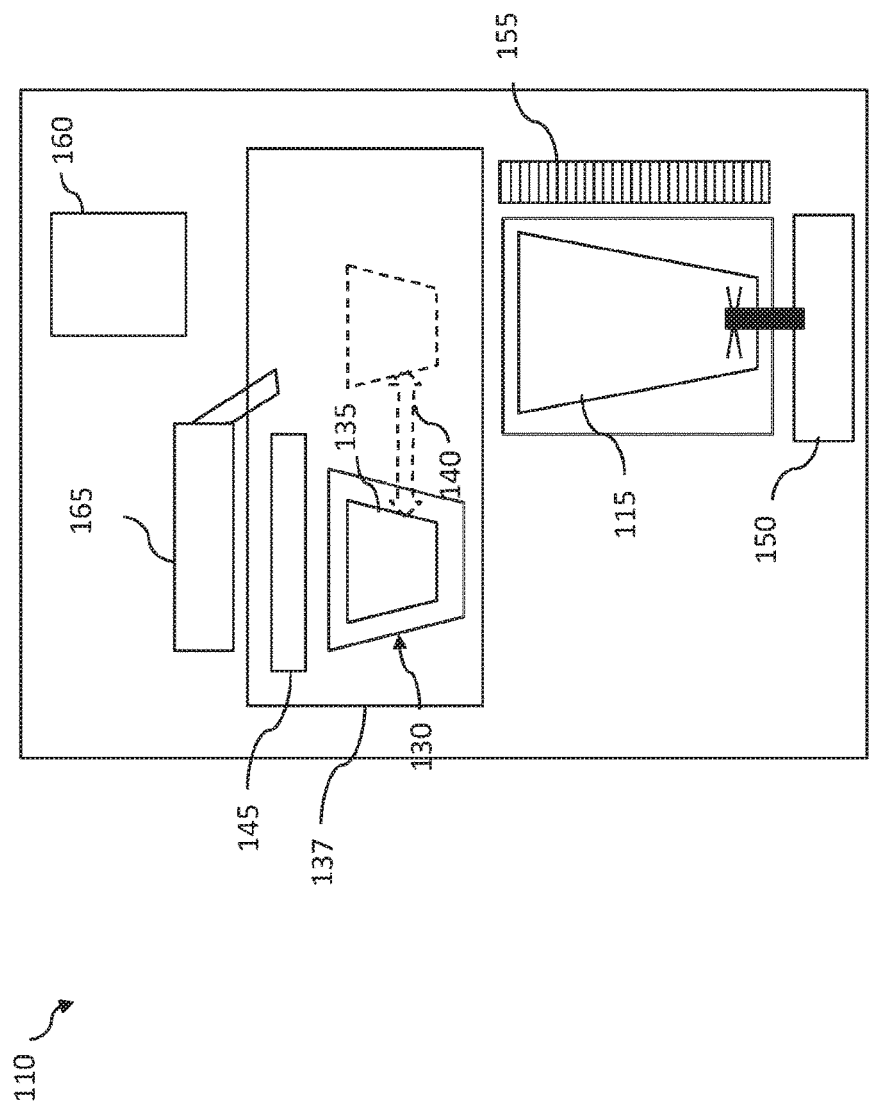
FIG. 1B is a diagram illustrating the beverage dispenser.

Systems and methods for dispensing beverages, such as beverages based on pods of various mixtures (e.g., smoothies based on smoothie pods) are described. The systems and methods described herein provide a refrigerator integrated with a pod-based beverage dispenser, such as a smoothie dispenser, that makes beverages using the contents of a pod or cartridge, as well as water and/or ice from the refrigerator.

For example, a user inputs a selection on a refrigerator GUI presented by an external dispenser unit (e.g., a selection of water, ice, or smoothie). When smoothie is selected, the user selects the size of the smoothie (e.g., 80 z, 120 z, and so on), and inputs a smoothie pod, or cartridge, into the dispenser unit. The device extracts the contents of the pod (or cartridge) and mixes the contents of the pod with water and ice that is fed into the dispenser unit to provide water and ice to the mixture. The dispenser unit then dispenses the mixed smoothie in a cup positioned within or proximate to the dispenser unit.

Therefore, the systems and methods enable a refrigerator to provide pod-based beverages (e.g., smoothies) via dispenser units that often provide water and ice. The systems and methods may control water amounts, ice amounts, and so on, that are associated with requested smoothies, and may control the timing or order or providing ingredients to a smoothie being made, among other benefits.

In some cases, the pod-based dispenser units are part of, or integrated with, a refrigerator. In other cases, the pod-based dispenser units are retrofit or otherwise added to a refrigerator having a conventional dispenser unit (e.g., a unit that provides water and ice), utilizing existing water and ice lines within the refrigerator to provide water and ice when making the pod-based beverages.

The beverage pods, or smoothie pods, may be pods or cartridges containing specific mixtures of ingredients. For example, a pod may include a mixture of various freeze dried fruits (e.g., freeze dried bananas, strawberries, blueberries, mango, and so on), freeze dried vegetables (e.g., kale, spinach, beets, and so on), additive powders (e.g., protein powders, powdered greens), oils, seeds, supplements, flavors, and so on. In some cases, a pod may include a mixture of many different ingredients. In other cases, the pod may include one or more ingredients.

In the following description, for the purposes of explanation, numerous specific details are set forth in order to provide a thorough understanding of embodiments of the present technology. It will be apparent, however, to one skilled in the art that embodiments of the present technology may be practiced without some of these specific details.

The terminology used herein is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

Further details regarding the systems, devices, methods, and routines will be described herein. The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

FIG. 1A is a diagram illustrating a refrigerator 100 having an integrated pod-based beverage dispenser. The refrigerator 100 includes a dispenser unit 110, or smoothie unit, that is part of a door 105 of the refrigerator. The dispenser unit 110 makes and dispenses beverages, such as smoothies based on water, ice, (or, other similar fluids, such as soda water) and the contents of a pod inserted into the dispenser unit 110. The dispenser unit 110 includes a pod opening 130 or pod insertion area via which a smoothie pod may be inserted, and an opening to place a cup 115 within the unit 110. In some cases, the cup may be a cup adapter for a mixer (e.g., a cup of a magic bullet or other mixing device).

The refrigerator also includes a control unit 120, which may receive instructions associated with making a beverage from a cloud-based smoothie network component or server, and/or may control operation of the dispenser unit based on the received instructions or other stored instructions.

FIG. 1B is a diagram illustrating the beverage dispenser or dispenser unit 110. In some embodiments, a smoothie pod 135 or other beverage pod is placed into a pod chamber 137 via the pod opening 130. While the pod 135 is in the pod chamber, a pod opener 145, such as a device (e.g., a cutting device) configured to open the top of the pod 135, opens the pod. A shuttle module 140 moves the pod into a position that allows either the pod 135 to empty its contents proximate to the positioned cup 115 or allows water to flow through the pod 115.

A water module 165, which receives water from the refrigerator 100, and/or an ice module 160, which receives ice from the refrigerator 100, deliver water and/or ice to the cup 115. A mixing device 150, such as a blender or other device configured to mix the contents (e.g., smoothie pod contents, ice, water, and so on), is configured to mix, blend, or otherwise generate a smoothie or other similar beverage within the cup 115.

A level detector 155 monitors the fluid level in the cup 115, and is controlled by the control unit 120, which, as described herein, is configured to coordinate the actions of the various components of the dispenser unit 110. For example, various programs or recipes may be downloaded or programmed to the control unit 120.

The control unit 120, therefore, may utilize instructions stored in one or more databases when controlling operations of the shuttle module 140, the mixing device 150, the ice module 160, and/or the water module 165. For example, the following table, Table 1, represents a set of instructions stored or accessed by the control unit 120 when determining different quantities of water and/or ice to add to a smoothie.

TABLE 1

| Process | | Time (s) | Water Flow | | | | Ice | | | | Mixer | | | Pod | Shuttle | |
|---|---|---|---|---|---|---|---|---|---|---|---|---|---|---|---|---|
| | | | | | | | | Crush | | | | | | | | |
| | | | Low | Med | Hi | On | Crush | Low | Med | High | Low | Med | High | Pod Cut | In | Under Cup |
| 1 | Water Only | User | X | | | | | | | | | | | | | |
| 2 | Water w/Crush Ice Low | User | X | | | | | X | | | | | | | | |
| 3 | Ice cubes only | User | | | X | | | | | | | | | | | |
| 4 | Snow Cone Level | User | | | | | | | X | | | | | | | |
| 5 | Smoothie Program Thin | 2 | X | | | | | | | | | | | | | |
| | | 3 | | | | | | | | | | | X | | | |
| | | 1 | | | | | | X | | | | | | | | |
| | | 2 | | | | | | | | | | | | | | X |
| | | 10 | | X | | | | | | | | X | | | | |
| | | 5 | | | | | | | | | | X | | | X | |
| | | 2 | | | | | | | X | | | | | | | |
| | | 2 | | | X | | | | | | | | | | | |
| | | 10 | | | | | | | | | | | X | | | |
| 5 | Smoothie Program Thick | 2 | X | | | | | | | | | | | | | |
| | | 3 | | | | | | | | | | | X | | | |
| | | 1 | | | | | | X | | | | | | | | |
| | | 2 | | | | | | | | | | | | | | X |
| | | 6 | | X | | | | | | | | X | | | | |
| | | 4 | | | | | | | | | | X | | | X | |
| | | 2 | | | | | | | X | | | | | | | |
| | | 2 | | | X | | | | | | | | | | | |
| | | 6 | | | | | | | | | | | X | | | |

For example, the control unit 120 performs various routines or methods, as instructed, that enable a user to manually control functions of the dispenser unit 110, such as selections of water or ice levels or combinations, and/or may run programs (e.g., "Smoothie Program Thin," "Smoothie Program Thick," and so on) which enable a user to start, after a pod 135 is inserted, to turn on a certain level of water and ice. These routines, as depicted in Table 1, may include positioning the pod 135 via the pod shuttle 140 to flow water at high velocity through the pod 135, shuttling the pod out of the water, continuing to add ice and water at various times, controlling an optional mixer, and so on. Further, the control unit 120 may receive feedback from the fluid detector 155, and adjust various routines based on the feedback.

Figure 2A:
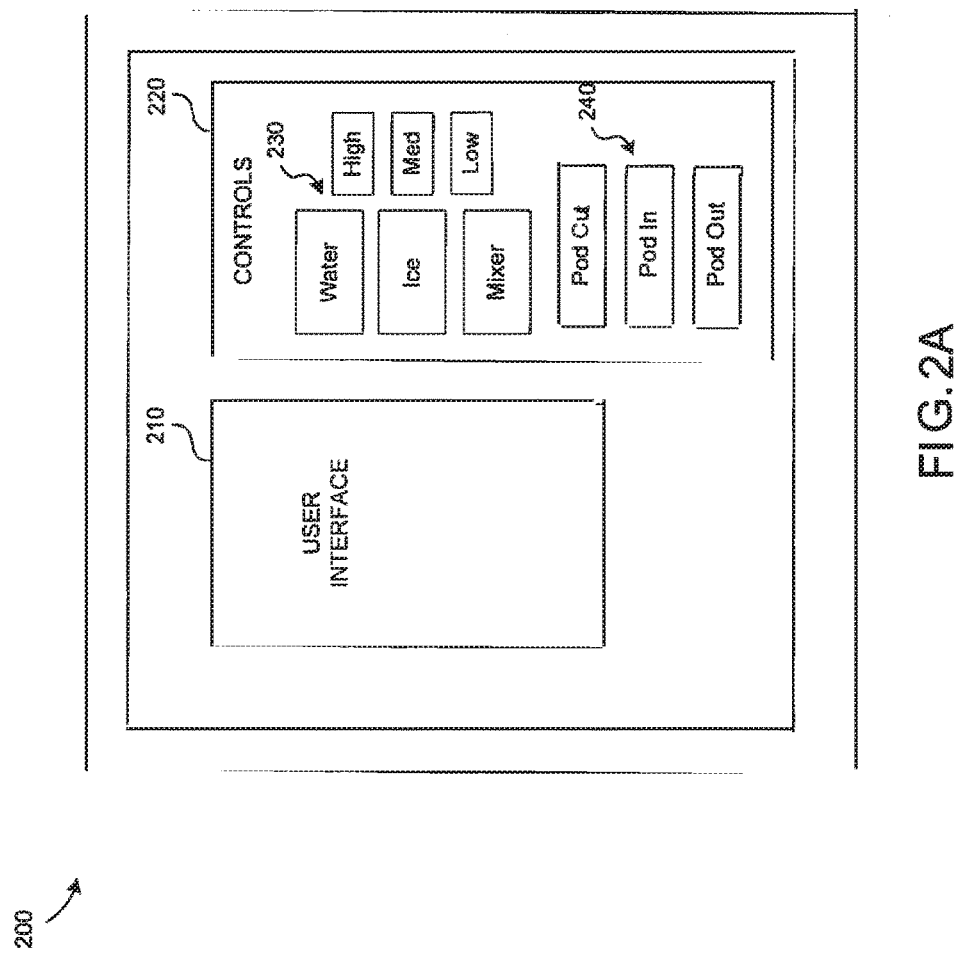
FIG. 2A is a display illustrating a graphical user interface of the refrigerator.

FIG. 2A is a display illustrating a graphical user interface 200 of the refrigerator. The user interface 200, which may be controlled by the control unit 120, includes one or more user interface 210 areas configured to display information to a user (e.g., information about a currently made smoothie or one or more recommended smoothies), as well as various controls 220, such as water, ice, or mixer controls 230, speed controls ("high," "medium," "low," and so on), pod 135 controls 240, and so on.

Figure 2B:
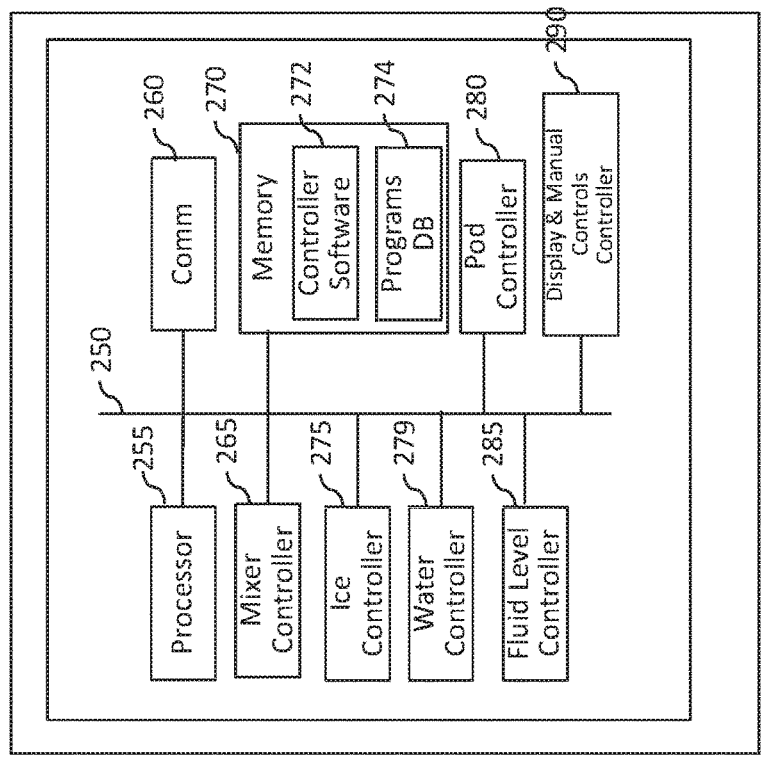
FIG. 2B is a block diagram illustrating components of a control unit of the beverage dispenser.

FIG. 2B is a block diagram illustrating components of the control unit 120 of the dispenser unit 110. The control unit 120 includes a main bus 250 that has a processor 255, and various controllers (mixer controller 265, ice controller 275, water controller 279, fluid level controller 285, pod controller 280, and display and manual controls 290).

Further, the unit 120 may include a communication module 260 (e.g., WiFi, internet, 4G, 3G, Bluetooth, and so on) that is connected to the main bus 250 to receive and transmit information between the unit 120 and other networked devices or systems. Memory 270 is also connected to the bus 250 and stores controller software 272 to run the various programs that are stored in a programs DB (database) 274, such as programs represented by the information in Table 1.

Figure 3:
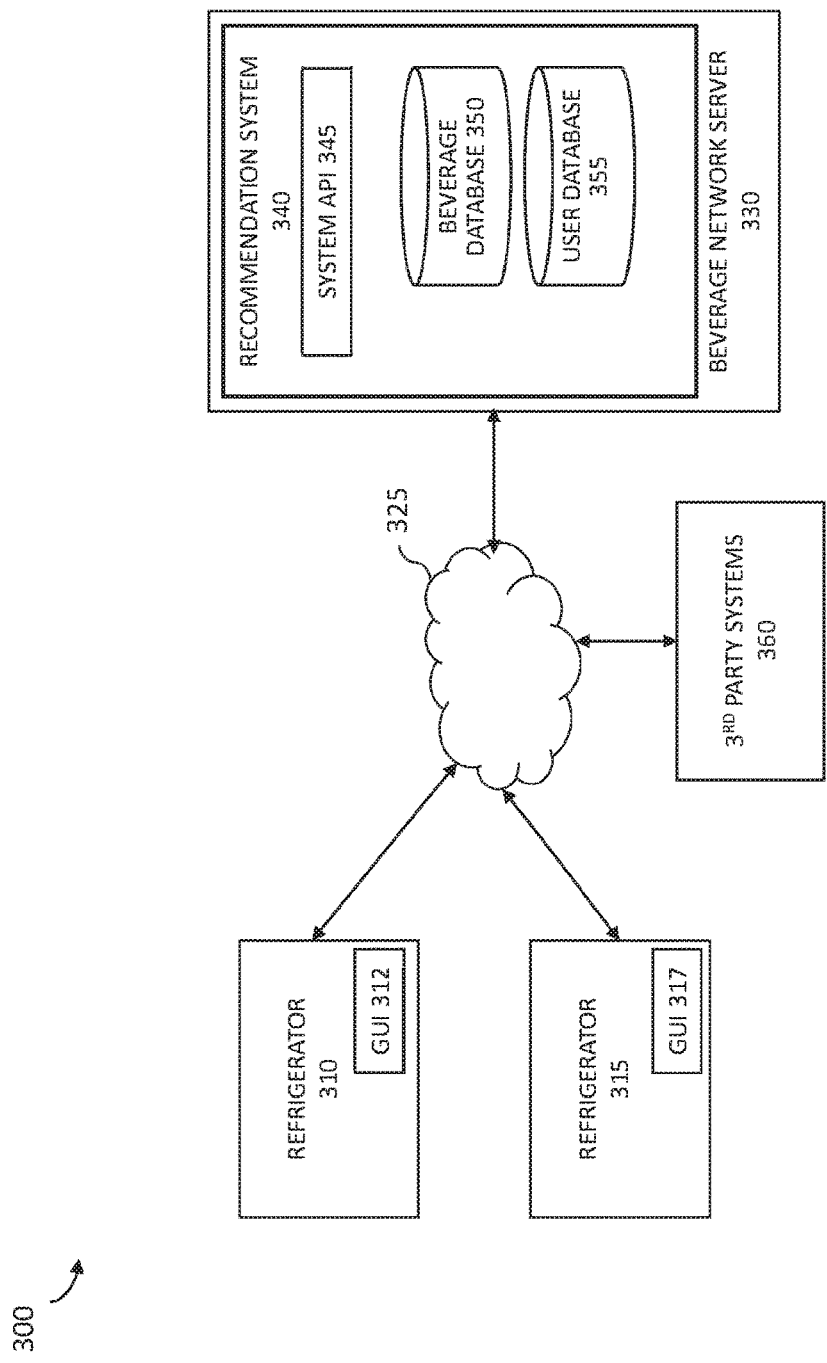
FIG. 3 is a block diagram illustrating a suitable computing environment for providing customized beverages to users via a refrigerator having an integrated pod-based beverage dispenser.

In some embodiments, the dispenser unit 110 receives instructions, recommendations, and other information from various networked or cloud-based sources, such as a cloud-based recommendation system. FIG. 3 is a block diagram illustrating a suitable computing environment 300 for providing customized beverages to users via a refrigerator having an integrated pod-based beverage dispenser.

A recommendation system 340 may communicate with one or more podbased refrigerators 310, 315, each of which having GUIs 312, 317, over a network 325. The recommendation system 340, which may be part of a beverage network server 330, includes and stores information that facilitates determining smoothies and other beverages to make for users based on various characteristics, attributes, or wants for the users.

For example, a beverage database 350 may include many different smoothie programs or beverage profiles for smoothies to be made by the refrigerators 310, 315, and a user database 355 may store information for users associated with the refrigerators 310, 315.

In addition, the recommendation system 340 may publish or make available one or more application programming interfaces (AP's), which are accessed by third party systems 360, such as online health programs, social media services, restaurants, and so on, in order to provide their customers and members with targeted smoothies via the recommendation system 330 and/or refrigerators 310, 315.

FIGS. 1-3 and the discussion herein provide a brief, general description of the suitable computing environment in which the systems can be supported and implemented.

Although not required, aspects of the systems are described in the general context of computer-executable instructions, such as routines executed by a general-purpose computer, e.g., mobile device, a server computer, or personal computer. Those skilled in the relevant art will appreciate that the system can be practiced with other communications, data processing, or computer system configurations, including: Internet appliances, hand-held devices (including tablet computers and/or personal digital assistants (PDAs)), all manner of cellular or mobile phones, multi-processor systems, microprocessor-based or programmable consumer electronics, set-top boxes, network PCs, mini-computers, mainframe computers, and the like. Indeed, the terms "computer," "host," and "host computer," and "mobile device" and "handset" are generally used interchangeably herein, and refer to any of the above devices and systems, as well as any data processor.

Aspects of the systems can be embodied in a special purpose computing device or data processor that is specifically programmed, configured, or constructed to perform one or more of the computer-executable instructions explained in detail herein. Aspects of the system may also be practiced in distributed computing environments where tasks or modules are performed by remote processing devices, which are linked through a communications network, such as a Local Area Network (LAN), Wide Area Network (WAN), or the Internet. In a distributed computing environment, program modules may be located in both local and remote memory storage devices.

Aspects of the systems may be stored or distributed on computer readable media (e.g., physical and/or tangible non-transitory computer-readable storage media), including magnetically or optically readable computer discs, hard-wired or preprogrammed chips (e.g., EEPROM semiconductor chips), nanotechnology memory, or other data storage media. Indeed, computer implemented instructions, data structures, screen displays, and other data under aspects of the system may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Those skilled in the relevant art will recognize that portions of the system reside on a server computer, while corresponding portions reside on a client computer such as a mobile or portable device, and thus, while certain hardware platforms are described herein, aspects of the system are equally applicable to nodes on a network. In an alternative embodiment, the mobile device or portable device may represent the server portion, while the server may represent the client portion.

Figure 4:
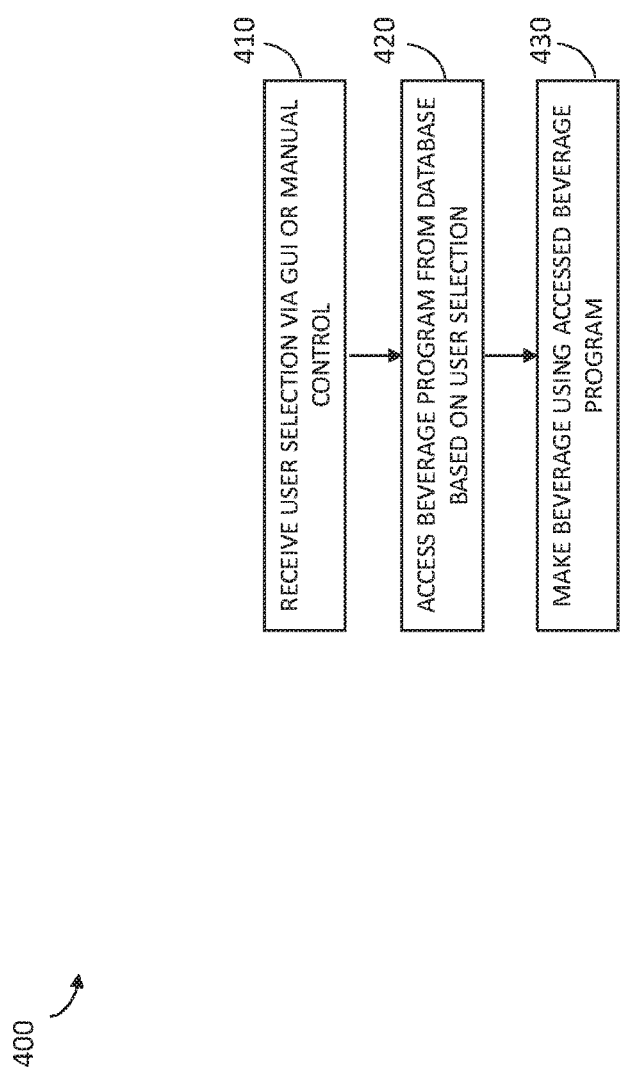
FIG. 4 is a flow diagram illustrating a method for preparing a beverage for a user

As described herein, the refrigerator 100, via the control unit 120, may perform various processes, operations, or methods when preparing smoothies for users. FIG. 4 is a flow diagram illustrating a method 400 for preparing a beverage for a user. Aspects of the method 400 may be performed by the control unit 120 and, accordingly, is described herein merely by way of reference thereto. It will be appreciated that the method 400 may be performed on any suitable hardware.

In operation 410, the control unit 120 receives a user selection via a displayed GUI or manual control to make a smoothie. For example, the user may select one or more recommended smoothies displayed via the user interface 210 of the refrigerator 100.

In operation 420, the control unit 120 accesses a beverage program from a database based on the user selection. For example, the control unit 120 may access the programs database 274 and retrieve a beverage program or other set of instructions associated with the selected smoothie.

In operation 430, the control unit 120 causes the dispenser unit 110 to make the smoothie using the accessed beverage program. For example, the dispenser unit 110 receives a smoothie pod 135 and mixes specified amounts of water and ice to the contents of the pod 135 based on the program.

Figure 5:
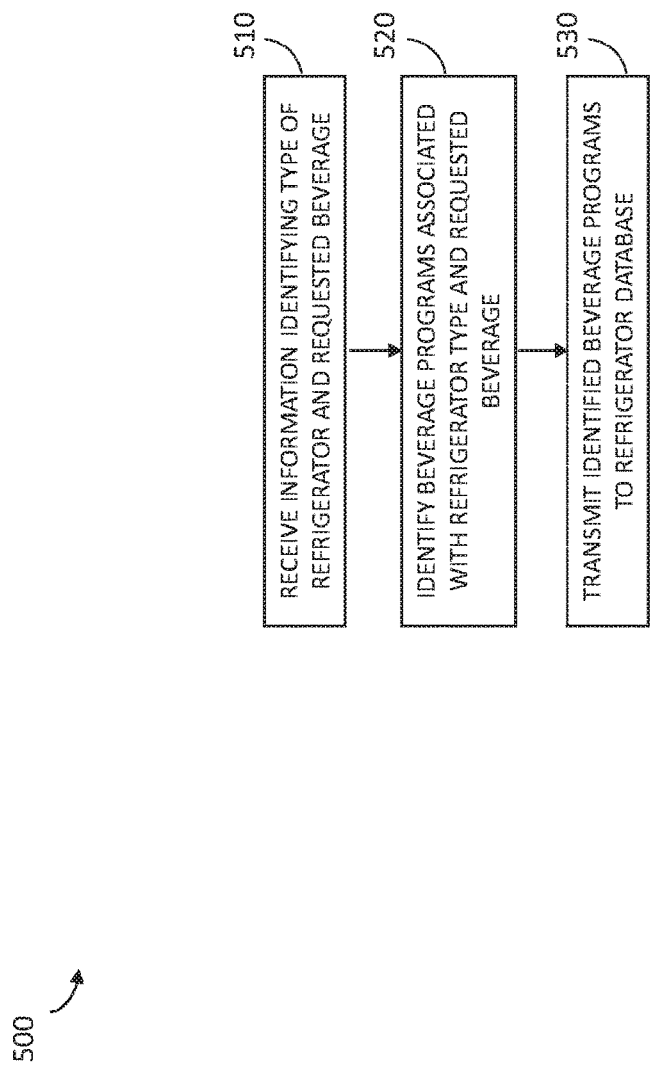
FIG. 5 is a flow diagram illustrating a method for determining a beverage recommendation for a user.

FIG. 5 is a flow diagram illustrating a method 500 for determining a beverage recommendation for a user. Aspects of the method 500 may be performed by the recommendation system 340 and, accordingly, is described herein merely by way of reference thereto. It will be appreciated that the method 500 may be performed on any suitable hardware.

In operation 510, the system 340 receives information identifying a type of refrigerator and a requested beverage (or, user information), from the refrigerator. In operation 520, the system 340 identified one or more beverage programs associated with the refrigerator type (or, identifier) and the requested beverage. For example, the system 340 may access information stored in the beverage database 350 and/or user database 355 in order to determine whether a requesting refrigerator is capable of making a requested smoothie.

In operation 530, the system 340 transmits one or more identified beverage programs to the database 274, which is accessed by the control unit 120 to cause the dispenser unit to make an associated smoothie. Thus, in some embodiments, the refrigerator 100 may request one or more beverage programs from the recommendation system 330, which provides recommendations to an associated user via the user interface 210 of the dispenser unit 110.

Figure 6:
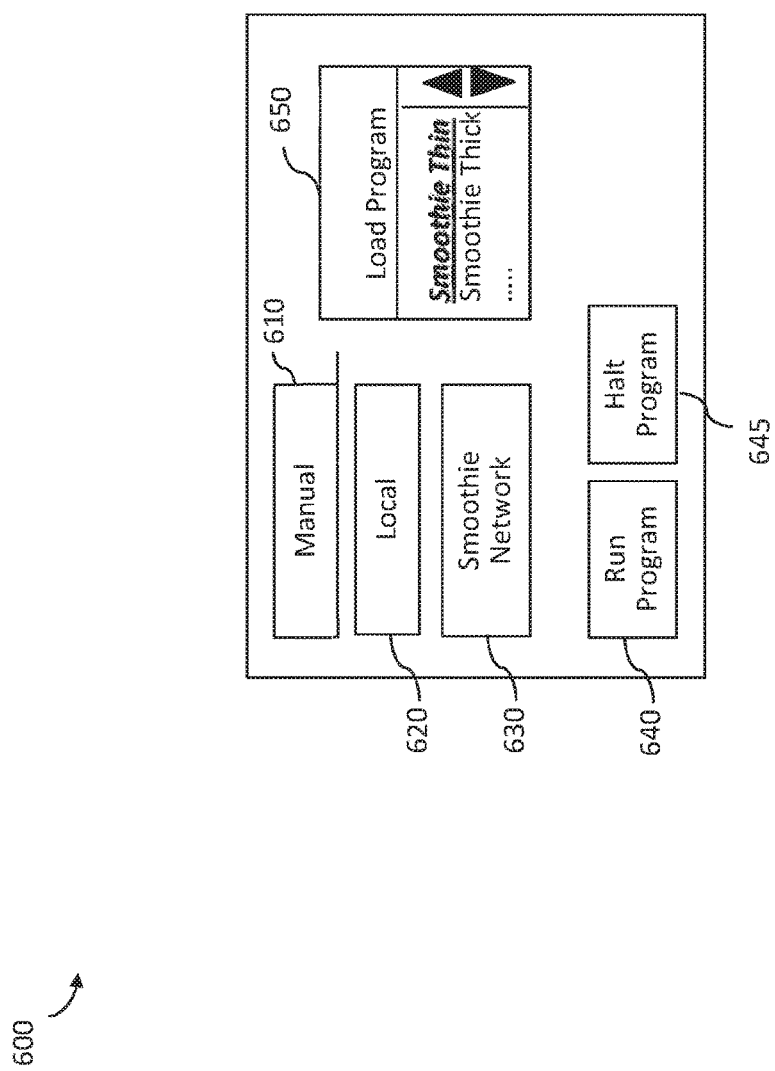
FIG. 6 is a display diagram illustrating a user interface of the refrigerator.

FIG. 6 is a display diagram 600 illustrating a user interface of the refrigerator. The GUI 600 allows manual controls 610 to be selected by a user, and/or allows for a user to load a program 650 (e.g., optionally, using a pod code or recognizing QR codes, or via an NFC reader, and so on). The programs may be selected via an option 620 associated with local memory 620 or via an option 630 associated with the recommendation system 340 ("smoothie network"), In some cases, the user may program the functions (not shown). The program status may also be shown as the program proceeds to make the smoothie. The GUI 600 may also provide options to run programs 640 and/or programs 645, among other user controls.

In some cases, the control unit 120 may automatically detect a smoothie, and may automatically search for the program associated with making the smoothie. Further, once a smoothie is made, the control unit 120 may provide a cleaning program, where the dispenser unit 110 requests a cleaning cup or pod to be inserted, and the dispenser unit 110 performs various functions (running of water and ice) to clean the various components of the unit 110 and/or refrigerator 100.

Thus, in some embodiments, the systems and methods described herein provide a pod-based beverage dispenser, such as via a dispenser unit of a refrigerator. For example, a refrigerator may have a dispenser unit configured to dispense a beverage that includes a pod opening configured to receive a smoothie pod into the dispenser unit, a pod opener configured to open a received smoothie pod, a pod shuttle configured to position the opened smoothie pod within a pod chamber of the dispenser unit, and a pod chamber configured to mix contents extracted from the opened smoothie pod with water or ice supplied to the pod chamber from the refrigerator, and dispense a mixture of the smoothie pod contents and the water or ice into a cup positioned within the dispenser unit.

Recommending Modifications for Pod-Based Beverages

Systems and methods for customizing beverage profiles, such as customizing smoothie pods via input received via web-based portals or interfaces, are described. For example, the systems and methods may provide users with interactive interfaces that facilitate the reception of user input regarding the customization of a beverage, such as the customization of a nutritional or flavor profile of a beverage.

The systems and methods may make beverages (e.g., smoothies or other drinks) and/or order or create smoothie pods (e.g., containers of ingredients used when making a beverage) having the customized beverage profiles. The systems and methods, therefore, may provide the user with a customized smoothie or other beverage that includes ingredients useful in improving, benefiting, or mitigating the user's health, performance, mental state, and/or other characteristics or states, among other benefits.

Figure 7:
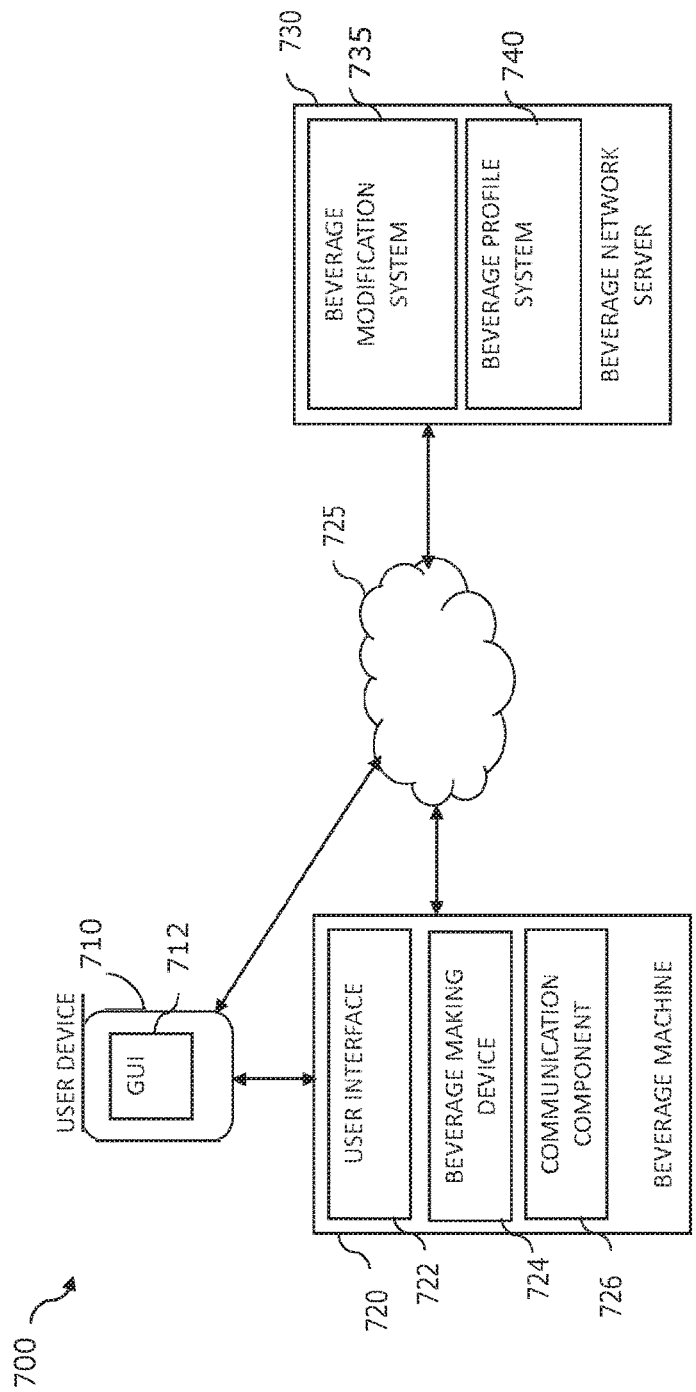
FIG. 7 is a block diagram illustrating a suitable computing environment 700 within which users may design and customize beverages.

As described herein, the systems and methods customize beverage profiles for users based on various aspects or characteristics associated with the users, and create or customize smoothie pods having ingredients that include the customized beverage profiles. FIG. 7 is a block diagram illustrating a suitable computing environment 700 for providing beverages having customized beverage profiles to a user.

The computing environment 700 includes a user device 710 (having a user interface 712). A beverage machine 720, such as a machine, device, or refrigerator configured to create beverages from pods or other ingredients sources, may be directly connected to the user device 710 or may communicate with the user device 710 or other devices, systems, and/or servers over a network 725, such as the Internet.

The beverage machine 720, therefore, may include a communication component 726 that facilitates communicating with various devices over the network 725, a user interface component 722 that renders, displays, and/or presents information to users via a display, such as a graphical user interface (GUI), and/or receives input from users via the display or via various manual controls of the beverage machine 720. The beverage machine 720 also includes a beverage making device 724, such as a blender or other pod-based beverage creating or making devices.

For example, the beverage making device 724 may be configured to extract contents (e.g., ingredients) within a beverage pod, such as a smoothie pod, and mix or combine the extracted contents with various liquids or other mixing substances, such as water, ice, milk, and so on, based on received or stored programs, recipes, and/or instructions. The beverage pods may be pods or cartridges containing specific mixtures of ingredients. For example, a pod may include a mixture of various freeze dried fruits (e.g., freeze dried bananas, strawberries, blueberries, mango, and so on), freeze dried vegetables (e.g., kale, spinach, beets, and so on), additive powders (e.g., protein powders, powdered greens), oils, seeds, supplements, flavors, and so on. In some cases, a pod may include a mixture of many different ingredients. In other cases, the pod may include one or more ingredients.

A beverage network server 730 may support and/or provide a "beverage network" or other cloud-based systems that perform various actions or functions to determine or create beverage profile recommendations for users. For example, the server 730, which may communicate with the beverage machine 720 or the user device 710 over the network 725, may include various different systems configured to access, receive, obtain, or retrieve certain information about or received from a user and generate beverage profiles for beverages targeted or customized for the user.

Example systems, which are discussed in greater detail herein, include a beverage modification system 735 that is configured to determine beverage modification recommendations to users based on requested nutritional profiles for the beverages, and a beverage profile system 740 that is configured to determine beverage modification recommendations to users based on requested flavor profiles for the beverages. The server 730 may also include other recommendation systems described herein.

FIG. 7 and the discussion herein provide a brief, general description of the suitable computing environment 700 in which the system can be supported and implemented. Although not required, aspects of the systems are described in the general context of computer-executable instructions, such as routines executed by a general-purpose computer, e.g., mobile device, a server computer, or personal computer. Those skilled in the relevant art will appreciate that the system can be practiced with other communications, data processing, or computer system configurations, including: Internet appliances, hand-held devices (including tablet computers and/or personal digital assistants (PDAs)), all manner of cellular or mobile phones, multi-processor systems, microprocessor-based or programmable consumer electronics, set-top boxes, network PCs, mini-computers, mainframe computers, and the like. Indeed, the terms "computer," "host," and "host computer," and "mobile device" and "handset" are generally used interchangeably herein, and refer to any of the above devices and systems, as well as any data processor.

Aspects of the systems described herein can be embodied in a special purpose computing device or data processor that is specifically programmed, configured, or constructed to perform one or more of the computer-executable instructions explained in detail herein. Aspects of the system may also be practiced in distributed computing environments where tasks or modules are performed by remote processing devices, which are linked through a communications network, such as a Local Area Network (LAN), Wide Area Network (WAN), or the Internet. In a distributed computing environment, program modules may be located in both local and remote memory storage devices.

As described herein, in some embodiments, the systems and methods provide an interactive, web-based portal, interface (e.g., graphical user interface, or GUI), and/or platform for designing and creating smoothie pods and other beverage pods. Via the interface, the systems facilitate the reception of user input regarding various ingredients and substances, and associated amounts, percentages, or levels (e.g., levels of freeze-dried fruit, supplements, and so on) to be added when customizing smoothie pods for users.

For example, the interface enables a user to add a level of freeze-dried fruit, supplements, and so on (e.g., ingredients for a smoothie pod). The web portal displays the associated health benefits and supplements (e.g., protein, vitamins, and so on) that result, as the ingredients are added. The displayed information enables the user to see the effect of adding supplements to a smoothie pod, and facilitates a user adjusting different aspects of a smoothie for their health and wellness, among other benefits.

Further, the systems may suggest supplements based upon proposed diet, disease state, training regime, and so on, of the user. For example, when the user enters what ingredients/supplements they plan on using, the system recommends an amount of each supplement that can be added without distorting the taste. Thus, the web portal may depict a flavor type and level as ingredients are added, providing users with a visual representation or depiction of the smoothie pod, and the effect of adding items to the customized smoothie pod.

Therefore, the systems described herein may provide various users (e.g., users concerned with nutrition and contents of pre-made pods, users with sensitive pallets or picky flavor preferences, users with special needs/allergies, users with children, and so on), with the ability to control and make customized smoothie pods, utilizing presented interfaces to assist the users with creating their smoothie pods, tuning the flavoring of the smoothie pods, and so on.

As described herein, the user, via the custom beverage GUI of the user device 710 or machine 720, selects parameters for a customized beverage, and the device 710 or machine 720 transfers the parameters to the beverage modification system 735 of the beverage network server 730.

Figure 8:
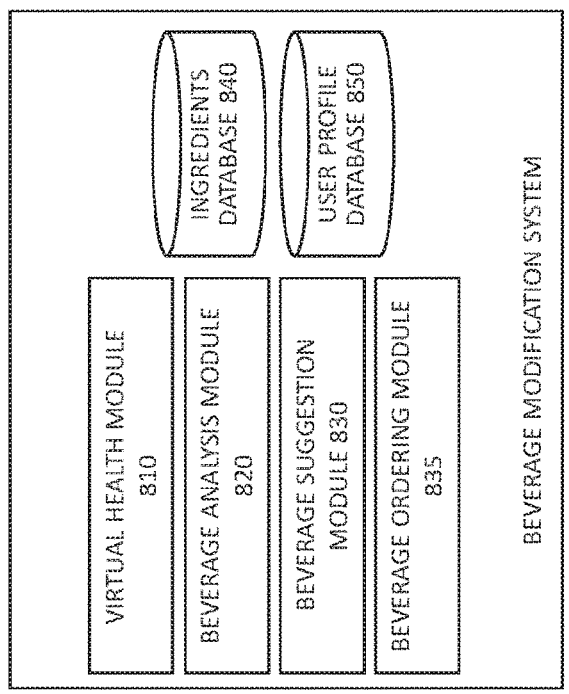
FIG. 8 is a block diagram illustrating components of a beverage modification system.

FIG. 8 is a block diagram illustrating components of the beverage modification system 735. For example, the beverage modification system 735 includes a virtual health module 810 that analyzes the parameters and compares the parameters to information stored in an ingredients database 840, which stores data structures that relate ingredients to their nutritional profiles (e.g., vitamins, calories, and so on). A beverage analysis module 820 may determine, using the comparison of parameters to information in the ingredients database 840, a beverage or nutritional profile for the user customized beverage. A health or user profile database 850 contains data about the nutritional value and health effects of ingredients and/or health information for the user, and provides the system 735 with information associated with the nutritional value and health effects of a beverage, such as the customized beverage.

A beverage suggestion module 830 generates a suggestion or recommendation associated with modifying, adjusting, and/or improving the nutritional profile (or, flavor or other aspects) of the beverage. For example, the beverage suggestion module 830 may identify one or more ingredients, additives, or supplements to add to the customized beverage to reduce or compensate for differences between user goals and the profile of the customized beverage.

Further, the system 735 may include a beverage ordering module 830 that enables the user to order a beverage pod (e.g., smoothie pod) that, when placed in the beverage machine 720, produces the customized beverage (e.g., smoothie) designed by the user (and, optionally, based on suggestions by the system).

Figure 9:
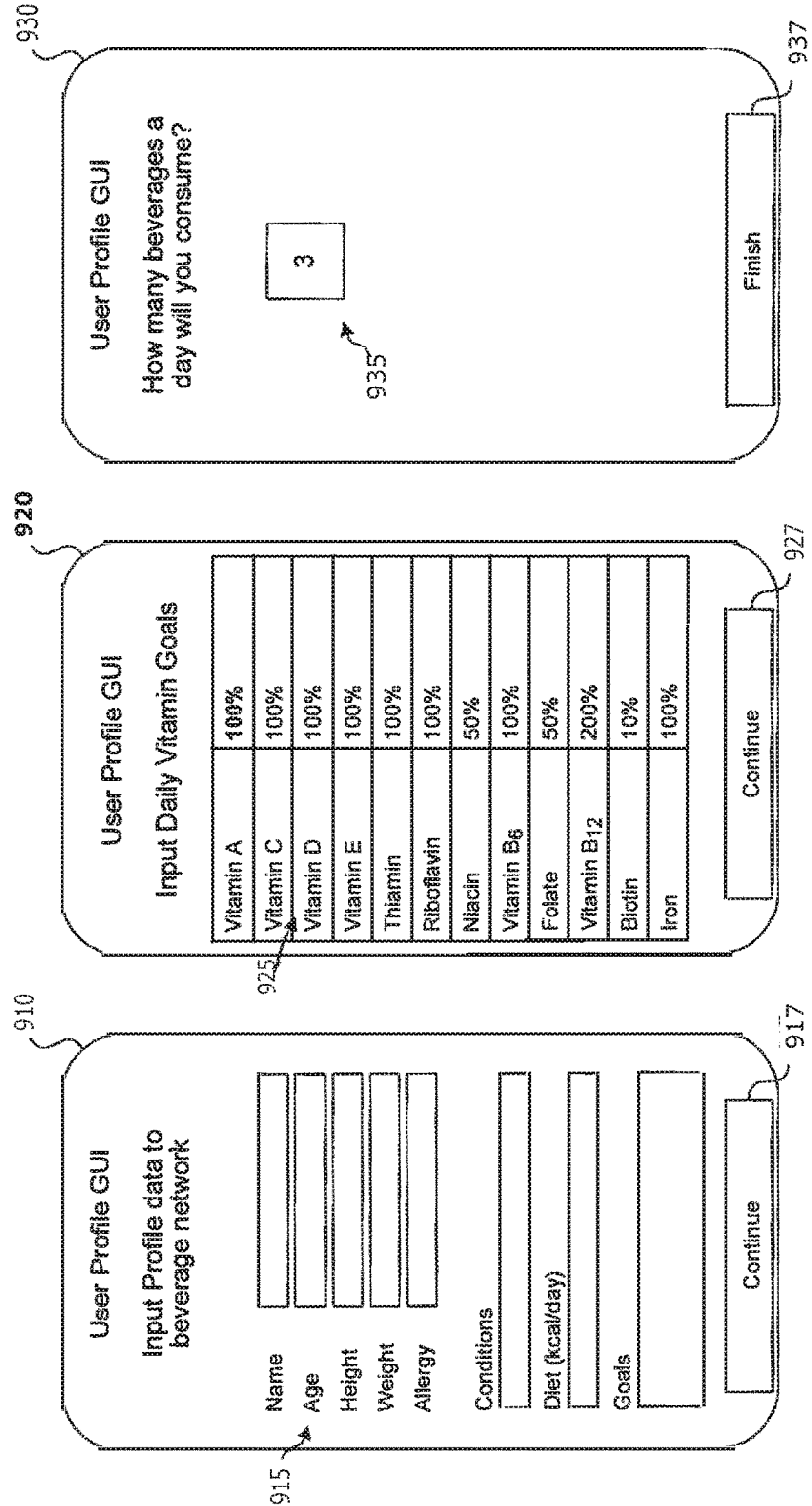
FIGS. 9A-9C are display diagrams illustrating user interfaces for receiving user information.

As described herein, the systems and methods facilitate the customization of beverages for users via various displayed user interfaces. FIGS. 9A-9C are display diagrams illustrating user interfaces for receiving user information.

As shown in FIG. 9A, a user interface 910 facilitates the input of user information 915, such as biographical information, health information, demographic information, vital information, and so on. Once input, the user may select an option 917 to continue, and the system presents a user interface 920, as shown in FIG. 9B.

User interface 920 presents vitamin goal information, and facilitates receiving user input regarding the goal information. For example, the interface 920 may receive input that identifies daily percentage goals for different vitamins 925, caloric intake goals, and so on. Once the goals are provided, the user may select an option 927 to continue, and the system presents a user interface 930, as shown in FIG. 9C.

The user interface 930 includes elements that facilitate receiving input that identifies consumption parameters or goals 935 for the user. For example, the user may provide a number of beverages to be prepared and consumed each day by the user, a total amount of beverages to be consumed, a percentage of total calories to be allotted to the beverages, and so on. Once the information is input, the user may select a finish option 937, which causes the system to analyze the information provided by the user and display information associated with the beverage being customized by the user.

Figure 10:
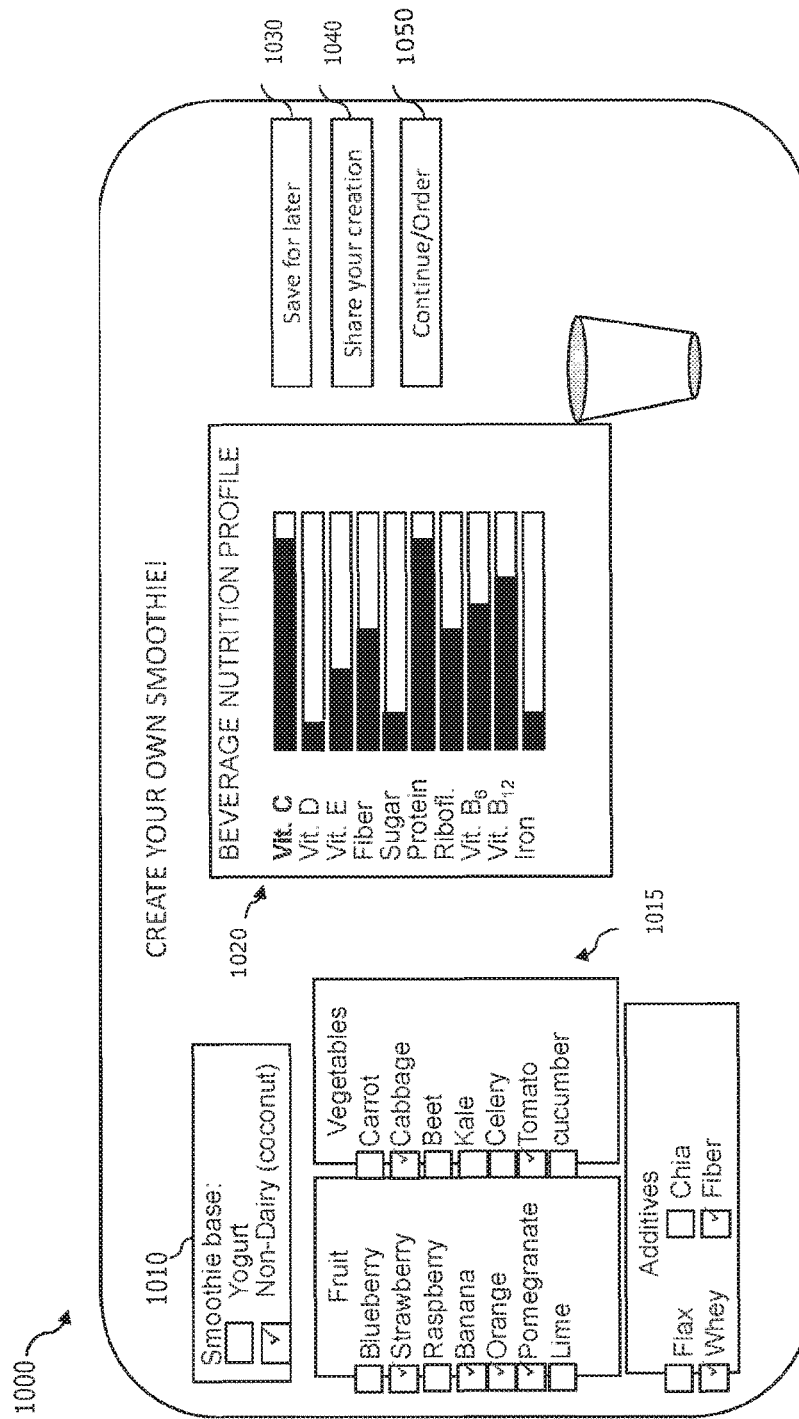
FIG. 10 is display diagram illustrating a user interface for receiving input about a beverage and displaying a nutritional profile for the beverage.

FIG. 10 is display diagram illustrating a user interface 1000 for receiving input about a beverage and displaying a nutritional profile for the beverage. The interface 1000 enables the user to select a base 1010 for the beverage and one or more ingredients or additives 1015 that they would like to be included in their beverage. The interface then presents an expected nutritional profile 1020 for the beverage based on the user's received customization input. The user may then select one or more actions to be performed, such as an option 1030 to save the created beverage, an option 1040 to share information about the beverage with others (e.g., via their social networks), an option 1050 to continue, order, or make the beverage, and so on.

Figure 11C:
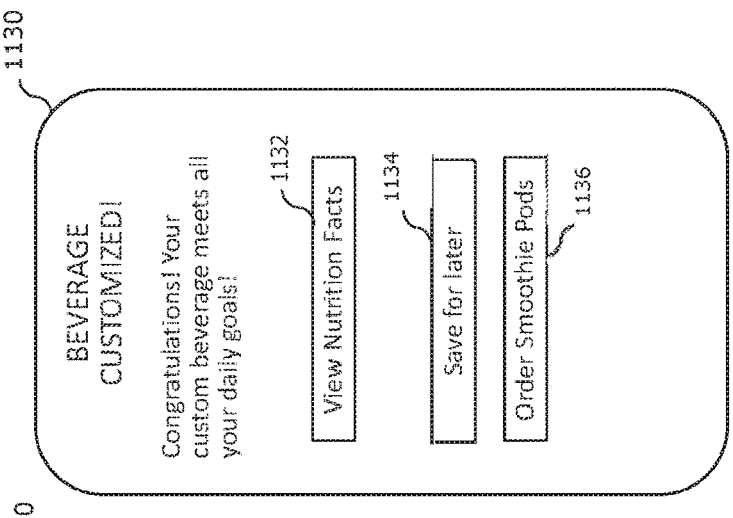
FIGS. 11A-11C are display diagrams illustrating user interfaces for customizing a beverage for a user.
Figure 11B:
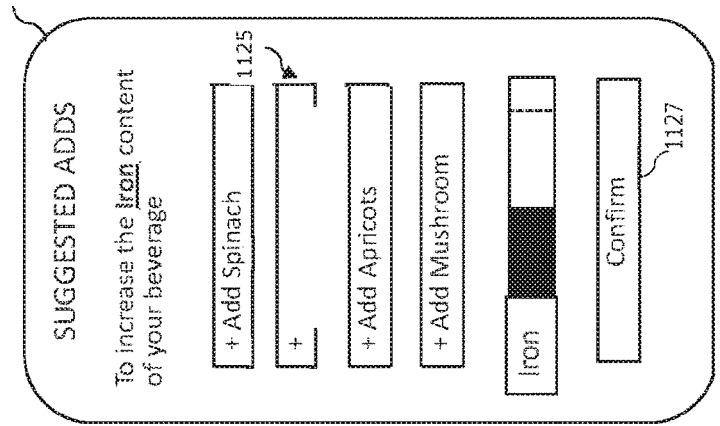
Figure 11A:
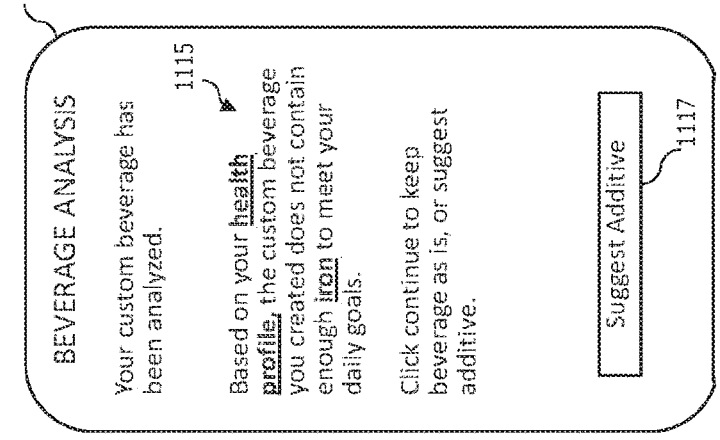

FIGS. 11A-11C are display diagrams illustrating user interfaces for customizing a beverage for a user. As shown in user interface 1110 of FIG. 11A, the system 735 compares the user's health or nutritional goals with the determined nutritional profile of the customized beverage (see FIG. 4), and presents information 1115 that indicates a result of the comparison. For example, as depicted, the system 735 determined that the user's customized beverage does not include a sufficient amount of iron to meet the user's goal, and presents an option 1117 to facilitate a suggestion of an additive to the customized beverage.

When the user selects the option 1117 to present a suggestion of an additive, the system 735 causes user interface 1120, as shown in FIG. 11B, to be displayed. User interface 1120 presents various suggested additives, which, if added to the customized beverage, will add or compensate for the determined nutritional deficiency (e.g., low iron) of the customize beverage. For example, the interface 1120 displays various additive options 1125 that, when selected by the user and requested 1127 to be added, modify the nutritional profile of the customized beverage.

FIG. 11C presents a user interface 1130 that presents results of modifying the customized beverage and information associated with the beverage. For example, the interface 1130 includes options to view the updated nutritional profile 1132 for the beverage, save the beverage 1134 for later, order the beverage 1136, make the beverage (if available), and so on.

Therefore, in some embodiments, the beverage modification system 735 provides various user interfaces to receive input from users, display beverage and/or nutritional profiles for customized beverages, present recommended ingredients or additives, order or make the beverages, and other information or options to be acted upon by users when customizing and obtaining smoothies and other beverages for consumption.

Figure 12:
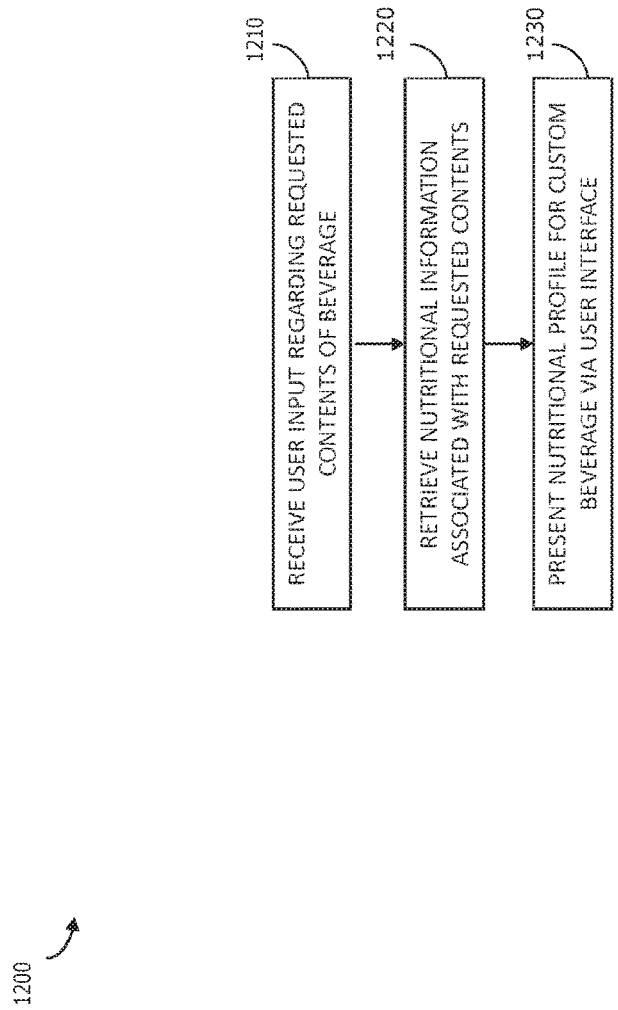
FIG. 12 is a flow diagram illustrating a method for determining a nutritional profile for a customized beverage.

As described herein, the system 735 may perform various processes, operations, or methods when determining profile information for beverages and/or recommending beverages or ingredients to users. FIG. 12 is a flow diagram illustrating a method 1200 for determining a nutritional profile for a customized beverage. Aspects of the method 1200 may be performed by the beverage modification system 735 and, accordingly, is described herein merely by way of reference thereto. It will be appreciated that the method 1200 may be performed on any suitable hardware.

As depicted, the method 1200 may perform operations to determine nutritional information for a user-created beverage. For example, in operation 1210, the system 735 receives user input regarding requested contents of a beverage. In operation 1220, the system 735 retrieves nutritional information (e.g., beverage profiles or nutritional profiles) associated with the request contents. In operation 1230, the system 735, via one or more interfaces, presents (or causes to present) a nutritional profile (see FIG. 4) for the custom beverage.

Figure 13:
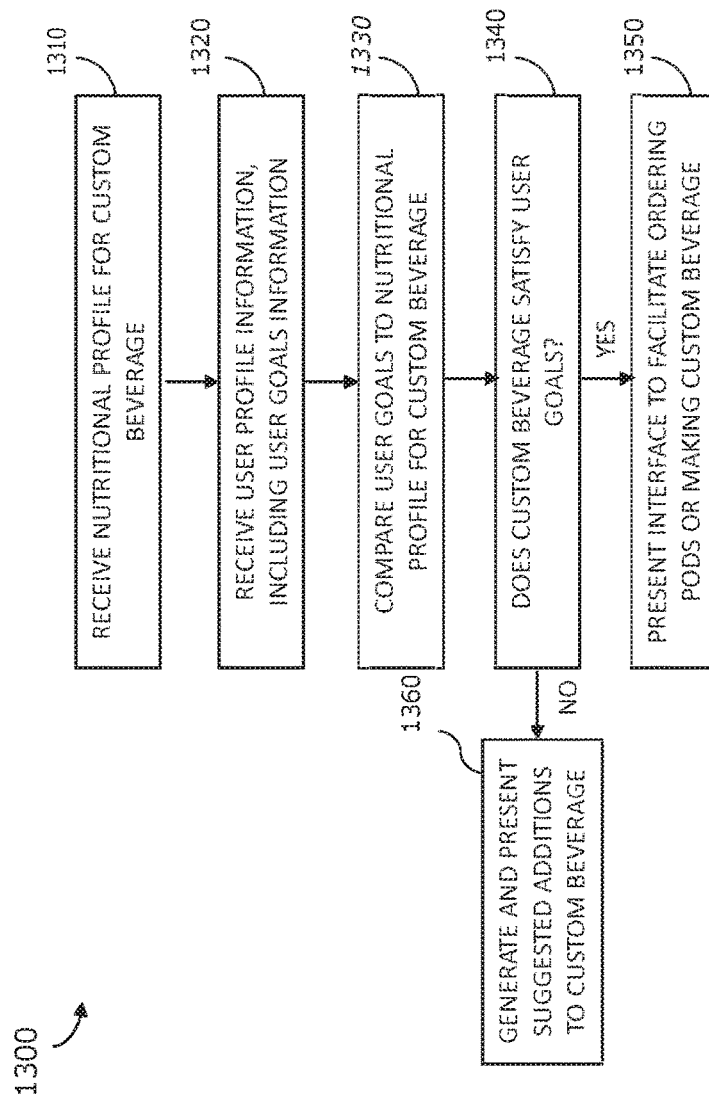
FIG. 13 is a flow diagram illustrating a method for customizing a beverage for a user.

FIG. 13 is a flow diagram illustrating a method 1300 for customizing a beverage for a user. Aspects of the method 1300 may be performed by the beverage modification system 735 and, accordingly, is described herein merely by way of reference thereto. It will be appreciated that the method 1300 may be performed on any suitable hardware. As depicted, the method 1300 may perform operations to determine whether a user-created beverage satisfies the user-provided nutritional goals. For example, in operation 1310, the system 735 receives or accesses a nutritional profile for a customized beverage, and in operation 1320, receives or accesses user profile information, such as user goal information.

In operation 1330, the system 735 compares the user goal information to the nutritional profile for the customized beverage. When the customized beverage has a nutritional profile that matches the user's goals, the method 1300 proceeds to operation 1350, and the system 735 presents an interface to order one or more pods containing ingredients for the customize beverage (or, to make the beverage). When the customized beverage does not have a nutritional profile that matches the user's goals (e.g., is lacking one or more vitamins), the method 1300 proceeds to operation 1360, and the system 735 determines, generates, and/or presents suggested additives or ingredients to add to the customized beverage (see FIG. 11B).

Figure 14:
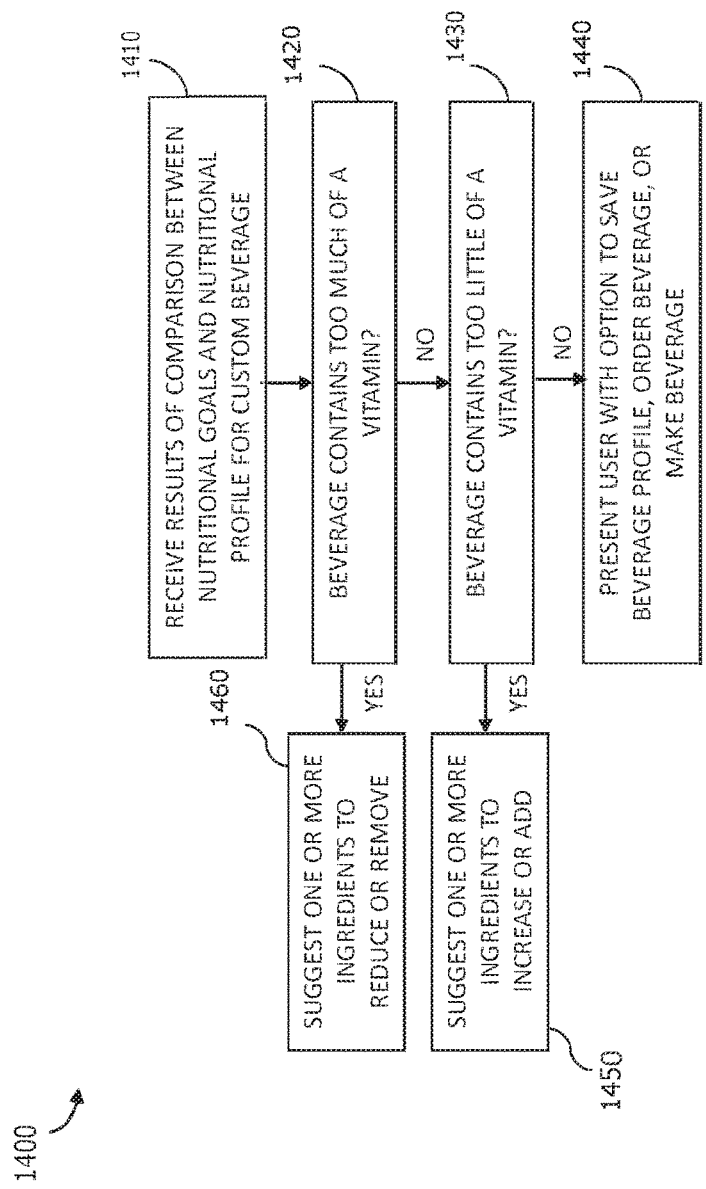
FIG. 14 is a flow diagram illustrating a method for modifying a nutritional profile of a beverage for a user.

FIG. 14 is a flow diagram illustrating a method 1400 for modifying a nutritional profile of a beverage for a user. Aspects of the method 1400 may be performed by the beverage modification system 735 and, accordingly, is described herein merely by way of reference thereto. It will be appreciated that the method 1400 may be performed on any suitable hardware.

As depicted, the method 1400 may perform operations to provide suggestions to modify the user-created beverage. For example, in operation 1410, the system 735 receives results of a comparison between user nutritional goals and a nutritional profile for a customized beverage.

In operation 1420, the system 735 determines whether the nutritional profile includes too much of a vitamin. When the nutritional profile includes too much of a vitamin, the method 1400 proceeds to operation 1430, and the system 735 presents suggestions of one or more ingredients to reduce or remove from the customized beverage.

When the nutritional profile does not include too much of a vitamin, the method 1400 proceeds to operation 1440, and the system 735 determines whether the nutritional profile contains too little of a vitamin. When the nutritional profile includes too little of a vitamin, the method 1400 proceeds to operation 1450, and the system 735 presents suggestions of one or more ingredients to increase or add to the customized beverage. When the nutritional profile does not include too little of a vitamin, the method 1400 proceeds to operation 1460, and presents the user with options to save the beverage, order pods for the beverage, make the beverage, and so on (see FIG. 11C).

Thus, in some embodiments, the beverage modification system 735 may perform a method for designing a smoothie pod or other beverage pod by receiving input from a user via a user device that communicates with the system 735 over a network, where the input is received via a graphical user interface and includes selections of ingredients to be added to the smoothie pod, determining a nutritional profile for the smoothie pod, identifying a nutritional goal for the user, and presenting a suggestion via the graphical user interface of one or more additional ingredients to be added to the smoothie pod to modify the nutritional profile of the smoothie pod based on the nutritional goal for the user.

Examples of Customizing Flavor Profiles of Beverages for Users

As described herein, in some embodiments, the systems and methods provide an interactive, web-based portal, interface (e.g., graphical user interface, or GUI), and/or platform for designing and creating smoothie pods and other beverage pods. Via the interface, the systems facilitate the reception of user input regarding various ingredients and substances, and associated amounts or levels (e.g., levels of freeze-dried fruit, supplements, and so on) to be added when customizing smoothie pods for users.

For example, the web portal may depict a flavor type and level as ingredients are added, providing users with a visual representation or depiction of the smoothie pod, and the effect of adding items (e.g., flavoring additives or ingredients) to the customized smoothie pod. The systems and methods determine flavoring to be added to smoothie pods, such as when the flavor is degraded (or, predicted to be degraded) when too many supplements (or incongruous mixtures) are added to the pods. Further, the systems may determine various flavoring adjustments or modifications, and provide suggestions to users during the creation of the smoothie pods.

Therefore, the systems described herein may provide various users (e.g., users concerned with nutrition and contents of pre-made pods, users with sensitive pallets or picky flavor preferences, users with special needs/allergies, users with children, and so on), with the ability to control and make customized smoothie pods, utilizing presented interfaces to assist the users with creating their smoothie pods, tuning the flavoring of the smoothie pods, and so on.

Figure 15:
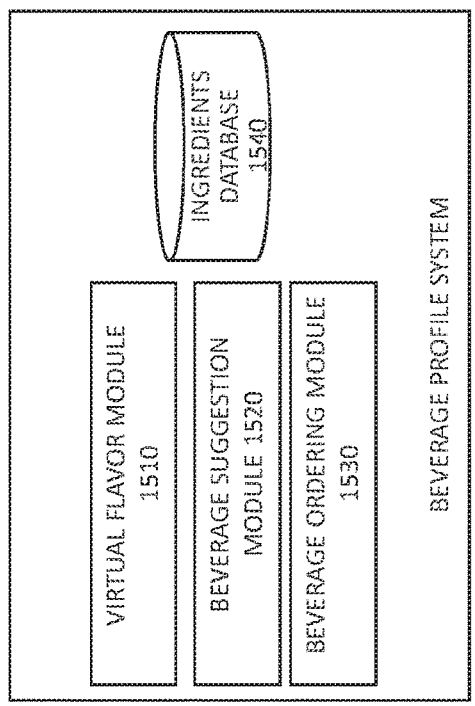
FIG. 15 is a block diagram illustrating components of a beverage profile

FIG. 15 is a block diagram illustrating components of the beverage profile system 740. The beverage profile system 740 includes a virtual flavor module 1510 that analyzes parameters of a user customized beverage, using data from an ingredients database 1540 that is associated with the beverage profile system 740. For example, the virtual flavor module may determine or identify at least one of many flavor profiles: bitter, sweet, sour, savory, salty, anise, and so on, as well as determine whether a flavor profile for the beverage is acceptable or palatable to the user.

Table 2 illustrates example data stored by the ingredients database.

Ingredient Type Bitter Sweet Salty Savory Sour Add to:

TABLE 2

| Ingredient | Type | Bitter | Sweet | Salty | Savory | Sour | Add to: |
| --- | --- | --- | --- | --- | --- | --- | --- |
| Banana | Fruit | 0% | 20% | 0% | 5% | 5% | Sour |
| Kale | Veg | 30% | 0% | 5% | 10% | 0% | Sweet |
| Whey | Additive | 10% | 10% | 5% | 20% | 0% | Salty |

TABLE 2-continued

| Ingredient | Type | Bitter | Sweet | Salty | Savory | Sour | Add to: |
| --- | --- | --- | --- | --- | --- | --- | --- |
| Honey | Additive | 5% | 50% | 0% | 5% | 10% | Bitter |
| Durian | Fruit | 50% | 10% | 5% | 10% | 10% | Sweet |
| Beet | Veg | 20% | 5% | 40% | 15% | 5% | Sweet |

For example, if the virtual flavor module 1510 determines a customized beverage is too sour, it may identify a banana as a recommended ingredient to add to the beverage, using the data of Table 2 that is stored in the ingredients database 1540.

The beverage profile system 740 also includes a beverage suggestion module 1520 that generates a suggestion or recommendation associated with modifying, adjusting, and/or improving the flavor of the beverage. For example, the module 1520 may recommend adding a certain percentage of banana to a beverage having a flavor profile that indicates a sour flavor type is above a certain acceptable percentage of the overall flavor profile.

Further, the system 740 may include a beverage ordering module 1530 that enables the user to order a beverage pod (e.g., smoothie pod) that, when placed in the beverage machine 720, produces the customized beverage (e.g., smoothie) designed by the user (and, optionally, based on suggestions by the system).

As described herein, the systems and methods facilitate the customization of beverages for users via various displayed user interfaces.

Figure 16A:
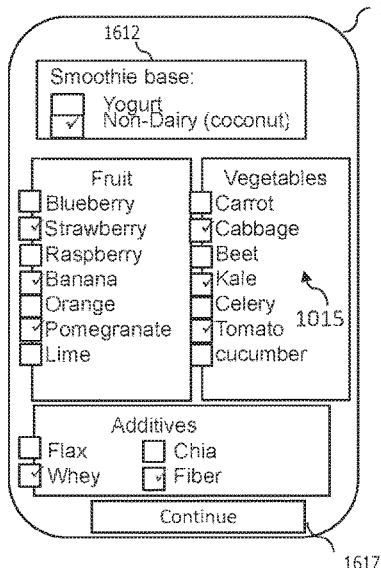
FIGS. 16A-16C are display diagrams illustrating user interfaces that facilitate modifying a flavor profile of a beverage for a user.
Figure 16B:
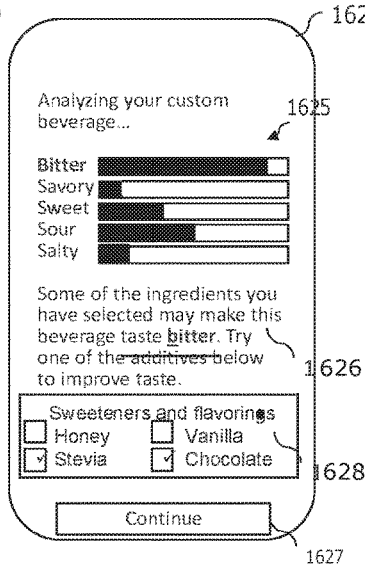
Figure 16C:
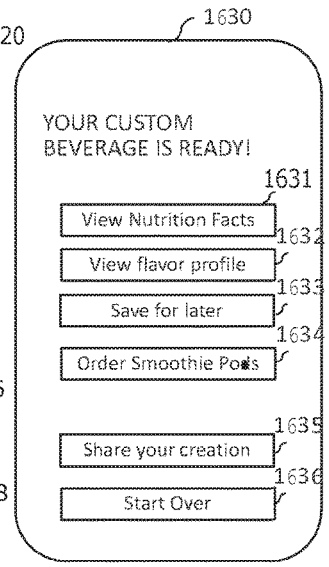

FIGS. 16A-16C are display diagrams illustrating user interfaces that facilitate modifying a flavor profile of a beverage for a user. FIG. 16A presents a user interface 1610 that enables the user to select a base 1612 for the beverage and one or more ingredients or additives 1615 that they would like to be included in their beverage.

Once the user selects an option 1617 to continue, the system 740, via an interface 1620 shown in FIG. 16B, presents an expected flavor profile 1625 for the beverage based on the user's received customization input, information 1626 suggesting an expected flavor for the beverage, and user-selectable options 1628 to add ingredients or additives (e.g., sweeteners, flavoring, and so on) to the beverage.

Once the user selects an option 1627 to continue, the system 740, via an interface 1630, shown in FIG. 16C, presents one or more actions to be performed, such as an option 1631 to view nutritional information for the beverage, an option 1632 to view a modified flavor profile, an option 1633 to save the created beverage, an option 1635 to share information about the beverage with others (e.g., via their social networks), an option 1634 to continue, order, or make the beverage, an option 1636 to create a new customized beverage, and so on.

Therefore, in some embodiments, the beverage profile system 740 provides various user interfaces to receive input from users, display beverage and/or flavor profiles for customized beverages, present recommended ingredients or additives, order or make the beverages, and other information or options to be acted upon by users when customizing and obtaining smoothies and other beverages for consumption.

Figure 17:
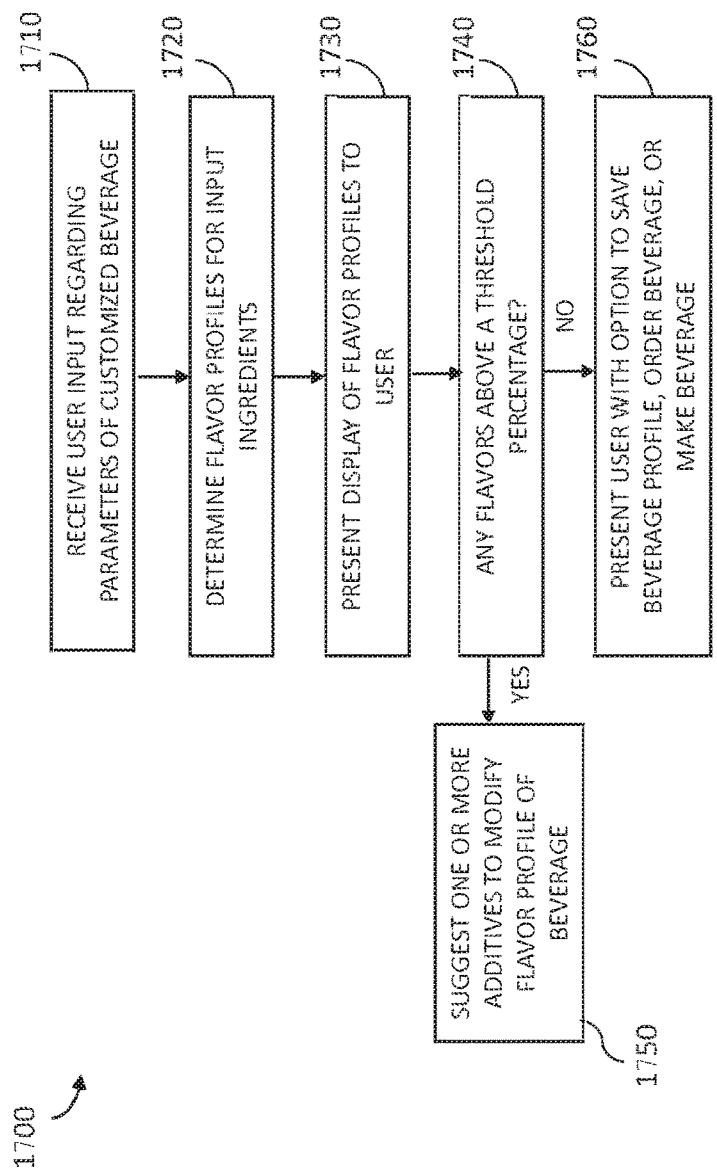
FIG. 17 is a flow diagram illustrating a method for customizing a beverage for a user.

As described herein, the system 740 may perform various processes, operations, or methods when determining flavor profile information for beverages and/or recommending beverages or ingredients to users. FIG. 17 is a flow diagram illustrating a method 1700 for customizing a beverage for a user. Aspects of the method 1700 may be performed by the beverage profile system 740 and, accordingly, is described herein merely by way of reference thereto. It will be appreciated that the method 1700 may be performed on any suitable hardware.

As depicted, the method 1700 may perform operations to create a beverage and/or determine modifications to adjust the flavor of a beverage. For example, in operation 1710, the system 740 receives user input regarding parameters of a customized beverage (see FIG. 16A), and in operation 1720, determines a flavor profile for the input ingredients.

In operation 1730, the system 740 presents, or causes to present, the flavor profiles to the user. In operation 1740, the system 1740 determines whether any flavor types are above a threshold percentage. When there is a flavor type above a threshold percentage, the method 1700 proceeds to operation 1750, and the system 740 suggests one or more additives to add to the beverage to modify the flavor profile of the beverage (see FIG. 16B).

When there is no flavor type above a threshold percentage, the method 1700 proceeds to operation 1760, and the system 740 presents the user options to perform one or more actions with respect to the beverage (see FIG. 16C), such as save the customized beverage, order smoothie pods associated with the beverage, make the beverage (e.g., using machine 720), and so on.

Figure 18:
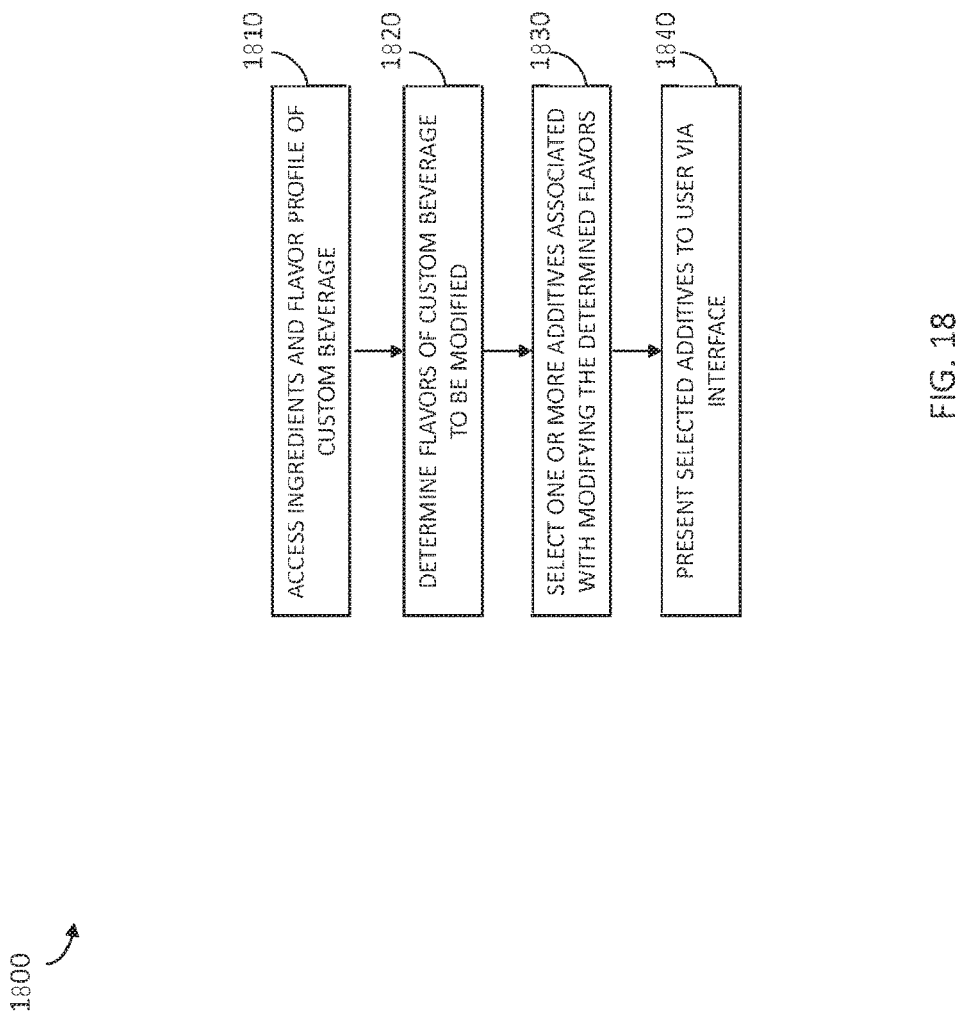
FIG. 18 is a flow diagram illustrating a method for modifying a flavor profile of a beverage for a user.

FIG. 18 is a flow diagram illustrating a method 1800 for modifying a flavor profile of a beverage for a user. Aspects of the method 1800 may be performed by the beverage profile system 740 and, accordingly, is described herein merely by way of reference thereto. It will be appreciated that the method 1800 may be performed on any suitable hardware.

As depicted, the method 1800 may perform operations to determine and recommend additives and other flavored substances used to adjust the flavor of a beverage. For example, in operation 1810, the system 740 accesses the ingredients and/or flavor profile for a customized beverage, and in operation 1820, determines flavors of the beverage to be modified.

In operation 1830, the system 740 selects or identifies one or more additives associated with modifying the determined flavor of the beverage (see Table 2), and in operation 1840, the system 740 presents the selected additives to the user via the user interface of the user device 710 or machine 720 (see FIG. 16B).

For example, the method 1800 may determine that a flavor profile of the smoothie pod that is based on the ingredients selected by the user includes at least one flavor type having a percentage of the flavor profile that is outside of an acceptable threshold percentage range of the flavor profile (e.g., above 60 percent of the flavor profile), and present a suggestion via the graphical user interface of one or more additional ingredients to be added to the smoothie pod to modify the percentage of the flavor type to be within the acceptable threshold percentage range (e.g., lower than 60 percent) of the flavor profile.

As another example, the method 1800 may determine a customized beverage has a flavor profile of "bitter" or "sweet" or another single type of flavor, and present recommendations based on the determined single flavor profile for the beverage.

Thus, in some embodiments, the system 740 may perform a method for designing a smoothie pod or other beverage by receiving input from a user via the user device 710 that communicates with the system 740 over a network, wherein the input is received via a graphical user interface and includes selections of ingredients to be added to the smoothie pod, determining, that a flavor profile of the smoothie pod that is based on the ingredients selected by the user includes at least one flavor type having a percentage of the flavor profile that is outside of an acceptable threshold percentage range of the flavor profile, and presenting a suggestion via the graphical user interface of one or more additional ingredients to be added to the smoothie pod to modify the percentage of the flavor type to be within the acceptable threshold percentage range of the flavor profile.

Examples of Ordering Beverage Pods

As described herein, in some embodiments, the systems and methods perform operations to generate and/or order customized beverages (e.g., smoothies) for users. For example, an ordering system (e.g., module 830 or 1530) may perform the following steps when ordering beverage pods for use in the beverage machine 720:

Calculate a cost of ingredients and manufacturing for a smallest possible batch of pods (e.g., 5 ingredients at $0.25 each times 50 pods);

Calculate a sales margin based on retailer/manufacturer limits (e.g., 20% of manufacturing cost);

Calculate a cost outlay for different batch sizes (e.g., 50 pods=100%, 100 pods=99%, 500 pods=80%, and so on);

Present the calculated cost outlays to the users, which select a quantity based on the estimated costs; and Complete an order that considers the number of ingredients, sales margin, cost outlay, and/or other factors.

Therefore, in some embodiments, the systems and methods described here customize smoothie pods for users as well as customize quantities of smoothie pods to be ordered on behalf of users, among other benefits.

Portable, Pod-Based Smoothie Maker

The apparatuses described herein provide a portable, pod-based beverage maker, such as an apparatus that makes smoothies and other similar beverages from pod-based ingredient mixtures. The apparatus provides an easy and simple way to combine ingredients in pods with water, ice, and other mixing liquids.

For example, the beverage maker may receive one or more pods above a larger container or vessel such as a plastic cup for use by a user. The beverage maker can further include components that allow a user to twist a carousel through a number of positions in order to selectively add beverage ingredients to the container. For example, a user turns the carousel though a set of positions, where at each position the carousel "clicks" into place. In a first position, one or more pods are loaded into the beverage maker while being shielded from an inner area of the container. In a second position, at least one of the pods may be opened and its contents can enter the inner area while being shielded from liquid, thereby allowing the beverage maker to be carried around without fear of any spoilage since a consumable beverage has yet to be created. Thereafter, a liquid opening is exposed by rotating the carousel to a third position, and the container is filled with liquid. Once filled, the pods and a liquid inlet are both shielded from the beverage by rotating the carousel back to the first position, and a user can handshake the beverage maker to create a consumable beverage without spilling the contents. In some embodiments the carousel can have one or more additional positions. For example, in certain embodiments, the user can rotate the carousel to an additional position between the second and third positions. In this additional position, the liquid inlet and pods are fully shielded from the inner area of the container. Accordingly, contents from the one or more pods cannot reenter the previously emptied pods while a user carries or otherwise transports the beverage maker.

The beverage pods, or smoothie pods, may be pods or cartridges containing specific mixtures of ingredients. For example, a pod may include a mixture of various freeze dried fruits (e.g., freeze dried bananas, strawberries, blueberries, mango, etc.), freeze dried vegetables (e.g., kale, spinach, beets, etc.), additive powders (e.g., protein powders, powdered greens, oils, seeds, supplements, flavors, etc.). In some cases, a pod may include a mixture of many different ingredients. In other cases, the pod may include one or more ingredients.

Figure 19:
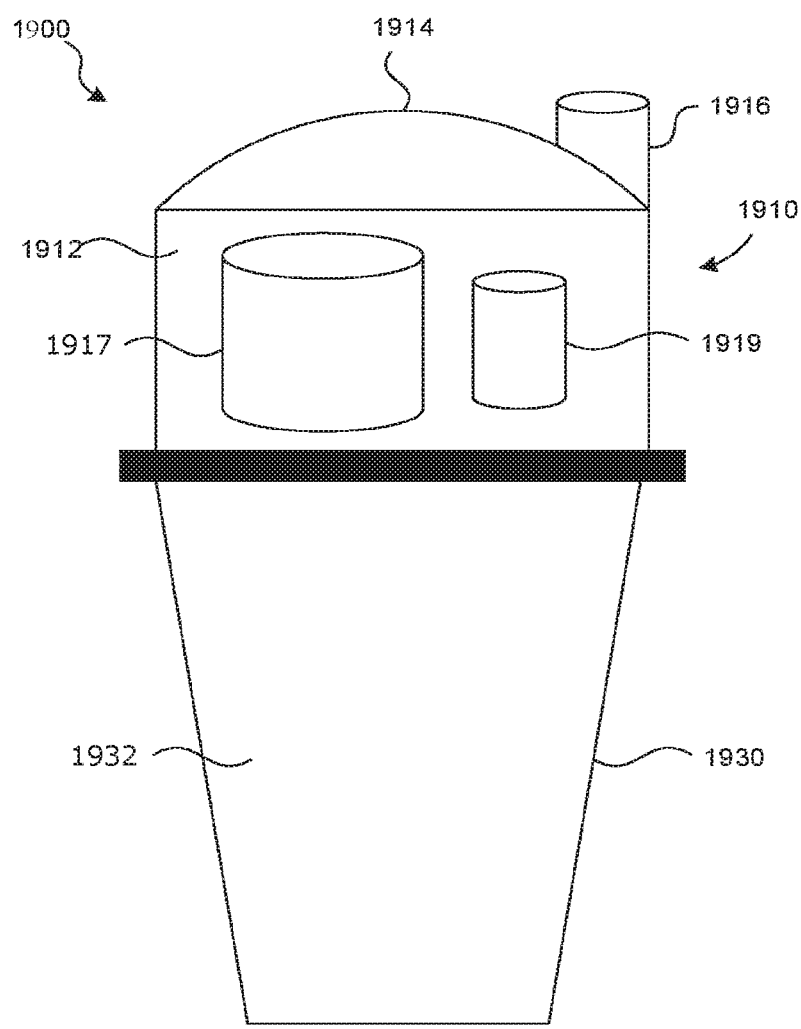
FIG. 19 is a diagram showing a side view of a beverage maker configured in accordance with the present technology.

FIG. 19 is a side view of a beverage maker 1900 in accordance with some embodiments of the present technology. As illustrated, the beverage maker 1900 includes a carousel 1920 positioned between top 1910 and container bottom 1930. The bottom 1930 may be configured as a bottle, cup, or other similar container, typically sized to be held in one hand by a user. In some embodiments, the carousel 1920 is permanently coupled to pod holder 1912 or another portion of the top 1910. The carousel 1920 and top 1910 can therefore form a cap structure that can be configured for attachment to any type of container bottom 1930. In other embodiments, the carousel 1920 is a separate component of beverage maker 1900 that can be removed from the top portion 1910. One advantage of providing the carousel 1920 as a separable component from the top 1910 is that it can make cleaning the beverage maker 1900 easier. That is, a user can separate and wash the carousel 1920 along with the bottom 1930 without having to wash the top 1910, which in some embodiments is not exposed to the created beverage. In yet other embodiments, the carousel 1920 can be adjustably positionable within or above the container bottom 1930. For example, the carousel 1920 can be lowered into the inner area 1932 of the container bottom 1930 in order to reduce the volume of the inner area 1932 (e.g., in order to make a smaller consumable beverage).

Top 1910 further includes pod holder 1912, lid 1914, and liquid fill inlet 1916. Liquid fill inlet 1916 is configured to receive a liquid therethrough. Pod holder 1912 is configured to receive at least one pod containing beverage contents. Specifically, pods can be inserted into the pod holder 1912 when the lid 1914 has been removed. In some embodiments, once pods are inserted into the pod holder 1912, the lid 1914 secures the pods against carousel 1920. In certain embodiments, the lid 1914 is detachable from the top 1910. In other embodiments, the lid 1914 can pivot, swing, or otherwise move to provide access to the pod receptacles 1917 and 1919.

In the illustrated embodiment, pod holder 1912 includes primary pod receptacle 1917 and supplemental pod receptacle 1919. Primary pod receptacle 1917 can receive, for example, a larger pod containing freeze dried fruits and/or vegetables. Supplemental pod receptacle 1919 can receive, for example, a smaller pod containing additive powders, oils, seeds, supplements, flavors, etc. In other embodiments, the pod holder 1912 contains a single pod receptacle, or more than two pod receptacles.

Carousel 1920 is rotatable and is generally configured to provide selective access to an inner area 1932 of container bottom 1930 from the top 1910. More specifically, carousel 1920 can include one or more pod openings and a liquid opening that provide access to the inner area 1932 of container bottom 1930. The openings are selectively shielded from pod receptacles 1917 and 1919 and liquid fill inlet 1916 depending on the position of the carousel 1920.

FIGS. 20-23 illustrate cross-sectional side views of the carousel 1920 and top 1910 of the beverage maker 1900 shown in FIG. 19. In particular, FIGS. 20-23 show the carousel 1920 in different positions that provide varying degrees of access to the container bottom 1930 (not pictured) from the top 1910. In the illustrated embodiments, carousel 1920 includes primary pod opening 2002, supplemental pod opening 2004, and liquid opening 2006, all extending through the carousel 1920 and positioned above the container bottom 1930 to provide access between the top 1910 and container bottom 1930. Primary pod opening 2002 is aligned along a common axis with primary pod receptacle 1917, supplemental pod opening 2004 is aligned along a common axis with supplemental pod receptacle 1919, and liquid opening 2006 is aligned along a common axis with liquid fill inlet 1916. In certain embodiments, the carousel 1920 includes more or fewer openings depending on the number of pod receptacles included in the pod holder 1912. For example, if the pod holder 1912 includes only one primary pod receptacle 1917, the carousel can have only a single corresponding opening 2002 and no supplemental pod opening 2004.

According to the present technology, the carousel 1920 can generally be twisted or rotated through one or more positions that provide the top 1910 with varying access to the inner area 1932 of container bottom 1930. For example, as described in detail below, a user can twist the carousel 1920 in order to rotate a series of grommet blanks, grommets, and pod openers relative to the fixed top 1910 and openings 2002, 2004, and 2006. In some embodiments, the carousel 1920 includes a locking mechanism that locks the carousel 1920 in place at each of the one or more positions. For example, the carousel 1920 can include a series of grooves and corresponding inserts that fit together at each position. By applying more rotational force to the carousel 1920, the user can overcome the locking mechanism and move the beverage maker 1900 to another position. In certain embodiments, the carousel 1920 further includes a mechanism that permits the carousel 1920 to rotate in only a single direction (e.g., in the counterclockwise direction). In other embodiments, the carousel 1920 is rotatable in either direction such that the user can rotate the carousel 1920 back-and-forth between adjacent positions.

Figure 20:
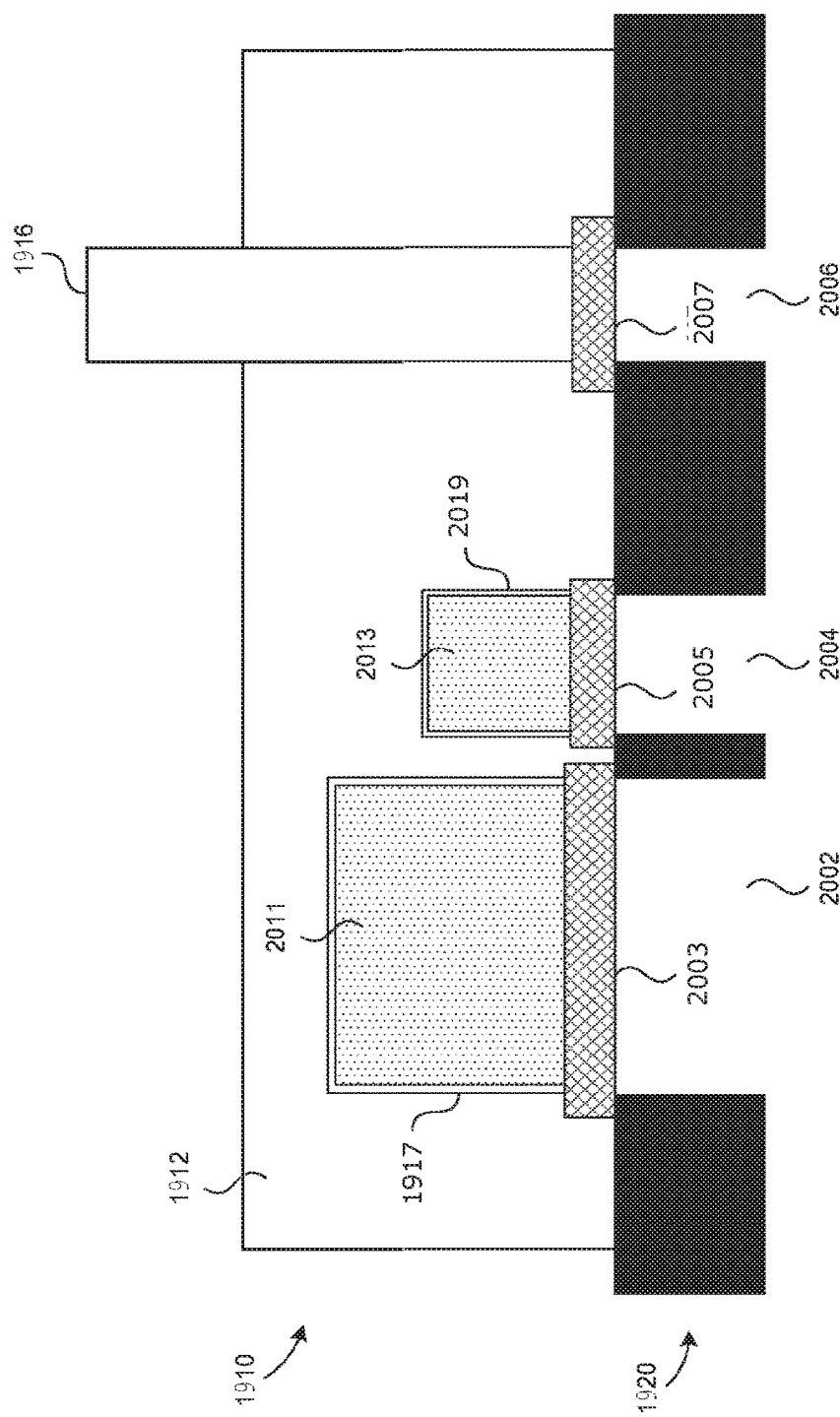
FIG. 20 is a cross-sectional side view of a top portion of the beverage maker shown in FIG. 19, and showing a carousel of the beverage maker in a first position.

FIG. 20 shows the top 1910 with the lid 1914 removed so that primary pod 2011 can be inserted in the primary pod receptacle 1917 and supplemental pod 2013 can be inserted into supplemental pod receptacle 1919. As illustrated, the pods 2011 and 2013 contain beverage contents when they are inserted. The carousel 1920 is in a first position. In the first position, grommet blanks 2003, 2005, and 2007 block the primary pod opening 2002, supplemental pod opening 2004, and liquid opening 2006, respectively. The top 1910, and specifically the pod receptacles 1917 and 1919 and liquid fill inlet 1916, are therefore shielded from the inner area 1932 of bottom 1930. The grommet blanks 2003, 2005, and 2007 can be made of rubber or other waterproof materials.

In some embodiments, the pods 2011 and 2013 are positioned on the grommet blanks 2003 and 2005. In such embodiments, the lid 1914 can be attached to the top 1910 and can engage a top portion of the pods 2011 and 2013 to secure the pods in place against the grommet blanks 2003 and 2005. In other embodiments, the pods 2011 and 2013 are positioned slightly above the grommet blanks 2003 and 2005. For example, an internal structure within the pod receptacles 1917 and 1919, such as one or more struts, can keep the pods 2011 and 2013 from being supported by only the rubber grommet blanks 2003 and 2005. In yet other embodiments, the pods 2011 and 2013 can include a flange or other structure that supports the pods 2011 and 2013 within the receptacles 1917 and 1919. For example, pods 2011 and 2013 can have an upper portion including a flange that is configured to extend outside the receptacles 1917 and 1919 to support the pods 2011 and 2013 via an upper surface of the receptacles 1917 and 1919. In still other embodiments, the pods 2011 and 2013 are shaped to engage an inner surface of the pod receptacles 1917 and 1919 and are therefore seated within the receptacles 1917 and 1919.

Figure 21:
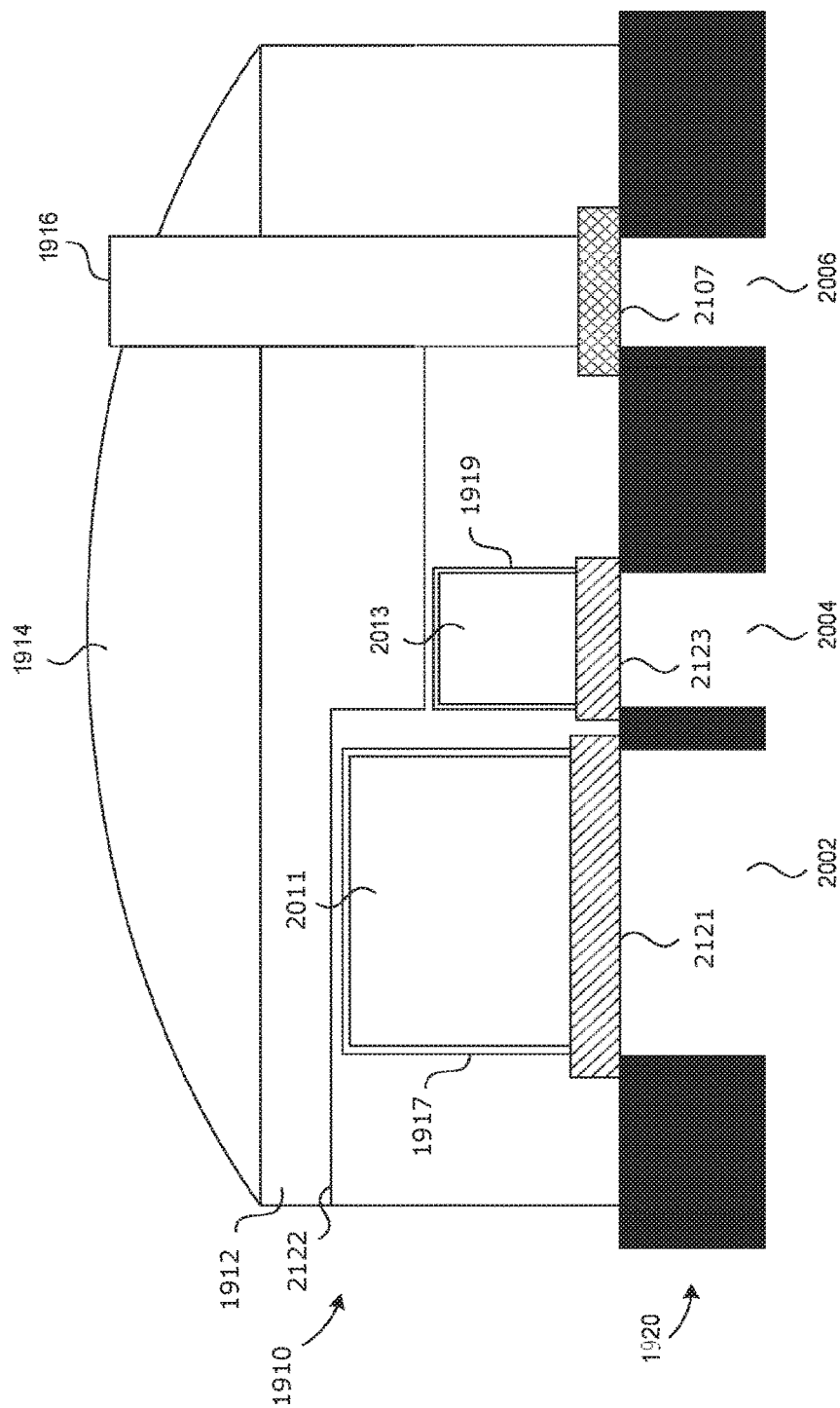
FIG. 21 is a cross-sectional side view of a top portion of the beverage maker shown in FIG. 19, and showing the carousel in a second position.

FIG. 21 shows the carousel 1920 in a second position. In the second position, a bottom surface of the primary pod 2011 and a bottom surface of supplemental pod 2013 are cut open to permit contents within the pods 2011 and 2013 to move to the inner area 1932 of the container bottom 1930. As illustrated, the pods 2011 and 2013 are emptied of their contents in the second position. A grommet blank 2107 blocks the liquid opening 2006 so that the liquid fill inlet 1916 is shielded from the inner area 1932 of the container bottom 1930. The carousel 1920 includes primary pod opener 2121 and supplemental pod opener 2123 that comprise one or more cutting elements. The cutting elements may include, for example, a plurality of small pins, a cutting edge, or other device configured to cut, pierce or otherwise penetrate a bottom surface of pods 2011 and 2013. In certain embodiments, the pods have a foil or plastic bottom surface which is cut open to allow the pod contents to fall into the container bottom 1930 through pod openings 2002 and 2004.

In some embodiments, the pod openers 2121 and 2123 operate to open the pods 2011 and 2013 when the carousel is turned from the first position to the second position. That is, rotating the carousel from the first position to the second position causes the openers 2121 and 2123 to engage the bottom surfaces of pods 2011 and 2013, respectively, to permit the pod contents to move to the container bottom 1930. A bottom surface 2122 of lid 1914 can engage top portions of the pods 2011 and 2013 to secure the pods 2011 and 2013 against the pod openers 2121 and 2123 while the carousel 1920 is rotated from the first position to the second position. The pod openers 2121 and 2123 can include openings or space between cutting elements to allow the pod contents to fall through the pod openers 2121 and 2123 and into the container bottom 1930. In other embodiments, the pod openers 2121 and 2123 are only aligned with the pods 2011 and 2013 as the carousel is twisted from the first to the second position. Then, in the second position, the pods 2011 and 2013 are directly above the primary pod opening 2002 and supplemental pod opening 2004 to allow the contents of the pods 2011 and 2013 to fall into the container bottom 1930 (i.e., the contents does not pass through the pod openers 2121 and 2123 to enter to the container bottom 1930).

Figure 22:
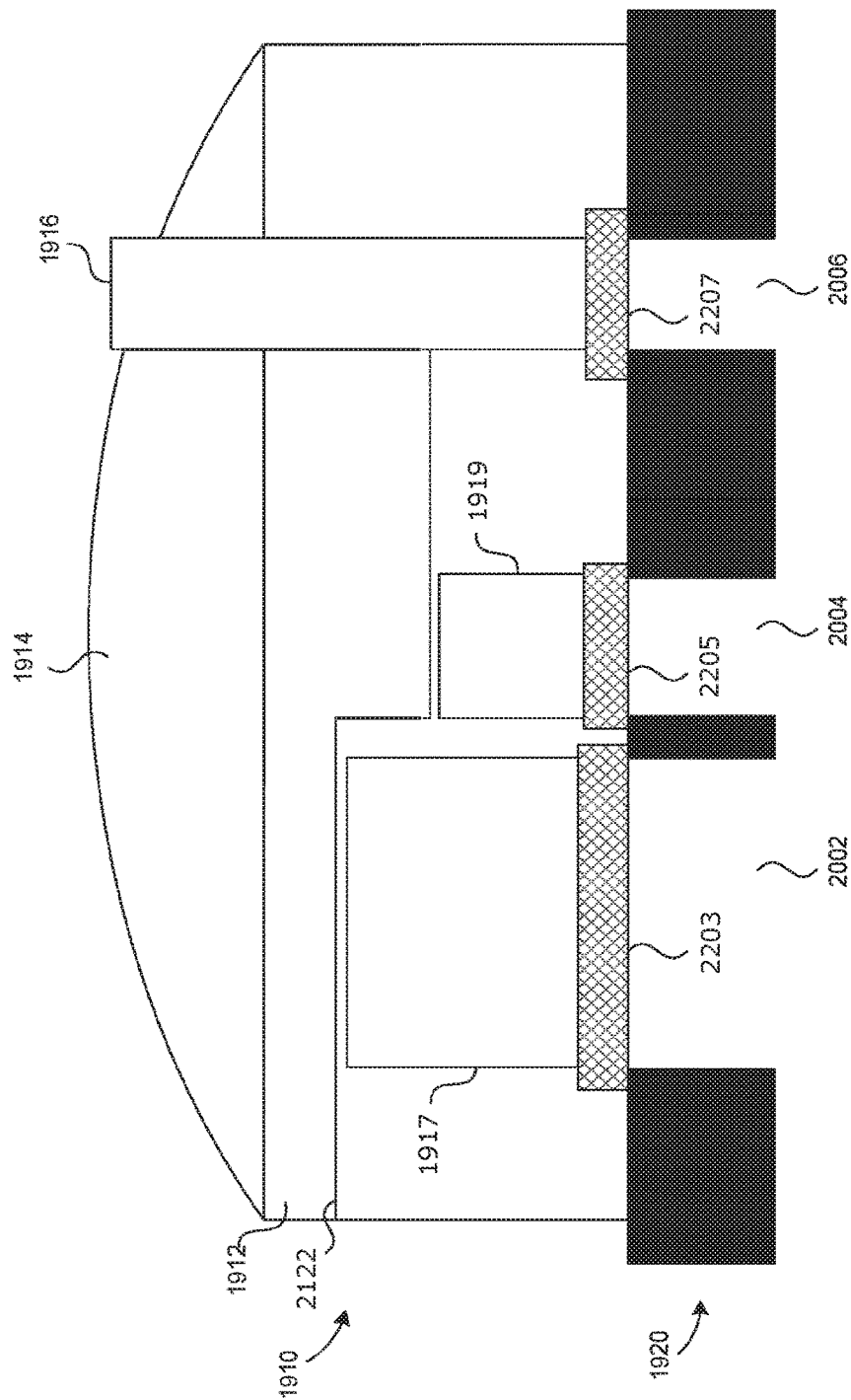
FIG. 22 is a cross-sectional side view of a top portion of the beverage maker shown in FIG. 19, and showing the carousel in an optional third position.

FIG. 22 shows the carousel in an optional third position. The third position is similar to the first position in that grommet blanks 2203, 2205, and 2207 block the primary pod opening 2002, supplemental pod opening 2004, and liquid opening 2006, respectively. The top 1910 is therefore entirely shielded from the inner area 1932 of container bottom 1910. The optional third position permits the user to detach or move the lid 1914 from the top 1910 and to remove the emptied primary pod 2011 and supplemental pod 2013. As illustrated, the pods 2011 and 2013 have been removed from the receptacles 1917 and 1919 and the top 1914 has subsequently been replaced. This optional third position also permits a user to carry or transport the beverage maker 1900 without backflow of the pod contents into the emptied pods 2011 and 2013. For example, if transported in the optional third position, the beverage maker 1900 will prevent backflow of the pod contents into the top 1910 if the beverage maker is inverted or otherwise jostled.

Figure 23:
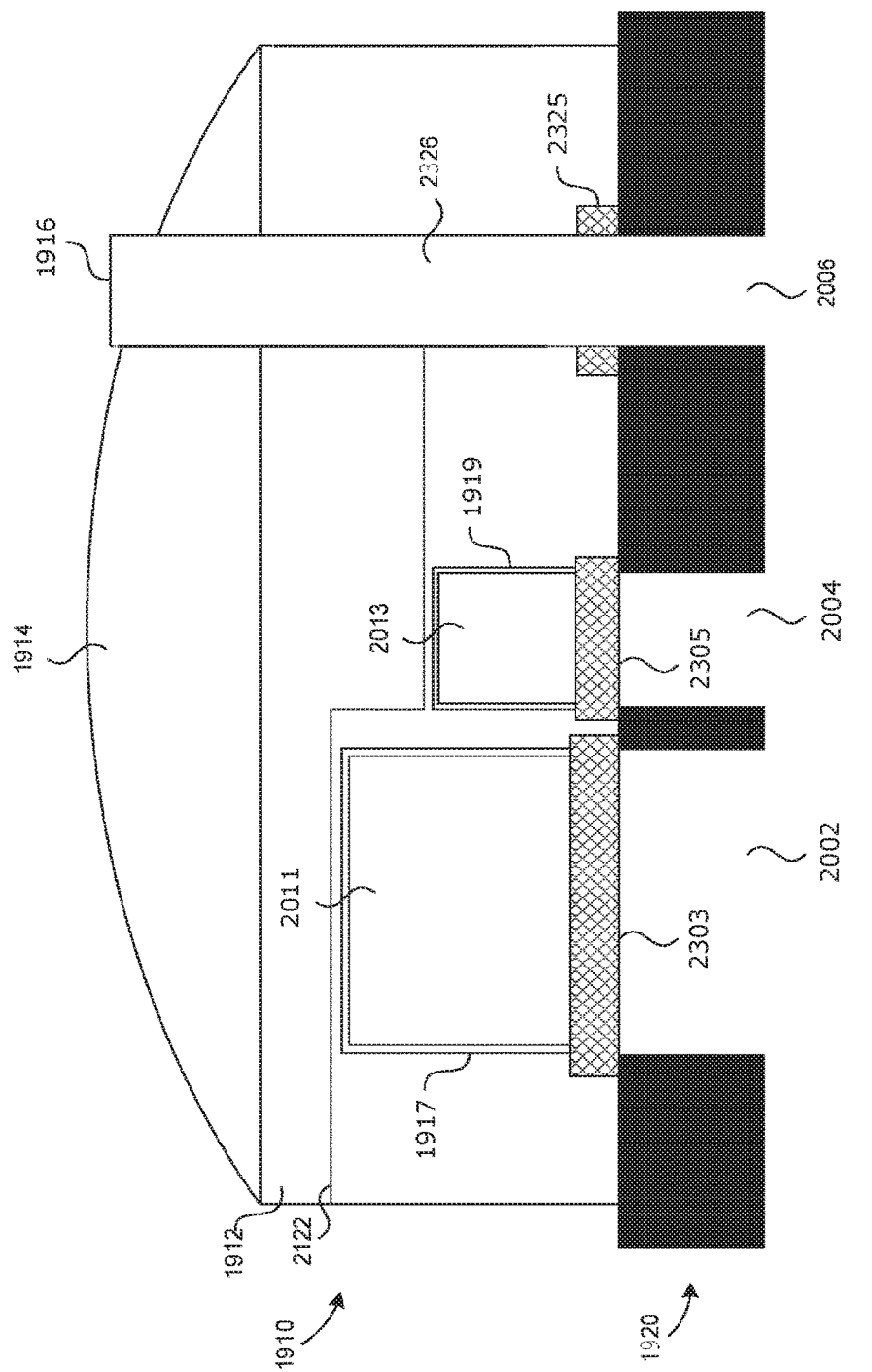
FIG. 23 is a cross-sectional side view of a top portion of the beverage maker shown in FIG. 19, and showing the carousel in a fourth position.

FIG. 23 shows the carousel 1920 in a fourth position. The emptied pods 2011 and 2013 have yet to be removed from the top 1910 (e.g., removed in the optional third position.) In the fourth position, the liquid opening 2006 is exposed to the fill inlet 1916, while grommet blanks 2303 and 2305 block the primary pod opening 2002 and supplemental pod opening 2004, respectively. The liquid fill inlet 1916 and liquid opening 2006 together define a channel 2326 through which liquid can flow from the top 1910 and into the container bottom 1930. Water, other liquids, or both, can therefore be added to into the beverage maker 1900 while the pods 2011 and 2013 are shielded from the container bottom 1930. In certain embodiments, the carousel 1920 includes liquid grommet 2325 positioned between the fill inlet 1916 and liquid opening 2006. Liquid grommet 2325 further defines the channel 2326 and functions to seal the channel 2326 in order to prevent liquid from leaking into other portions of the top 1910.

Now described, with reference to FIGS. 19-23, is an exemplary method of using a beverage maker 1900 configured in accordance with the present technology to create a consumable beverage. To begin, while the carousel is in the first position, the lid 1914 is removed and one or more pods (e.g., primary pod 2011 and supplemental pod 2013) are inserted into corresponding receptacles in the top 1910 (e.g., primary pod receptacle 1917 and supplemental pod receptacle 1919). The lid 1914 is then reattached to the top 1910 in order to secure the pods against grommet blanks 2003 and 2005 in the carousel.

Next, the user twists the carousel 1920 by hand from the first position to the second position to release the contents of pods 2011 and 2013 into the inner area 1932 of the container bottom 1930. In some embodiments, the user can then twist the carousel 1920 to the optional third position. In the optional third position, the user can remove the lid 1914 and the pods 2011 and 2013. The user may also transport the beverage maker 1900 in the third position-including inverting the beverage maker 1900 without fear of the contents reflowing into the top 1910. The user also need not worry about spoiling, since a consumable beverage including liquid has yet to be created. Thereafter, the user may rotate the carousel 1920 to the fourth position and fill the container bottom 1930 with liquid via fill inlet 1916. Finally, the carousel 1920 may be rotated back to the first position and the beverage maker 1900 shaken to create a consumable beverage such as a smoothie. Alternatively, the carousel 1920 can be rotated back to the optional third position and the beverage maker 1900 shaken in the third position.

In some embodiments, the carousel 1920 is configured such that a single full rotation in one direction (e.g., the counterclockwise direction) will cause the carousel 1920 to pass through each of the first through fourth positions. In other embodiments, the carousel 1920 may require more or fewer rotations in order to pass through each position. Moreover, in certain embodiments, the carousel 1920 is configured such that it can only be rotated sequentially through the different positions. For example, the carousel 1920 may be configured to rotate only in the counterclockwise direction such that the first through fourth positions can only be accessed in numerical order. In still other embodiments, the carousel 1920 is freely rotatable through the different positions in any order.

Of course, other variations of the beverage maker 1900, including other components, geometries, and/or configurations, may be utilized. For example, instead of rotating a series of grommet blanks, grommets, and pod openers relative to the fixed top 1910 and openings 2002, 2004, and 2006, the top 1910 could be rotated relative to the openings 2002, 2004, and 2006. That is, the pods 2011 and 2013 could be rotated relative to the carousel 1920 and the openings 2002, 2004, and 2006 formed therein, to achieve functionally similar positions as those described above. Alternatively, the openings 2002, 2004, and 2006 in carousel 1920 could be rotated relative to fixed pods 2011 and 2013 to achieve similar positions.

As another example, the beverage maker 1900 may include an accelerometer that tracks the shaking of the bottle, where the data is communicated to a user device (e.g., smartphone). Based on the accelerometer data, a number of calories burned can be calculated. Additionally, the accelerometer data could be used to determine when the beverage maker 1900 has been shaken a sufficient amount. Once the sufficient amount has been reached, the user device could alert the user with haptic feedback or an auditory alert. In certain embodiments, the beverage maker 1900 includes an accelerometer, a communications component, and a microprocessor coupled to the accelerometer and the communications component to track shaking of the beverage maker 1900 and transmit data reflecting the shaking to a smartphone.

As another example, pods (e.g., pods 2011 and 2013) are opened immediately upon or soon after placement by the user within the beverage maker 1900, and the contents are dumped into a separate compartment. The compartment is then opened by turning the carousel 1920, allowing the contents to enter the container bottom 1930. The compartment is then closed off by further turning the carousel 1920. This allows the user to immediately dispose of the pods, and would allow for a smaller form factor for the beverage maker 1900, among other things.

As another example, the beverage maker 1900 may include an insulated compartment for storing ice. In some embodiments, the compartment is configured to be separate from, but adjacent to, the inner area 1932 of container bottom 1930 so as to keep the inner area 1932 cool. In other embodiments, the compartment could be opened to allow the ice to enter the container bottom 1930. The ice could either be in cube form to help keep the beverage cool for longer, or the ice could be crushed in order to give the smoothie a more traditional consistency.

As another example, the carousel 1920 of beverage maker 1900 may be adjustable in the vertical direction. This would allow the user to manually set a limit for the amount of liquid to be added to the container bottom 1930. Once the liquid has been added, the carousel 1920 can be adjusted upwards to allow for extra room in the inner area 1932 of container bottom 1930 to aid in the shaking process. In some embodiments, the carousel 1920 is lowered vertically to a liquid-fill position within the container bottom 1930 when the carousel 1920 is in the fourth position. The carousel 1920 is raised vertically to a shaking position when the carousel 1920 is in either the optional third position or in the first position to facilitate the shaking process. A volume of the inner area 1932 is greater when the carousel 1920 is in the shaking position than when the carousel is in the liquid-fill position. As another example, a vibrator in the carousel 1920 may be activated when the carousel 1920 is in the second position. The vibrator may assist in the release of powders or other contents from the pods, ensuring that the entirety of the pods' contents enter the container bottom 1930 to be included in the beverage. The vibrator can turn off once the carousel 1920 rotates to another position. In some embodiments, the one or more pods are smoothie pods, and beverage maker 1900 includes a vibrator that activates only when the carousel 1920 is in the second position to assist in the release of smoothie contents from the pods into the container bottom 1930.

Portable, Pod-Based Smoothie Maker

Systems and methods for customizing beverage profiles and associated consumption programs, such as customizing smoothie pods to be used in making smoothies and other beverages, are described. For example, the systems and methods may receive or obtain information associated with a user's previous, current, and/or future activities (e.g., workouts or training sessions), a user's sleep activities, a user's current mental acuity or sharpness, a user's health or fitness, and so on, and determine or create a beverage profile for the user based on the information for the user.

The systems and methods may make beverages (e.g., smoothies or other drinks) and/or order or create smoothie pods (e.g., containers of ingredients used when making a beverage) having the beverage profile. The systems and methods, therefore, may provide the user with a customized smoothie or other beverage that includes ingredients useful in improving, benefiting, or mitigating the user's health, performance, mental state, and/or other characteristics or states, among other benefits.

Suitable Computing Environment

Figure 24:
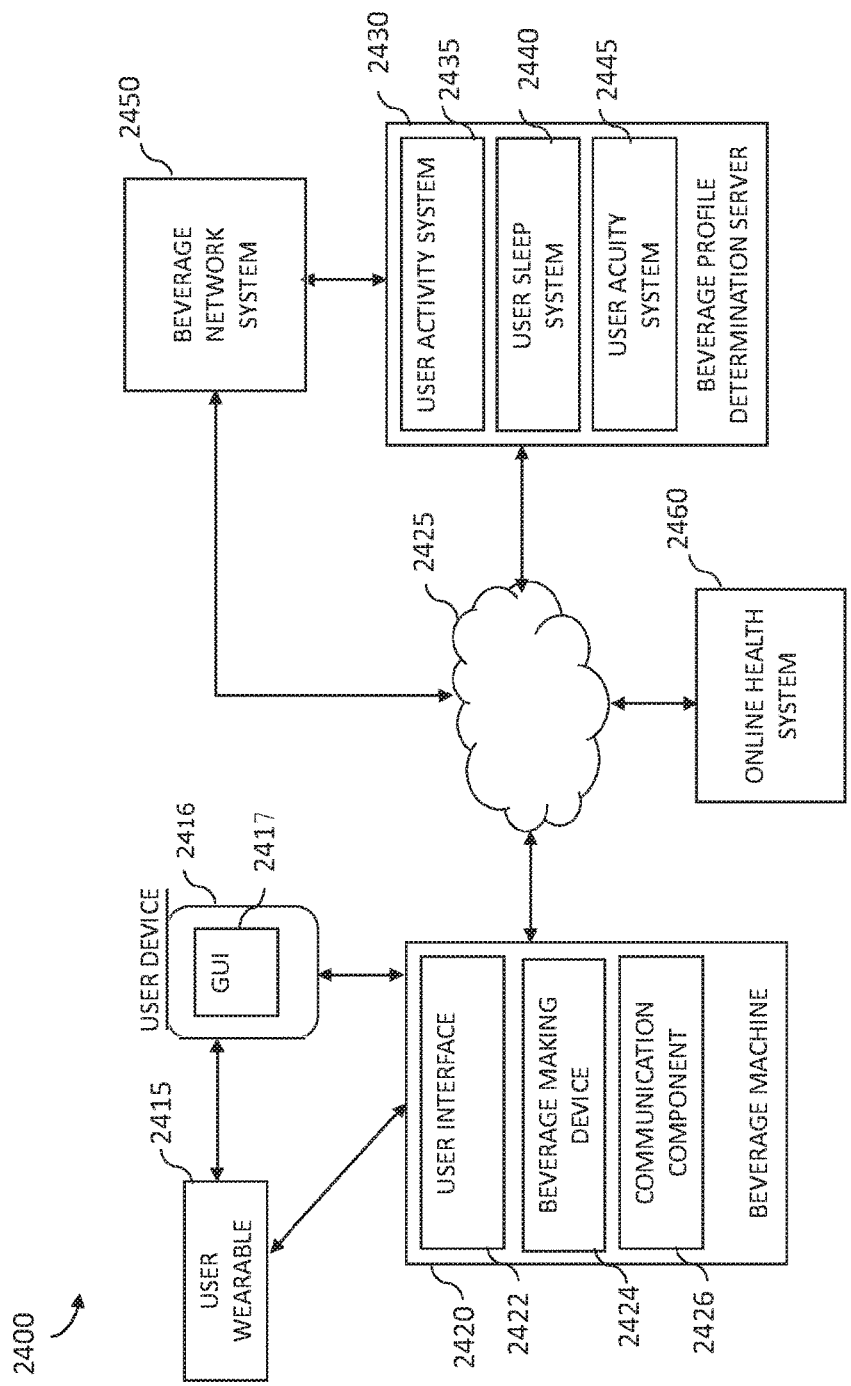
FIG. 24 is a block diagram illustrating a suitable computing environment for providing beverages having customized beverage profiles to a user.

As described herein, the systems and methods customize beverage profiles for users based on various aspects or characteristics associated with the users, and create or customize smoothie pods having ingredients that include the customized beverage profiles. FIG. 24 is a block diagram illustrating a suitable computing environment 2400 for providing beverages having customized beverage profiles to a user.

The computing environment 2400 includes a user device 2410 (having a user interface 2412), such as a mobile device, which may be paired with a user wearable device 2415 or peripheral configured to capture and/or measure information associated with the user. A beverage machine 2420, such as a machine, device, or refrigerator configured to create beverages from pods or other ingredients sources, may be directly connected to the user device 2410 or wearable device 2415, or may communicate with the user device 2410, the wearable device 2415, or other devices, systems, and/or servers over a network 2425, such as the Internet.

The beverage machine 2420, therefore, may include a communication component 2426 that facilitates communicating with various devices over the network 2425, a user interface component 2422 that renders, displays, and/or presents information to users via a display, such as a graphical user interface (GUI), and/or receives input from users via the display or via various manual controls of the beverage machine 2420. The beverage machine 2424 also includes a beverage making device 2422, such as a blender or other pod-based beverage creating or making devices.

For example, the beverage making device 2422 may be configured to extract contents (e.g., ingredients) within a beverage pod, such as a smoothie pod, and mix or combine the extracted contents with various liquids or other mixing substances, such as water, ice, milk, and so on, based on received or stored programs, recipes, and/or instructions. The beverage pods may be pods or cartridges containing specific mixtures of ingredients. For example, a pod may include a mixture of various freeze dried fruits (e.g., freeze dried bananas, strawberries, blueberries, mango, and so on), freeze dried vegetables (e.g., kale, spinach, beets, and so on), additive powders (e.g., protein powders, powdered greens), oils, seeds, supplements, flavors, and so on. In some cases, a pod may include a mixture of many different ingredients. In other cases, the pod may include one or more ingredients.

A beverage profile determination server 2430 may support and/or provide a "beverage network" or other cloud-based systems that perform various actions or functions to determine or create beverage profile recommendations for users. For example, the server 2430, which may communicate with the beverage machine 2420, the user device 2410, and/or the wearable device 2415 over the network 2425, may include various different systems configured to access, receive, obtain, or retrieve certain information about a user (e.g., activity or health information), and generate beverage profiles for beverages targeted to the user based on the information about the users.

Example systems, which are discussed in greater detail herein, include a user activity system 2435 configured to generate or determine beverage profiles for beverages based on activity information associated with a user, a user sleep system 2440 configured to generate or determine beverage profiles for beverages based on sleep activity associated with the user, and a user acuity system 2445 configured to generate or determine beverage profiles for beverages based on mental acuity information measured for a user.

A beverage network system 2450 may be part of, or associated with, the server 2430 and its various beverage profile recommendation systems. The beverage network system 2450 may facilitate interactions between the systems of the server 2430 and one or more online health systems 2460, such as online wellness programs, online health monitoring systems, medical or doctor partner networks, and so on. Thus, in some embodiments, various third-party systems, such as the online system 2460, may access the operations of the server 2430 via one or more Software As A Service (SaaS) interfaces provided by the beverage network system 2450.

FIG. 24 and the discussion herein provide a brief, general description of the suitable computing environment 2400 in which the system can be supported and implemented. Although not required, aspects of the system are described in the general context of computer-executable instructions, such as routines executed by a general-purpose computer, e.g., mobile device, a server computer, or personal computer. Those skilled in the relevant art will appreciate that the system can be practiced with other communications, data processing, or computer system configurations, including: Internet appliances, hand-held devices (including tablet computers and/or personal digital assistants (PDAs)), all manner of cellular or mobile phones, multi-processor systems, microprocessor-based or programmable consumer electronics, set-top boxes, network PCs, mini-computers, mainframe computers, and the like. Indeed, the terms "computer," "host," and "host computer," and "mobile device" and "handset" are generally used interchangeably herein, and refer to any of the above devices and systems, as well as any data processor.

Aspects of the system can be embodied in a special purpose computing device or data processor that is specifically programmed, configured, or constructed to perform one or more of the computer-executable instructions explained in detail herein. Aspects of the system may also be practiced in distributed computing environments where tasks or modules are performed by remote processing devices, which are linked through a communications network, such as a Local Area Network (LAN), Wide Area Network (WAN), or the Internet. In a distributed computing environment, program modules may be located in both local and remote memory storage devices.

Figure 25:
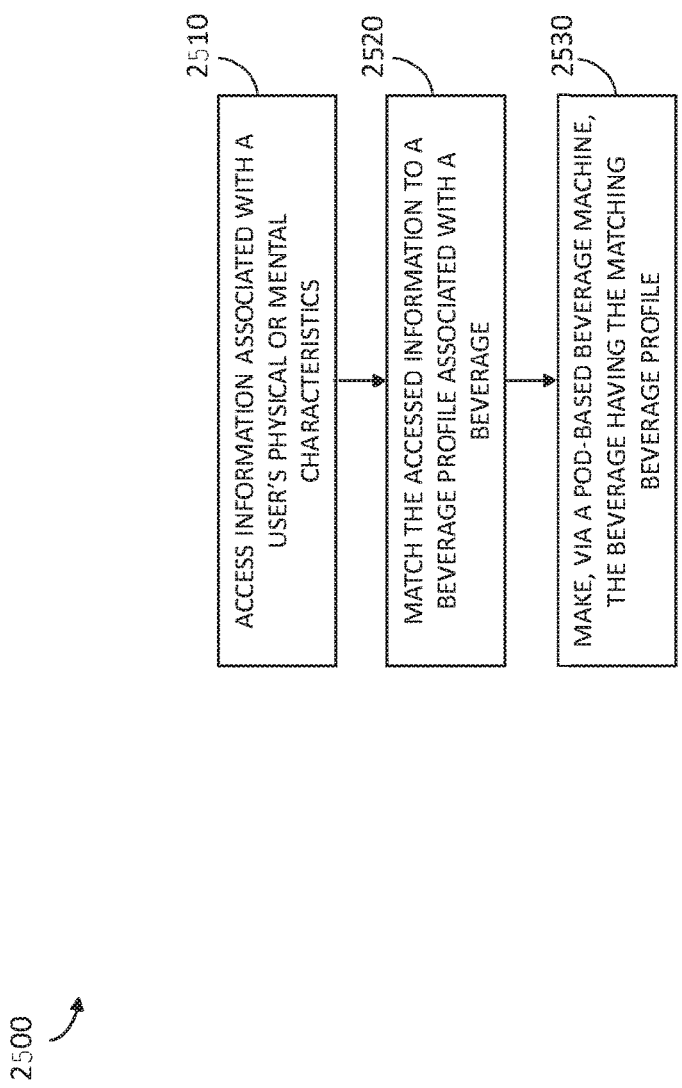
FIG. 25 is a flow diagram illustrating a method for making a beverage for a user that is based on mental or physical characteristics of a user.

As described herein, the beverage profile determination server 2430, therefore, may perform various processes, methods, or operations when creating and/or making beverages (e.g., customized pod-based smoothies) for users. FIG. 25 is a flow diagram illustrating a method 2500 for making a beverage for a user that is based on mental or physical characteristics of a user. Aspects of the method 2500 may be performed by the beverage profile determination server 2430 and, accordingly, is described herein merely by way of reference thereto. It will be appreciated that the method 2500 may be performed on any suitable hardware.

In operation 2510, the server 2430 accessed information associated with a user's physical or mental characteristics. For example, the server 2430, via one or more associated systems, may access user activity information, user sleep activity information, mental acuity information, and so on, measured or provided by the user device 2410, the wearable device 2415, and/or the beverage machine 2420 (e.g., input by the user to the GUI 2422 of the machine 2422).

In operation 2520, the server 2430 matches the accessed information to a beverage profile associated with a beverage, such as a smoothie. For example, the server 2430 may compare the user information to information associated with different ingredients, additives, and so on, and generate or identify one or more beverage profiles (e.g., mixtures of ingredients at certain quantities) that match or are otherwise associated with the user information. The server 2430 may then provide the one or more beverage profiles to the beverage machine 2420.

In operation 2530, the machine 2420 makes a beverage having the beverage profile that matched the user information. For example, using instructions (e.g., beverage profiles) received from the server 2430, the beverage making device 2424 of the beverage machine 2420 may select one or more beverage pods whose contents include ingredients that represent the beverage profile, and make the beverage using the contents of the pods. In some cases, the machine 2420 may order the beverage pods, and make the beverages once the pods are received and provided to the machine 2420.

Therefore, in some embodiments, the beverage profile determination server 2430 performs various processes for identifying, determining, recommending, and/or suggesting beverages, such as smoothies, to users based on various aspects associated with the users. The following sections describe, in greater detail, the different systems supported by the server 2430.

Examples of Customizing Beverages Based on User Activities

As described herein, in some embodiments, the systems and methods determine and/or generate customized beverage profiles and associated consumption programs based on user activities, such as current or predicted workout routines, and other exercises or activities. For example, the systems and methods may provide an automated beverage machine (e.g., smoothie maker or other beverage machine 2420, which makes smoothies from ingredients contained in smoothie pods) configured to receive information associated with a user's activities, such as workout routines, exercises, and so on.

In some embodiments, the beverage machine 2420 or other devices 2410, 2415 may collect information associated with a user's workout routine and/or physical activity, transmit the collected information to the server 2430 over the network 2425, and calculate, via the user activity system

2435, an estimated loss in calories, vitamins, carbohydrates, and so on, due to the activity/workout that was performed or scheduled to be performed.

The user activity system 2435 receives the values, such as the estimated deficiencies, matches the identified deficiencies with beverage available and desirable to the user (e.g., for weight loss users, beverages that maintain a net loss of calories), and sends a list of beverages that include beverage profiles associated with satisfying or meeting the user's deficiencies due to the completed, running, or planned activities. The machine 2420 and/or user device 2410 may display the list of beverages via an associated GUI, and make (or, order) a beverage selected by the user.

Figure 26:
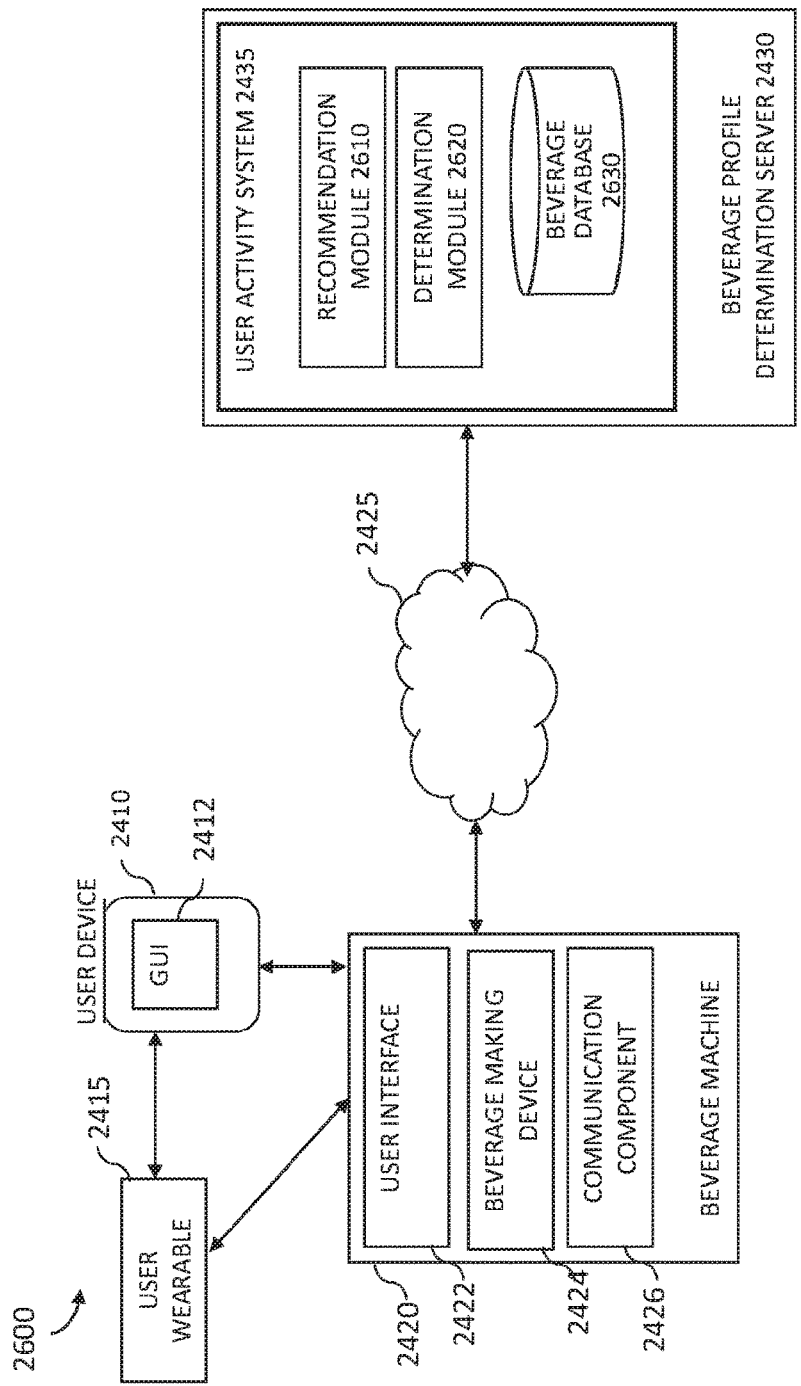
FIG. 26 is a block diagram illustrating a suitable computing environment for providing customized beverages to users based on activities of the users.

FIG. 26 is a block diagram illustrating a suitable computing environment 2600 for providing customized beverages to users based on activities of the users. As described herein, the user activity system 2435, located at or within the beverage profile determination server 2440, communicates over the network 2425 with the beverage machine 2420, the user device 2410, and/or one or more wearable or peripheral devices 2415 associated with the user.

For example, the wearable devices 2415 may include smart watches, activity monitors, heart rate monitors, peripheral devices, and so on. The measured activity levels and/or parameters may include steps taken by a user, a user's heart rate, distance walked or ran by the user, calories burned (or estimated to be burned), temperature of the user, physical characteristics during the activity, and so on. Also, in some cases, the device 2415, or another device, may be a connected workout machine (e.g., treadmill, elliptical, stationary bike, and so on) that communicates workout data for the user to the user device 2410, beverage machine 2420, and/or server 2430.

In addition, health data may be provided by or to the user device 2410, such as a smartphone, where a user is tracking his/her food intake, and determines suitable intake levels of calories, carbohydrates, fats, proteins, or other nutrients. The user may log caloric/food intake over the course of the day (type of food, quantity size, time of day, and so on), and the user, via the user device 2410, may upload or sent the logged data to the beverage machine 2420 or user activity system 2435, which performs utilizes the various information to determine recommendations associated with one or more beverages for consumption by the user.

In some embodiments, the beverage machine 2420 includes various operating software programs, located in the machine's memory, which may gather incoming data and transmit the data to various remote or networked systems, such as the user activity system 2435. As described herein, the external devices (e.g., a mobile phone 2410, wearable device 2415, smart workout machine, or other user device), captures and sends data associated with the user's workout or activity level to the machine 2420. The beverage machine 2420 may receive the data via a wireless connection (e.g., via network 2425) through the use of a plug-in device (e.g., USB stick, SD card, and so on), via direct communication channels (e.g., Bluetooth), and so on.

The beverage machine 2420 receives the data via the communication component or port 2426. When a user interacts with the machine 2420, via a user GUI provided by the user interface component 2422, the information is loaded, and if a suitable option presented by the user GUI screen is selected by the user, the data is transferred to the user activity system 2435, which generates beverage scores or other metrics. For example, the system 2435, via a determination module 2620, compares the beverage scores to beverages stored in a beverage database 2630, and then, via a recommendation module 2610, recommends beverages that match the beverage scores by sending information to the beverage machine 2420. The beverage machine 2420, via the GUI, displays user-selectable options for the user that represent the recommended beverages.

Figure 27:
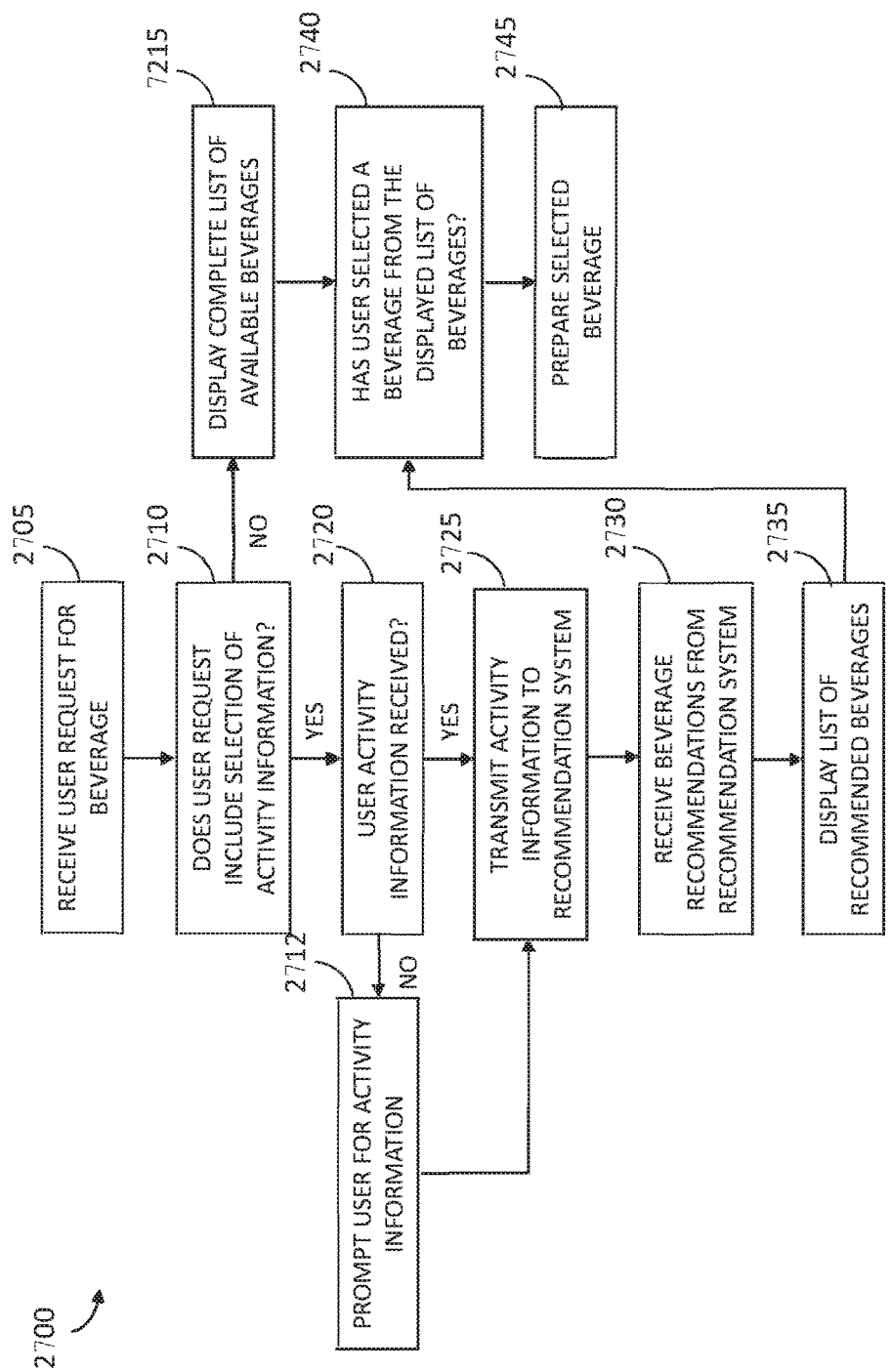
FIG. 27 is a flow diagram illustrating a method for preparing a beverage for a user based on activity information associated with the user.

Therefore, the user activity system 2435 performs various processes or methods when preparing beverages for a user based on the user's activities. FIG. 27 is a flow diagram illustrating a method 2700 for preparing a beverage for a user based on activity information associated with the user. Aspects of the method 2700 may be performed by the beverage machine 2420 and, accordingly, is described herein merely by way of reference thereto. It will be appreciated that the method 2700 may be performed on any suitable hardware.

In operation 2705, the machine 2420 receives a user request for a beverage, such as a smoothie or other drink. For example, the machine 2420 may receive a user selection of one or more options displayed by a GUI of the machine 2420 and/or the user device 2410.

In operation 2710, the machine 2420 determines whether the request includes a request or indication of user activity information. If the request does not include user activity information (or, an indication to utilize user activity information), the method 2700 proceeds to operation 2715, and the machine displays a complete list of beverages available to the user, such as beverages available to be made at that time by the machine 2420.

If the request does include a request or indication of user activity information, the method 2700 proceeds to operation 2720, and the machine 2420 determines whether user activity information has been received or provided by the user. If no user activity information has been received, the method 2700 proceeds to operation 2712, and the machine 2420, via the GUI, prompts the user to provide activity information (e.g., manually or via an associate device). If the user activity information has been received, the method 2700 proceeds to operation 2725, and the machine 2420 transmits the received or accessed user activity information to the recommendation module or system 2610 of the user activity system 2435.

In operation 2730, the machine 2420 receives one or more beverage recommendations from the recommendation module or system 2610, such as indications of beverages having beverage profile information that matched the user activity information. In operation 2735, the machine 2420 displays a list of the recommended beverages to the user, via the machine 2420 GUI.

In operation 2740, the machine 2420 determines that the user has selected one or more displayed beverages, either from a presented list of all available beverages (via operation 2715) and/or from a presented list of recommended beverages (via operation 2740), and, in operation 2745, prepares or makes the selected beverage using the beverage making device 2424 and one or more beverage pods that include ingredients matching the selected beverage.

Figure 28:
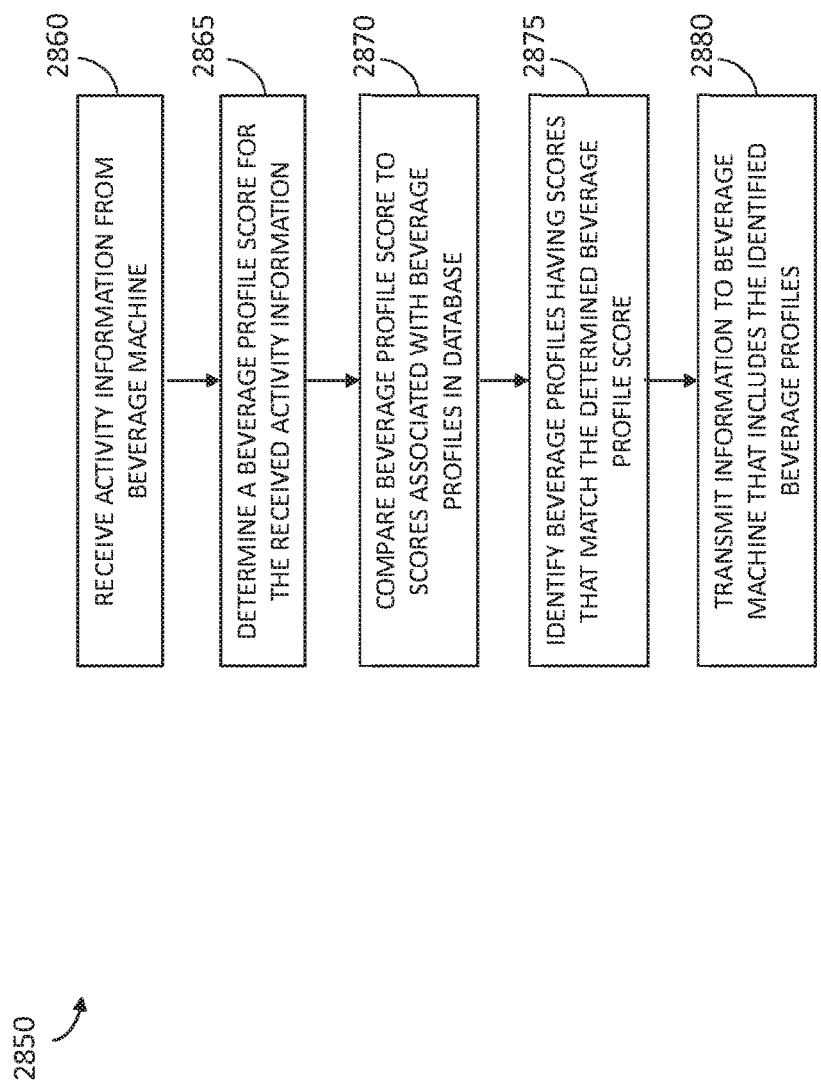
FIG. 28 is a flow diagram illustrating a method for determining a beverage recommendation that is based on user activity information.

As described herein, in some embodiments, the user activity system 2435 may perform various processes to compare and match user activity information to one or more beverage profiles that represent beverages to be made by the machine 2420 and consumed by the user. FIG. 28 is a flow diagram illustrating a method 2850 for determining a beverage recommendation that is based on user activity information. Aspects of the method 2850 may be performed by the determination module 2620 and, accordingly, is described herein merely by way of reference thereto. It will be appreciated that the method 2850 may be performed on any suitable hardware.

In operation 2860, the module 2620 receives activity information from the beverage machine 2420. For example, the user activity system 2435 may receive information from the machine 2420 that is associated with a user's completed, current, or future workout routine and/or physical activity, as described herein.

In operation 2865, the module 2620 determines a beverage profile score for the received activity information. For example, the module 2620 may determine the score by taking the total calories expended in the workout (e.g., 450 calories) and dividing it by 10 (or some other normalization factor), which provides a score of 45. Of course, the module 2620 may utilize other activity information and/or other scoring algorithms or rules (e.g., scores based on total calories, average heart rate, miles logged, steps walked, and so on) when scoring the activity information.

In operation 2870, the module 2620 compares the beverage profile score, or beverage score, to the scores associated with beverages profiles stored in the beverage database 2630. In some cases, the score may be based certain user goals, where there are selections of beverages useful in the user achieving their goals. Thus, in some embodiments, the module 2620 matches the score, along with the user's goals (e.g., loaded as part of the workout information), with values associated with beverage profiles stored by the beverage database 2630.

In some cases, the module 2620 receives user goal information (e.g., target weight information, fitness level information, and so on) from third party health/fitness programs, such as online program 2460. For example, the module 2620 may receive the goal information (e.g. via the network 2425 and/or via devices provided to the machine 2420) from a third party health practitioner (e.g., trainer, nurse, doctor, and so on) who can provide medically approved goals for the user.

In operation 2875, the module 2620 identifies one or more beverages having beverage profiles that match the determined beverage profile scores. Table 3 represents a data structure stored by the database 2630 that includes entries that relate a user goal (e.g., "lose weight") to beverage scores and beverage profiles.

TABLE 3

| Goal | Score Range | Beverage Profile |
| --- | --- | --- |
| Gain weight | 0-25 | Beverages #1 and #4 |
| | 26-50 | Beverages #6 and #2 |
| | 50+ | Beverages #8 and #12 |
| Maintain weight | 0-20 | Beverage #3 |
| | 21-44 | Beverages #5, #10, #11 |
| | 45+ | Beverages #15, #19, #20 |
| Lose weight | 0-22 | Beverages #7, #22 |
| | 23-35 | Beverage #16 |
| | 35+ | Beverages #13, #17, #18 |

For example, the module 2620, having received a beverage profile score of 25 and a user goal of maintain weight, searches Table 3 for matching beverage profiles, and identifies Beverages #5, #10, and #11 as matching the score.

Figure 29:
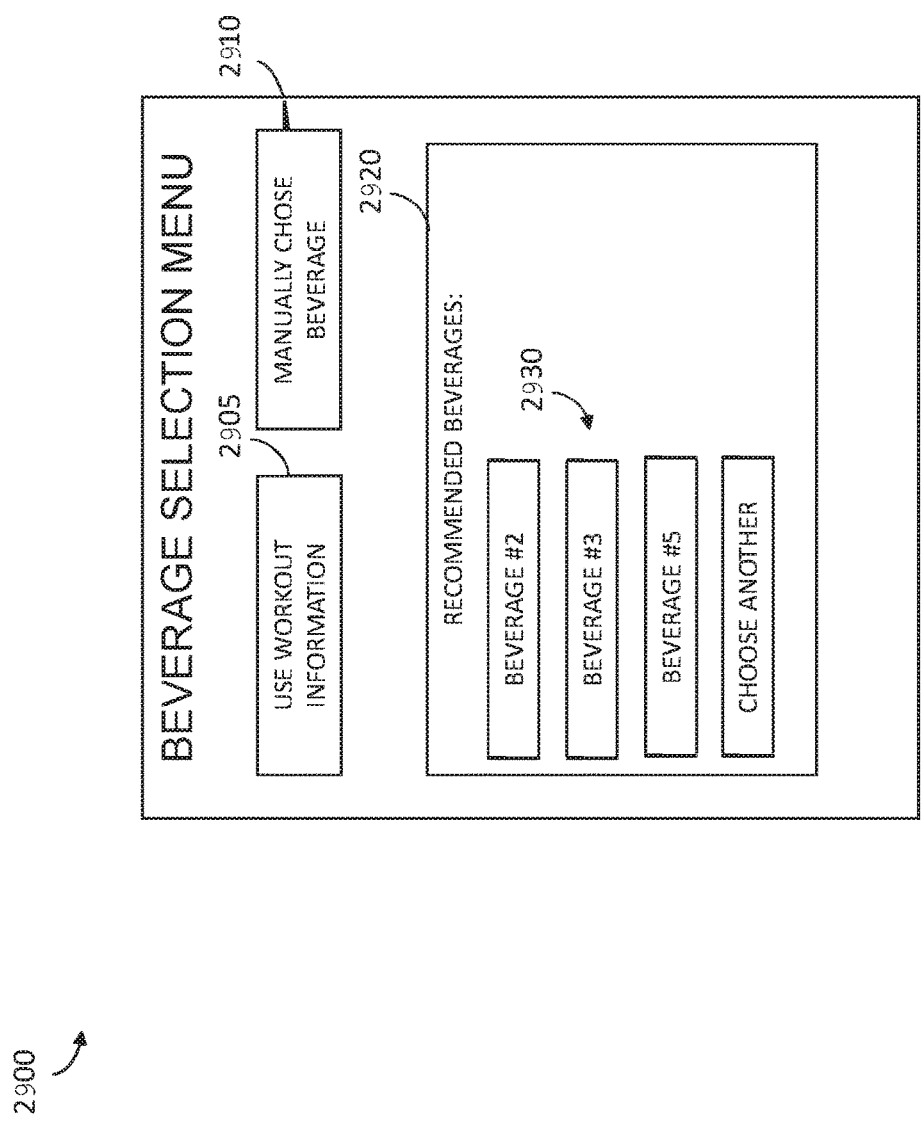
FIG. 29 is a display diagram illustrating a user interface that displays recommended beverages to a user based on activities of the user.

In operation 2880, the module transmits information that identifies the recommended (e.g., matching) beverage profiles to the beverage machine 2420, which presents the information to the user. FIG. 29 is a display diagram illustrating a user interface 2900 that displays recommended beverages to a user based on activities of the user.

The user interface 2900 presents various states of interaction with a user. A user first requests to make a beverage, and selects a manual option 2910 to manually choose a beverage from a list or menu, or a user activity option 2905 to use their workout information/data, such as data gathered by the user device 2410 or device 2415. In some cases, the user interface may include elements than enable a user to directly input their daily health data (e.g., activity, desired goals, and so on), and the interface 2900 may include elements that facilitate the user to input both activity data and specified goals. For example, the user interface 2900 may receive the information via a questionnaire type interaction with the user, where the user answers questions regarding goals and activities posed by the machine 2420, and/or the user may voluntarily input information that represents regards the user's goals, activities, and other information.

As described herein, when the user selects the manual option 2920, the machine 2420 presents a list of some or all available beverages. However, when the user selects the user activity option 2905, the machine 2420 presents a list 2920 of recommended beverages, based upon user activity information. The user may select one or more of the recommended beverages 2930, and the machine 2420, in response to the selections, makes (or, orders), a beverage, such as a smoothie for the user. As described herein, the machine may make a smoothie using a smoothie pod of ingredients that match the beverage profile associated with the selected beverage.

Thus, in some embodiments, the systems and methods collect information associated with a user's workout routine or physical activity via an automated beverage machine, where the automated beverage machine makes beverages from beverage pods provided to the automated beverage machine, determines a workout score based on the collected information, matches the workout score to one or more beverage profiles associated with beverages to be consumed by the user, and makes, at the automated beverage machine, a beverage having ingredients based on the one or more beverage profiles.

Therefore, in some embodiments, the systems and methods enable a user to provide workout and/or health goal information to an automated beverage machine (e.g., beverage machine 2420), which identifies and makes a pod-based beverage (e.g., smoothie from a smoothie pod) based on the provided information.

Examples of Customizing Beverages Based on User Sleep Activities

The systems and methods described herein, in some embodiments, determine and/or generate customized beverage profiles, and make associated beverages, for users based on characteristics of the user's sleep activities, patterns, habits, and/or cycles. The systems and methods utilize sleep and activity data measured by a user's wearable device (e.g., device 2415) to determine when and how well the user sleeps. The systems and methods combine the sleep data with usage data (e.g., beverage consumption data), and determine recommendations for the user regarding the types (e.g., ingredient profiles) and timing (e.g., when to consume) of smoothies he/she should consume to increase his/her quality of sleep, among other things.

For example, the systems and methods may attempt to improve or modify a user's sleep (or, quality of sleep), by determining a user's current or historical quality of sleep from sleep and activity data obtained from a user's wearable device or other monitoring device, combining or comparing the determined data with usage data associated with the user's consumption of various smoothies, and determining recommendations for the user about the types and timing of smoothies and other beverages to consume to improve the quality of sleep. The system and methods may then tracks changes in the user's quality of sleep based on the recommendations to provide more accurate recommendations for the specific user and/or a population of other similar users.

Figure 30:
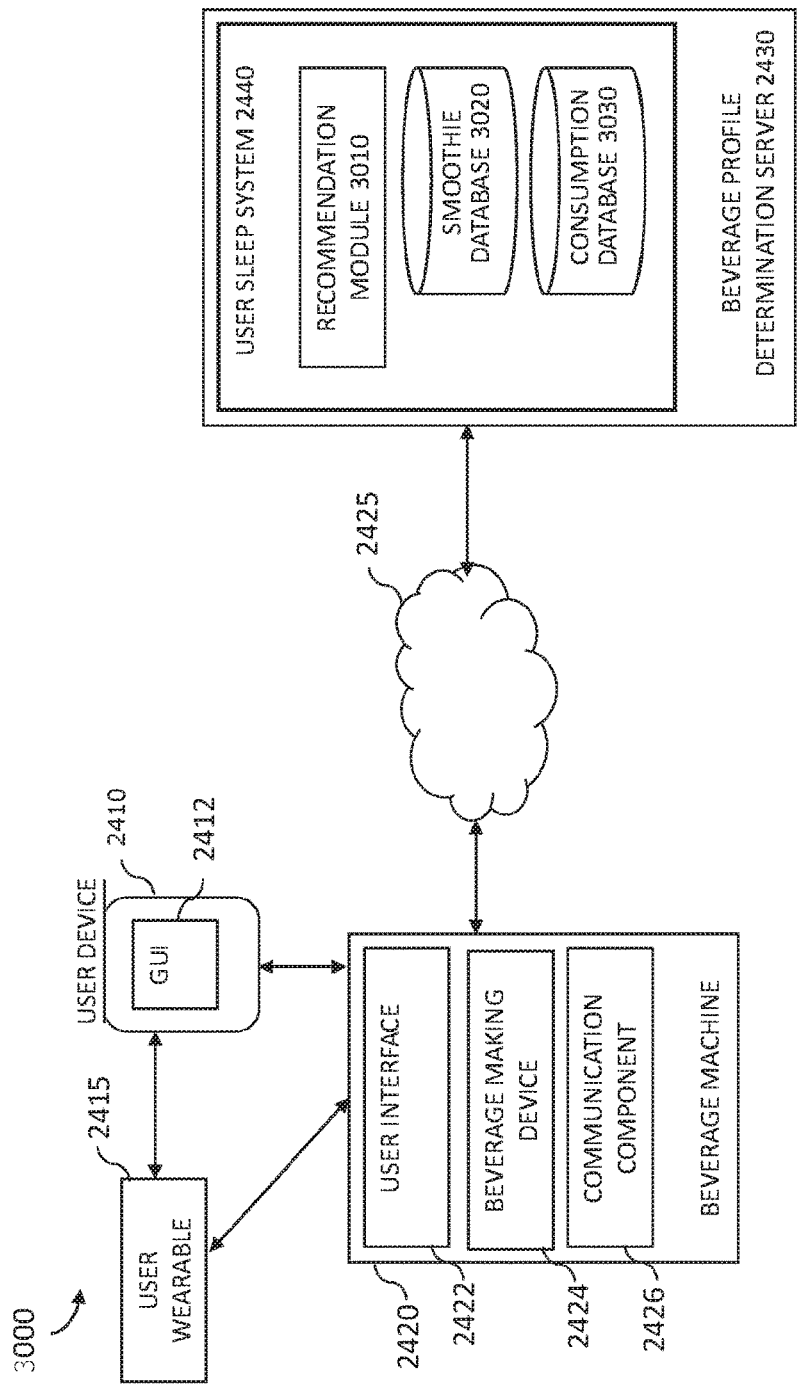
FIG. 30 is a block diagram illustrating a suitable computing environment for providing customized beverages to users based on sleep activities of the users.

FIG. 30 is a block diagram illustrating a suitable computing environment 3000 for providing customized beverages to users based on sleep activities of the users. As described herein, a wearable device 2410 (e.g., a Withings, FitBit device, or other device configured to monitor a user's sleep activities) may capture data associated with a user's sleep activities, as well as other non-sleep data (e.g., temperature, heart rate, and so on). The systems and methods may combine the user's sleep data with the user's smoothie consumption history, determine recommendations to be made to the user about the types and timing of smoothies that can increase the quality of their sleep.

The computing environment 3000 includes the beverage profile determination server 2430, which includes the user sleep system 2440. The user sleep system 2440 includes various components or modules, such as a recommendation module 3010 configured to determine one or more beverages having beverage profiles that match user sleep activity information. Further, the user sleep system 2440 includes a smoothie database 3020, which stores information that includes the ingredients of all available beverage pods (e.g., beverage pods at the machine and/or to be ordered and provided to the machine), such as smoothie pods, for the beverage machine 2420, and a consumption database 3030, which stores user usage or beverage consumption data as well as user sleep activity data.

As an example, when a user's wearable device 2415 comes within wireless communications range of the beverage machine 2420, the device 2415 transfers the user's sleep and activity data, which is then relayed by the beverage machine 2420 to the consumption database 3030 of the user sleep system 2440.

When the user goes to get a smoothie after a certain time (e.g., after 5 μm or so, as the user may not want a relaxation smoothie when they are getting up to go to work), the recommendation module 3010 may compare the user's sleep on any given day to their average night's sleep. For example, the user's sleep activity may be measured with respect to both quantity and quality to determine a current or prior level of sleep (e.g., poor, ok, average, good, short, long, and so on), via the wearable device 2415. Using the information, the system 2440 determines a recommendation for a beverage to be provided to the users, and sends the recommendation over the network 2425 to the beverage machine 2420, which makes the beverage for the user.

Figure 31:
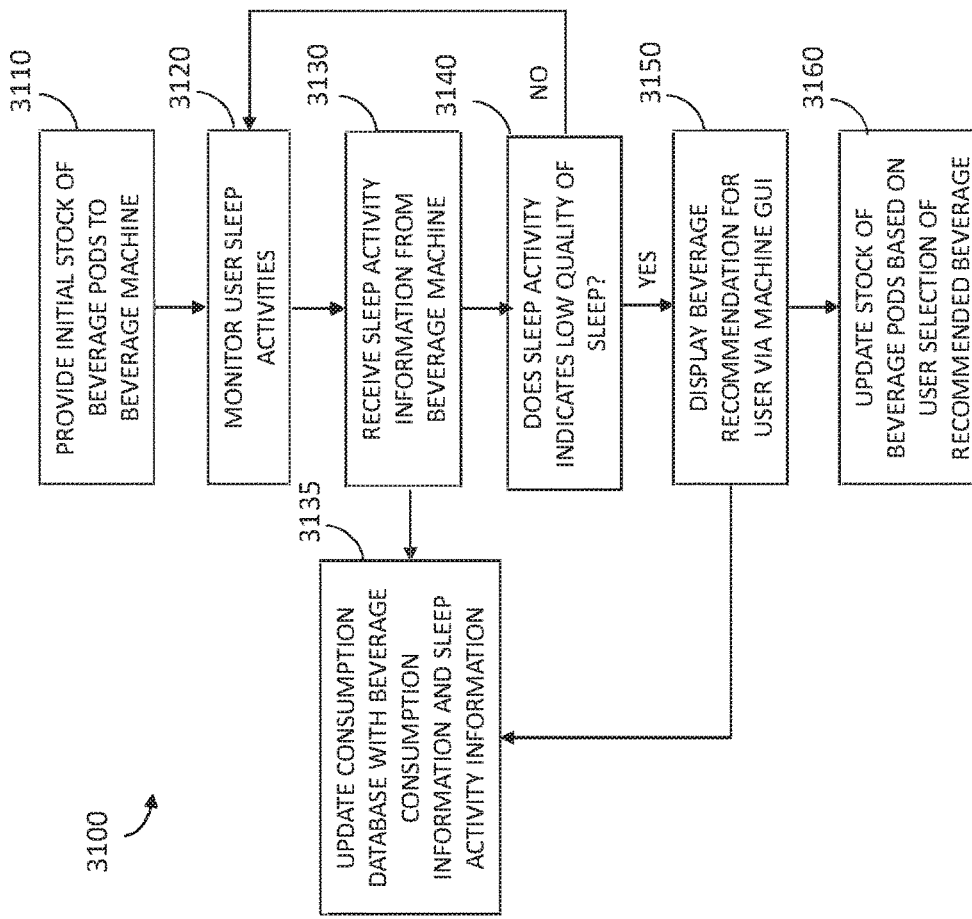
FIG. 31 is a flow diagram illustrating a method for determining a beverage recommendation for a user based on sleep information associated with the user.

Therefore, the sleep activity system 2440, via the recommendation module 3010, performs various processes, operations, or methods when determining beverages to recommend to users based on their sleep activity information. FIG. 31 is a flow diagram illustrating a method 3100 for determining a beverage recommendation for a user based on sleep information associated with the user. Aspects of the method 3100 may be performed by the user sleep system 2440 and, accordingly, is described herein merely by way of reference thereto. It will be appreciated that the method 3100 may be performed on any suitable hardware.

In operation 3110, the system 2440 provides an initial stock of beverage pods to the beverage machine 2420. For example, a user associated with the machine 2420 may receive an initial order of various different beverage pods for popular or initially targeted beverages, and provide them to the beverage machine 2420. In some cases, various analysis systems may utilize data within the consumption database 3030 to determine supplements that are effective in enhancing sleep quality, sleep quantity, and so on. For example, these systems may determine initial orders of smoothie pods based on determinations of a large user population, modifying the initial orders based on the demographics of users, the specific user, and their wearable devices.

In operation 3120, various devices monitor the user's sleep activities. For example, the wearable device 2415 may capture data associated with a user's sleep cycle activity, such as time periods of deep sleep, time periods of light sleep, time periods of REM sleep, time periods of wakefulness, a total sleep time, user movement data, non-sleep data, and so on.

In operation 3130, the system 2440 receives or otherwise accesses the sleep activity information from the beverage machine 2420 and/or directly from the wearable device 2415 and/or the user device 2410. For example, the system 2440 may receive the sleep activity information from a most recent night's sleep, as well as any usage or beverage consumption data for the user, and store, in operation 3135, the information in the consumption database 3030.

In operation 3140, the system 2440 determines whether the sleep activity information indicates a low or sub-optimal quality of sleep for the user. For example, the system 2440 may determine a time period of deep sleep or REM sleep is below a minimum time period associated with good sleep, and/or may determine the overall sleep quality for the previous night's sleep is below an average sleep quality for the user, among other determinations.

When the sleep quality does not indicate a low quality of sleep, the method 3100 proceeds back to operation 3120, and the system 2440 continues to monitor the user's sleep activity, else the method proceeds to operation 3150. In operation 3150, the system 2440 determines and causes the machine 2420 to display one or more beverage recommendations for the user. For example, the system 2440 may utilize information stored in the consumption database 3030 to determine one or more beverages to recommend to the user.

The following table (Table 4) illustrates the various data structures stored in the database 3030, via which the system 2440 identified beverages to recommend to a user.

TABLE 4

| Date | Sleep Quality | Ingredients | Volume | Time |
| --- | --- | --- | --- | --- |
| Jan. 1, 2016 | Poor | Melatonin, ABC | 8 oz. | 7:15 |
| Jan. 2, 2016 | OK | Chamomile, ABC | 8 oz. | 6:15 |
| Jan. 3, 2016 | OK | ABC | 8 oz. | 7:15 |
| Jan. 4, 2016 | OK | DEF | 8 oz. | 8:15 |
| Jan. 5, 2016 | Good | Melatonin, DEF | 12 oz. | 7:15 |

Thus, the system 2440 may utilize the information stored by the table to identify and/or modify beverage profiles based on the user's sleep activities or quality. For example, the table indicates that the user experiences a good sleep quality (e.g., sufficient amounts of REM sleep) after consuming a smoothie with ingredients DEF.

In operation 3160, the machine 2420 updates a stock of beverage pods based on the recommended beverage and/or based on a user selection of the recommended beverage. Thus, in some cases, the machine 2420 tracks and/or monitors consumption of beverages by the user to maintain sufficient stock of beverage pods for making recommended beverages.

For example, an initial stock of sleep supplement smoothies or other beverages are provided to the machine 2420, and a wait period counter is set to initialize to a 4 day wait period. Next, the activity/sleep monitor (e.g., device 2415) communicates when within wireless range of the beverage machine 2420, which triggers a download from the wearable device 2415 to the beverage machine 2420 of user sleep data.

As described herein, the user sleep system 2440 determines a quality of the user's sleep (e.g., is poor for >2 days or some other threshold), and when the quality is low, the system 2440, within the 4 day wait period (initialization period) and if causes the machine 2420 to present a suggestion to take a sleep supplement or relaxing beverage. The machine 2420 then starts a period for 4 days and subtracts one sleep supplement smoothie from the stock, updating the number of pods in stock within the machine 2420. In some cases, when the stock of pods is less than 2 (or below a defined threshold number), the machine 2420 may suggest other beverages, and initiates an order/reorder routine to replenish the stock of beverage pods.

Figure 32:
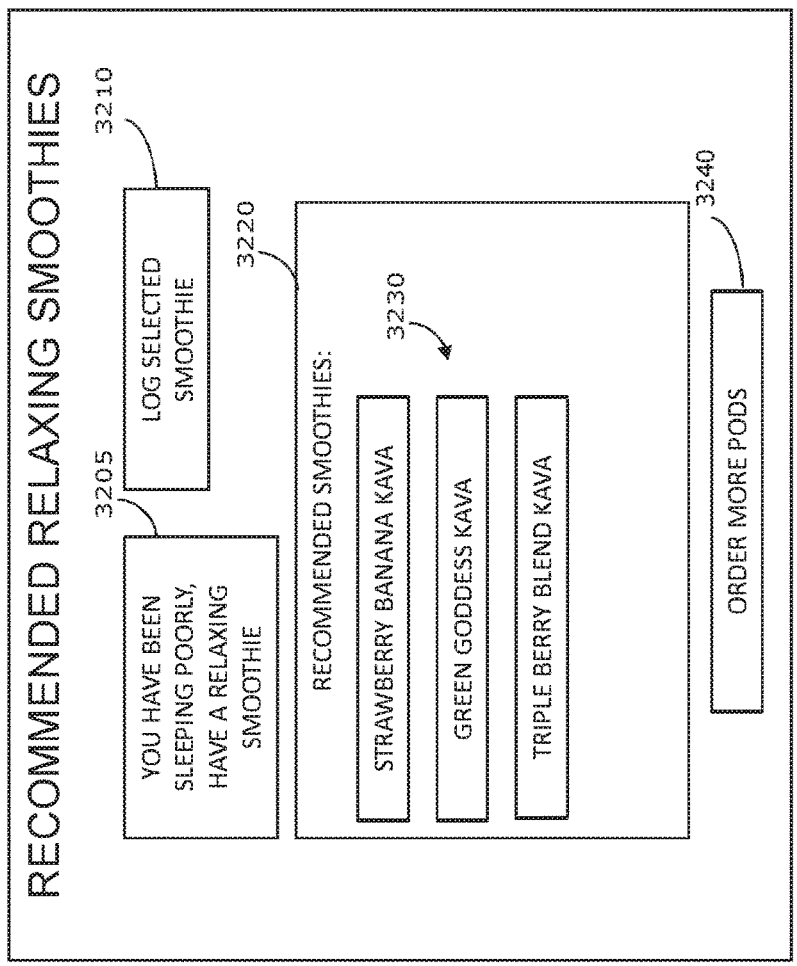
FIG. 32 is a display diagram illustrating a user interface that displays recommended beverages to a user based on sleep information of the user.

As described herein, the beverage machine 2420 presents the recommended smoothies and other beverages to the user via a GUI of the machine 2420. FIG. 32 is a display diagram illustrating a user interface 3200 that displays recommended beverages to a user based on sleep information of the user.

The interface 3200 displays various interface elements or buttons, including user-selectable display elements 3220 representing smoothies 3230 recommended by the system 2440. In some cases, the interface 3200 provides a user-selectable option to request a smoothie 3205, log or record consumption of a smoothie 3210, and or order a smoothie or smoothie pods 3240. In some cases, the user interface may mark recommended beverages as being "in stock" when the inventory database indicates the user has that pod available, or "order," which will automatically send an order to a server to order additional smoothie pods. The interface 3200 may also include other display and input elements, such as elements informing the user of their monitored sleep activities, elements that receive user input regarding the consumption of smoothies, and so on.

The beverage machine 2420, therefore, may include an input component that receives a request from a user to make a beverage (via the interface 3200, a communication component that receives information from a wearable device associated with the user that identifies sleep activity characteristics of the user (via wearable device 2415), and a beverage making component that makes a beverage having a beverage profile that is associated with the sleep activity characteristics of the user (e.g., determined via the user sleep system 2440 located at the server 2430 and/or within the machine 2420).

Thus, in some embodiments, the systems and methods may receive input from a wearable device of a user that identifies sleep activity characteristics of the user, compare the sleep activity characteristics of the user with usage data associated with the user's previous consumption of smoothies and received from a smoothie machine that prepared the smoothies, and determine a smoothie to recommend to the user that is based on the comparison.

Examples of Customizing Beverages Based on User Mental Acuity

The systems and methods described herein, in some embodiments, determine and/or generate customized beverage profiles for users based on the users' measured mental acuity. The systems and methods utilize or provide games or tests that measure mental acuity, in some cases delivered before and after the user consumes a smoothie, to identify those ingredients that yield increases in mental acuity for the specific user.

For example, the systems and methods may measure a user's mental acuity each time the user obtains a beverage, and presents tests, games, and so on, via the user's mobile device or via a user interface of the beverage machine 2420, which provides cognitive assessment systems with data points associated with the user's mental acuity. The systems and methods identify a state of the user's mental acuity in certain contexts, and generates or suggests a smoothie program (types and/or timing) of smoothies (and associated supplements) predicted to be of benefit to the user.

Figure 33:
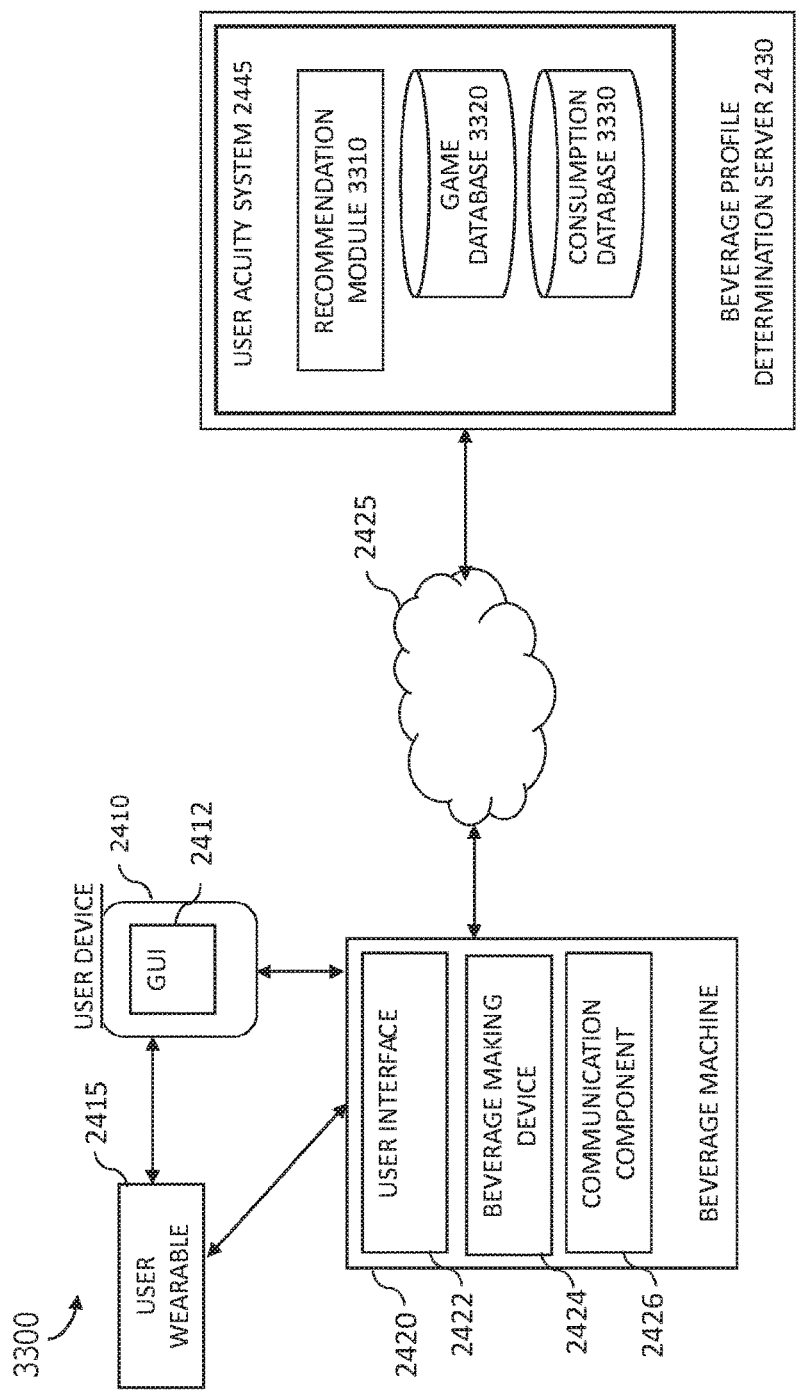
FIG. 33 is a block diagram illustrating a suitable computing environment for providing customized beverages to users based on mental acuity information for the users.

FIG. 33 is a block diagram illustrating a suitable computing environment 3300 for providing customized beverages to users based on mental acuity information for the users. As described herein, the user acuity system 2445 includes various components, modules, or systems for determining a current mental acuity or sharpness of a user, and determining smoothies and other beverages (or, supplements to be added to base smoothies) to recommended to the user for consumption.

For example, the system 2445 includes a recommendation module 3310, which receives information associated with the user's mental acuity, such as a score obtained while playing an online or virtual game, and identifies beverages having certain beverage profiles, and/or supplements, to recommended to the user. The system stores various user information (e.g., previous scores, beverage consumption data, and so on) in a consumption database 3330, and stores various games virtual games or tests in a game database 3320.

In some cases, when the user mobile device 2410 triggers, based upon the user profile (not shown), a game the user will interact with, the user acuity system 2445 may retrieve and present or display a game from the game database 3320 to the user. Once the user plays the game, the recommendation module 3310 receives or accesses the results or outcomes (e.g., scores) of the game play to determine whether a smoothie with stimulants or supplements should be recommended or suggested to the user.

Once the user has taken the stimulants or supplements, the user may play another game. For example, the system 3310 may receive an indication from the user or from the beverage machine 2420 that the user has consumed a recommended smoothie (e.g., the beverage machine 2420 prepared the smoothie for the user). The system 2445 determines whether the recommended smoothie (with stimulants or supplements) improved results based on a comparison of the scores of the games played before and after consumption of the smoothie. The system may store the results of the comparison in order to provide more accurate or targeted recommendations to the user or other users regarding the consumption of certain ingredients, stimulants, or supplements.

Thus, the system 2445 may identify optimal or helpful smoothie stimulants or supplements based on user performances during presented games and other activities. The system 2445, via various channels, such as via advertising services, nutritional and wellness programs, social media, and so on, may then promote or recommend the identified ingredients to others. Further, in some embodiments, the system 2445 facilitates ordering and reordering of the smoothie stimulants or supplements targeted to the user.

Therefore, the user acuity system 2445 may perform various processes, operations, or methods when determining smoothie recommendations for users based on their performance in playing certain games, tests, or other mental activities. FIG. 34 is a flow diagram illustrating a method 3400 for determining a beverage recommendation based on user performance on one or more acuity tests before and after consuming a customized beverage. Aspects of the method 3400 may be performed by the user acuity system 2445 and, accordingly, is described herein merely by way of reference thereto. It will be appreciated that the method 3400 may be performed on any suitable hardware.

In operation 3410, the system 2445, via one or more user interfaces, causes display of a first mental acuity test or virtual game. For example, the system 2445 may send a virtual game stored in the game database 3320 to the mobile device 2410 or beverage machine 2420 for display to a user via associated user interfaces. In some cases, the system 2445 may utilize one or more games provided by online or third party game providers, and cause displays or interaction between the online game and the user via the associated user interfaces.

In operation 3420, the system 2445 determines whether a score associated with the user playing the game or test indicates a beverage recommendation. For example, the system may compare the score with an expected score, a minimum score, a maximum score, and so on, and determine whether the current mental acuity of the user is below, above, or within a threshold associated with recommending beverages to the user to enhance or improved the user's current or temporal acuity.

When the system 2445 determines the user's score does not indicate a recommendation (e.g., the score is a maximum or high score), the method 3400 proceeds to operation 3425, and the system polls the user and other users to take additional or later tests or play games. When the system 2445 determines the user's score does indicate a recommendation (e.g., the score is low or within a certain low performance threshold), the method 3400 proceeds to operation 3430, and the system 2445 randomly selects a beverage profile for the user.

After receiving an indication that the user consumed a smoothie or other beverage, the system 2445, at operation 3440, displays a second, or additional mental acuity test or game to be played by the user. Once the user plays the game, the system 2445, in operation 3450, determines whether the user's score indicates a changed mental acuity (e.g., the score is above a threshold, or the difference between scores exceeds a threshold).

When the score exceeds the threshold, the method 3400 proceeds to operation 3460, and the system 2445 updates the consumption database 3330 with the results of the comparison. Therefore, the system 2445 obtains a data point for the user that indicates the smoothie and/or its contents consumed by the user improved or modified the user's mental acuity. Table 5 depicts a data structure that represents that data stored in the consumption database 3330.

TABLE 5

| Pre Drink Score | Smoothie Stimulant | Keep Recommendation Delta >20 |
|---|---|---|
| 40-55 | Caffeine Maca . . . | |
| 56-65 | Ginseng Cayenne . . . | Yes |
| 66-75 | B12 Coconut Oil . . . | |
| 76-84 | Green Tea Guarana . . . | |
| 84-100 | None | |

| Date | Pre drink test score | Recommend >=85 | Smoothie Stimulant | Post drink test score | Delta | Keep Recommendation >=20 |
|---|---|---|---|---|---|---|
| Jan. 1, 2016 | 85 | No | N/A | N/A | N/A | N/A |
| Jan. 2, 2016 | 75 | Yes | B12 | 70 | 5 | no |
| Jan. 3, 2016 | 55 | Yes | Caffeine | 85 | 30 | Yes |
| Jan. 4, 2016 | 55 | Yes | Caffeine | 95 | 40 | Yes |
| Jan. 5, 2016 | 85 | No | N/A | 75 | N/A | N/A |
| Jan. 6, 2016 | 65 | Yes | Ginseng | 65 | 0 | No |

As shown in Table 5, the data structures log the results of a pre-test game, and if the score is greater than 85, the system 2445 does not suggest smoothie stimulants or supplements. When the scores range between 40-84, the system 2445 recommends various smoothie stimulants or supplements, and if second, or subsequent game results show improvement (e.g., with a score difference of 20), the system 2445 logs the improvement data for future recommendations.

As described herein, the user acuity system 2445 may present various games or other displayed information when attempting to ascertain a current or temporal mental acuity, sharpness, or alertness for a user.

Figure 35A:
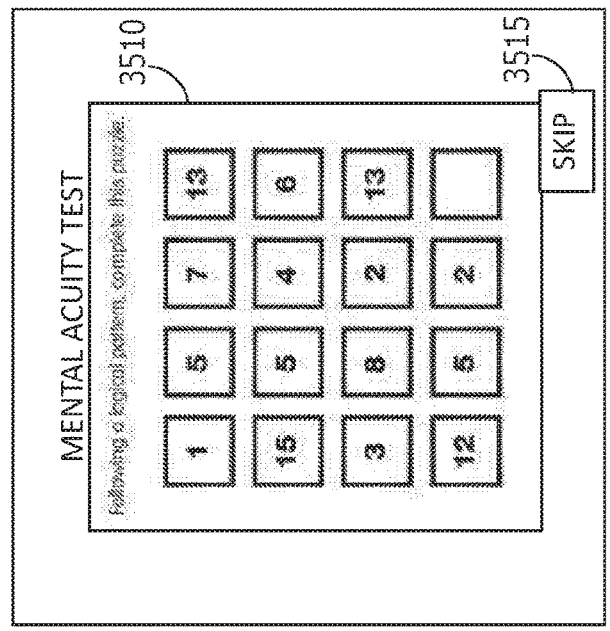
FIG. 35A is a display diagram illustrating a user interface that present a mental acuity test for a user.

FIG. 35A is a display diagram illustrating a user interface 3500 that present a mental acuity test 3510 for a user. As depicted, the example game or test 3510 prompts the user to play a logic puzzle and repeat or complete a pattern. The user may play the game 3510 via the interface 3500, or select an option 3515 to skip the presented game 3510 and play a different game.

Of course, the system may display a variety of different games to test a user's mental acuity, include puzzle games, first person games, journey games, tests, quizzes, and so on. In some cases, the games database 3320, or a third-party provider of the games, may advertise certain smoothies within the games, and/or develop specific games for certain smoothie types. In addition, other scored games or activities may be utilized when recommending smoothies. For example, the system 2445 may receive a student's test scores, and recommend smoothies or supplements based on the test scores or based on their online gaming results.

Figure 35B:
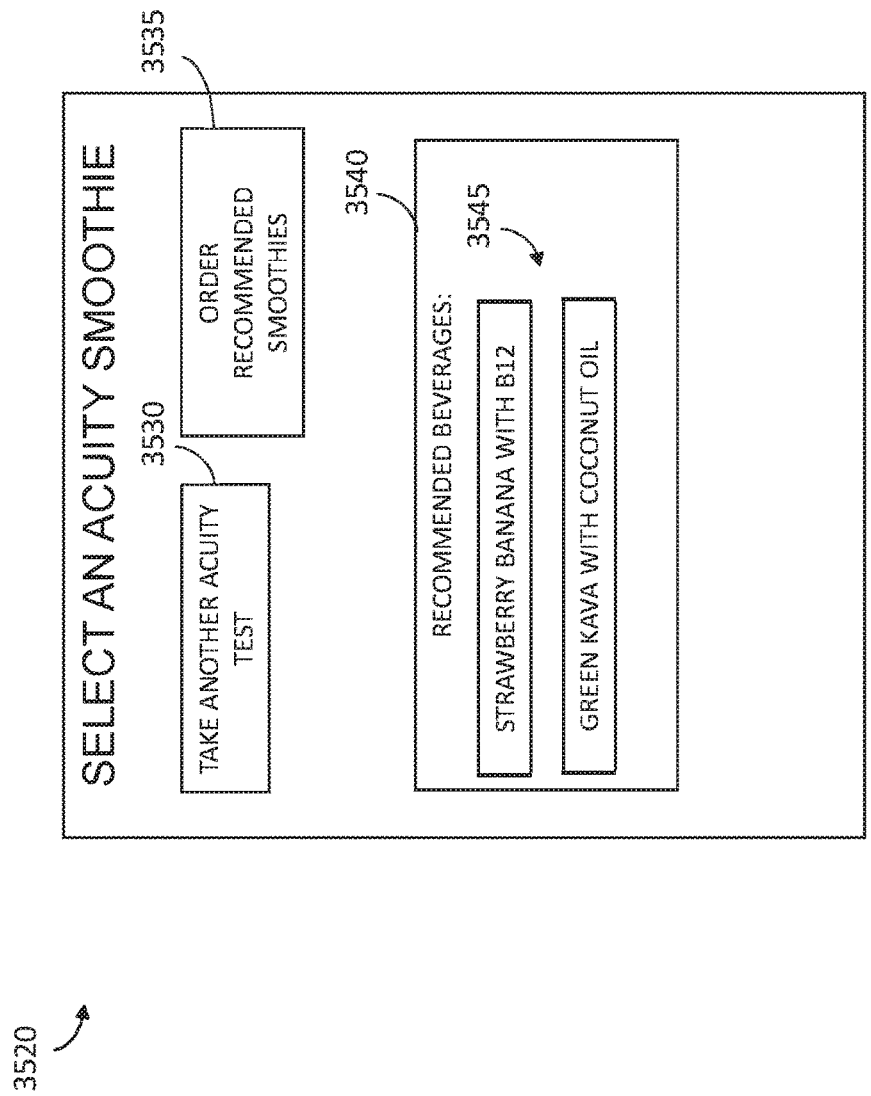
FIG. 35B is a display diagram illustrating a user interface that displays recommended beverages to a user based on test performance for a user.

Once the game is played, the system 2445, via the user interface, presents the user with recommended beverages for consumption. FIG. 35B is a display diagram 3520 illustrating a user interface that displays recommended beverages to a user based on test performance for a user. The GUI 3520 may present recommended smoothies, amounts of stimulants, frequencies of smoothie or supplements or doses, and so on, based on results of the user playing the game or games. The interface 3520 may include user-selectable options to take another acuity test 3530, order one or more recommended smoothies 3535, as well as present recommended beverages 3540 with options 3545 to make the beverages using the beverage machine 2420.

For example, a smoothie machine may include an input component that presents, via a user interface of the smoothie machine, a virtual game to be played by a user, a recommendation component that recommends one or more smoothies to make for the user based upon a result associated with the user playing the virtual game, and a beverage making component that makes the one or more smoothies (via smoothie pods).

Thus, in some embodiments, the systems and methods may present a game to a user via a mobile device associated with the user, receive a score associated with the user playing the presented game, and identify a smoothie to recommend to the user that is based on the received score.

Further, the systems and methods may present a second game to the user via the mobile device, receive a score associated with the user playing the presented second game, determine the score associated with the user playing the presented second game is greater than the score associated with the user playing the presented game, and recommend the smoothie to other users.

Examples of Customizing Beverages to User Wellness Programs

The systems and methods described herein, in some embodiments, determine and/or generate customized beverage profiles for users of wellness and other online health programs, via integrated communications between services and supporting servers.

For example, the systems and methods may provide a Software as a service (SaaS) application programming interface (API) to various online health, weight loss and/or wellness programs, facilitating exchanges of information between a smoothie recommendation program (e.g., a system that orders smoothie pods and/or recommends or makes smoothies for users) and the various online programs. The online programs may be various partner services, such as diet partners, exercise partners, ingredient or nutrition partners, blender device partners, medical partners, doctor network partners (e.g., partner systems develop having their own algorithms) to integrate their software programs (services) and data through various APIs to the smoothie recommendation program.

Thus, the systems and methods provide users, members, and/or subscribers of online partnership programs to obtain smoothie pods (for various smoothies and other beverages) and/or made smoothies and other beverages from the cloud-based service (e.g., "Smoothie as a Service"). The service facilitates the exchange of data between the smoothie recommendation program and the online partner programs (e.g., wellness programs, exercise and health programs, nutrition programs, diet and weight loss programs, and so on). In some cases, the systems and methods may provide a subscription system to tie in with WeightWatchers® or NutriSystem® or other partners, allowing a user to get a smoothie pod or beverage integrated with or based on the partnership's programs or services.

For example, a person on a long term weight loss program (e.g., a program that restricts the person to a certain number of calories per day) will receive smoothies that have low calorie, high protein ingredient or nutrition profiles (and possibly energy and metabolisms boosters), whereas a person looking to get in shape will receive smoothies that have high protein enhancement ingredient or nutrition profiles, as instructed by the health or diet programs to which they subscribe (e.g., a smoothie program, provided by a smoothie making machine, may receive instructions via a SaaS API provided to the online programs).

Thus, the systems and methods integrate the automated provision of smoothies (e.g., based on customized smoothie pods) and a weight loss or other user health partner. In some cases, the products (e.g., pods or made beverages) may be white labeled through the partners so that product kits are shipped with both the partners' weight loss program branding and the smoothie pods' branding, with ordering and provision of pods being performed by the smoothie program or recommendation server.

Figure 36:
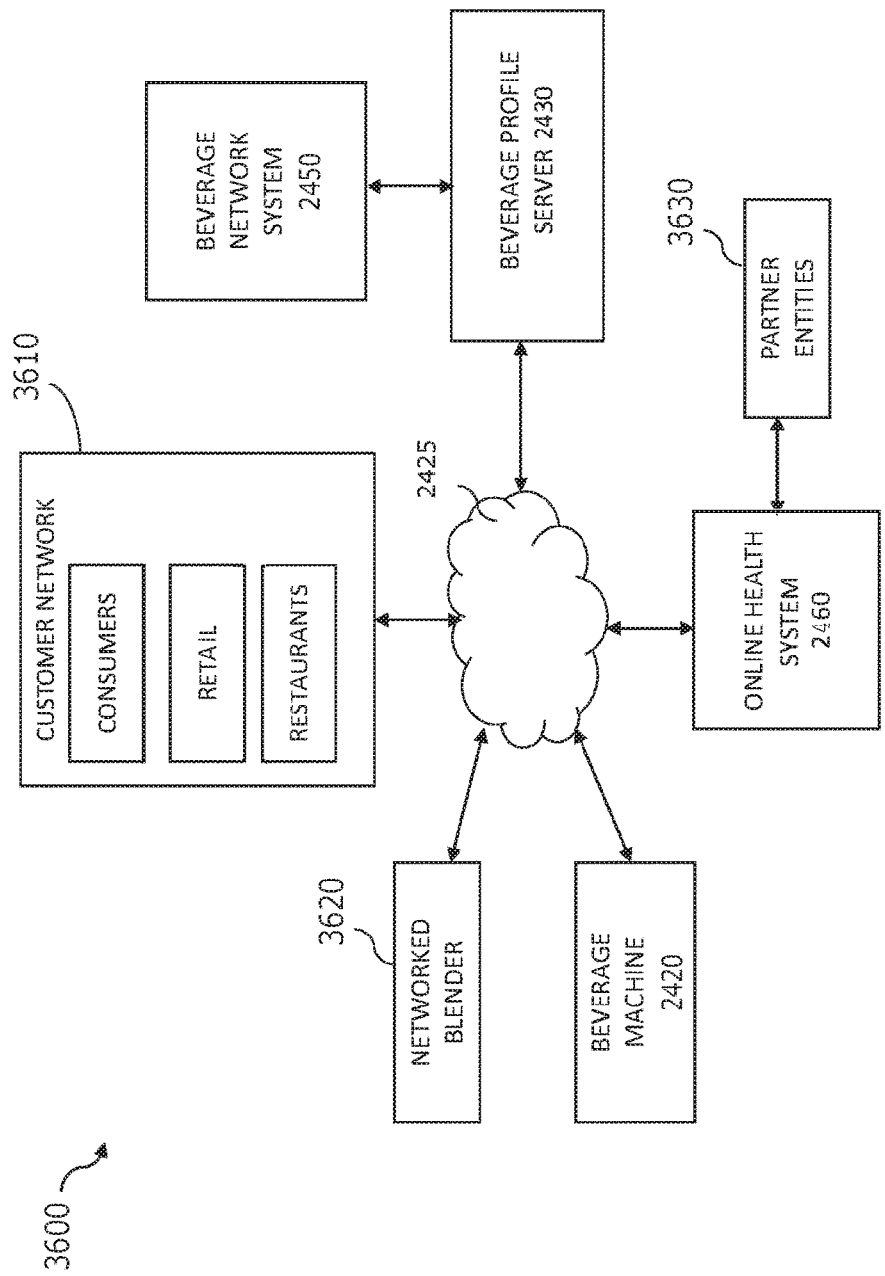
FIG. 36 is a block diagram illustrating a suitable computing environment for providing customized beverages to users of online wellness programs.

FIG. 36 is a block diagram illustrating a suitable computing environment 3600 for providing customized beverages to users of online wellness programs. Similar to the other computing environments described herein, the beverage profile server 2430 communicates over the network 2425 with various devices or systems, such as the beverage machine 2420 and the online health system 2460. Additionally, the server 2430 may provide access to various recommendation systems (as described herein) via the beverage network system, which provides APIs to the online health system and other systems requesting information (e.g., beverage recommendation information) from the beverage profile server 2430.

For example, a customer network 3610 of sites, such as consumers associated with computing devices, retail entities, and/or restaurants and other service provider entities (e.g., cafes, gyms, snack bars, and so on), may access the systems of the server 2430 via APIs or other SaaS services provided by the beverage network system 2450. As another example, a networked blender 3620, refrigerator, or other smoothie making entity or device may communicate with the server 2430 over the network 2425 via published APIs. Further, as described herein, the online health system 2460 may be part of or associated with partner entities, such as online diet or health programs.

Further, the system 2450 may include ordering services via an ordering database, weight analysis services via a weight database, exercise services via an exercise database, and other health services (e.g., special medical analyses), and may issue reports, alerts and other dashboard indicators or displays, depending on the needs of the users or partner systems.

Figure 37:
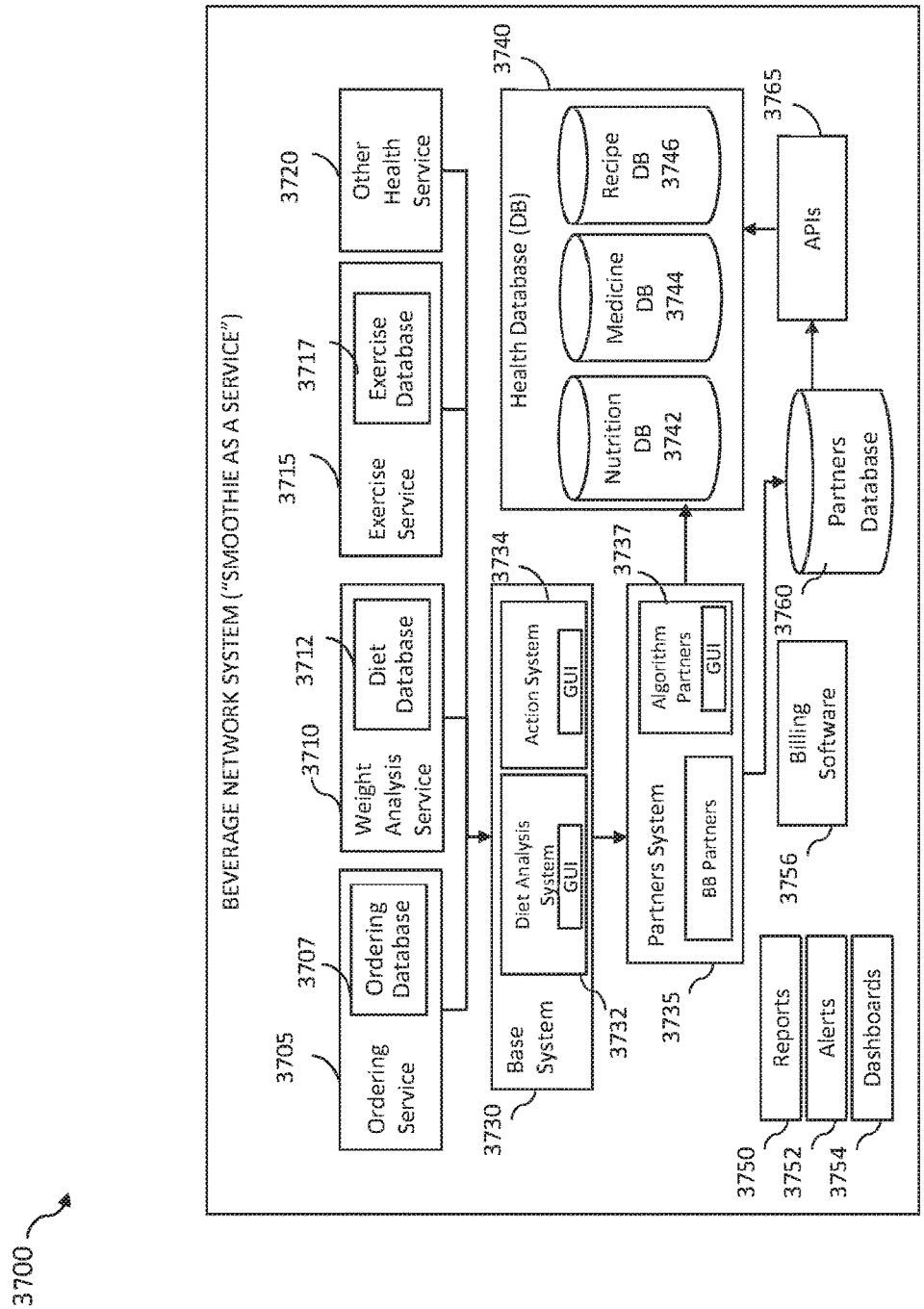
FIG. 37 is a block diagram illustrating components of a beverage network system that interacts online wellness programs.

FIG. 37 illustrates various components of a beverage network system 3700 that interacts online wellness programs. The system 3700, which may be part of the beverage network system 2450 or beverage profile server 2430, includes various components or modules configured to provide recommended beverages to users of online systems.

For example, the system 3700 includes an ordering service 3705 and associated ordering database 3707 configured to order stock of beverage pods for users and other entities, a weight analysis service 3710 and associated diet database 3712 that stores information associated with analyzing weight loss goals for users, an exercise service 3715 and associated exercise database that includes and stores information associated with analyzing user exercise and workout activities, and other health service 3720 modules.

The system 3700 also includes a base recommendation system 3730, which includes a diet analysis system 3732 and action system 3734 configured to perform various operations described herein and directed to receiving user information and determining beverage profiles to recommend to the users based on the user information. The base system 3730 may provide information to a partner's system 3735, which includes partner information, algorithm partner information 3737, and is configured to modify recommendation information to transmit to various online systems or partners using their formats, structures, and/or relevant APIs or syntaxes.

A health database 3740 stores information received by the system 3700 and/or generated by the system 3700. The health database 3700 includes a nutrition database 3742 that stores nutrition information for ingredients, profiles, available beverages, and so on, a medicine database 3744 that stores information for various medical goals or issues provided by users, and a recipe database 3746 that stores recipes for creating beverage profiles, such as profiles for smoothies to be made for users.

The system 3700 may also include components that generate reports 3750, send alerts 3752, provide various informational dashboards 3754, or otherwise provide information to users and online systems that is associated with their consumption, progress, health, and so on. The system 3700 may include billing software that handles billing and payments for use of the system 3700 by the online systems. The billing software 3756 and/or the partners system 3735 may store data in a partner's database 3760, which may also transfer data to the various health databases 3740 via APIs 3765 provided by the system 3700.

Figure 38:
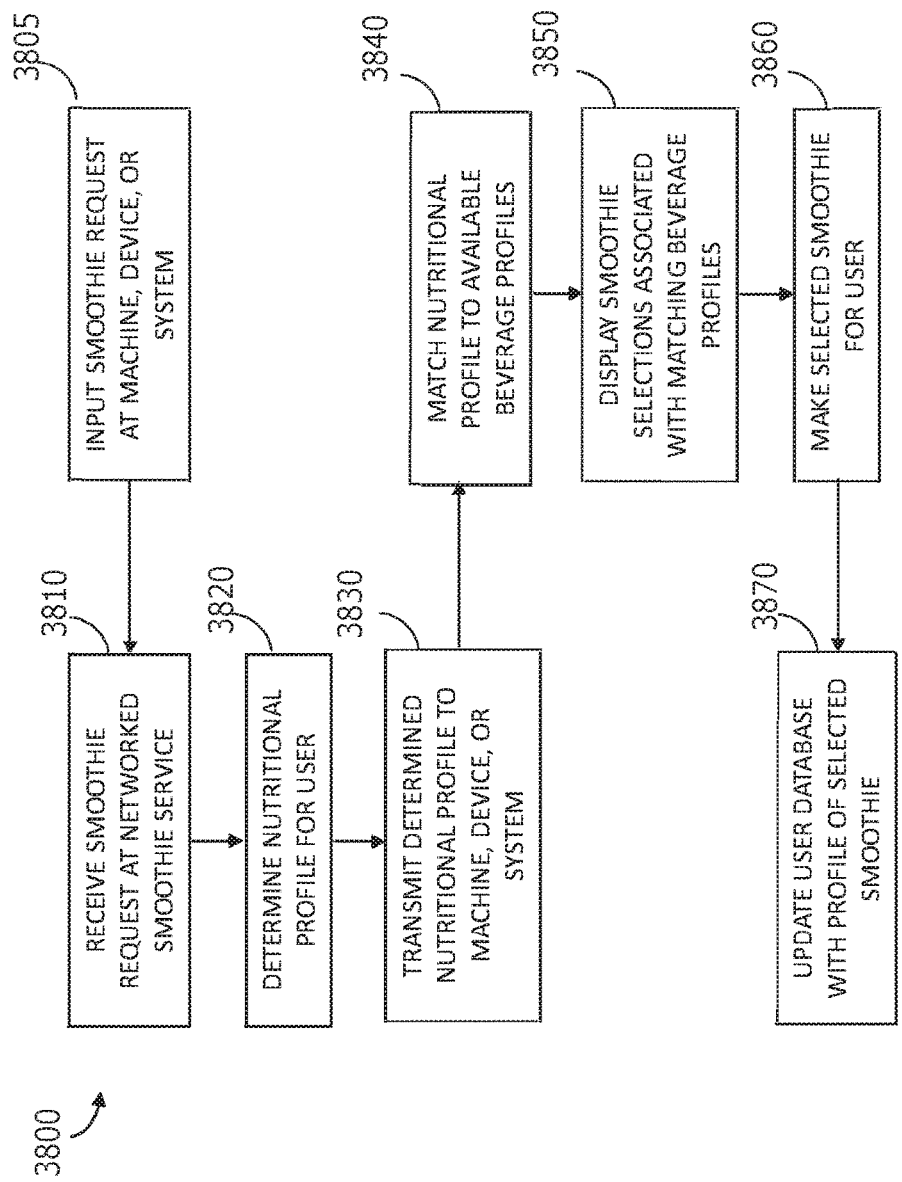
FIG. 38 is a flow diagram illustrating a method for determining a beverage recommendation for a user of an online wellness program.

As described herein, the system 3700 performs various processes, operations, or methods when determining and/or providing recommendations for beverages, such as smoothies, to online systems 2460. FIG. 38 is a flow diagram illustrating a method 3800 for determining a beverage recommendation for a user of an online wellness program. Aspects of the method 3800 may be performed by the system 3800 or various connected devices and, accordingly, is described herein merely by way of reference thereto. It will be appreciated that the method 3800 may be performed on any suitable hardware.

In operation 3805, a request for a smoothie, or other beverage, is received at a connected device, machine (beverage machine 2420), or system (restaurant device). In operation 3810, the system 3700 receives the request, along with wellness goal information and/or daily smoothie consumption data for the user.

In operation 3820, the system 3700 determines a nutritional profile for the user. For example, the system 3700 may employ one or more recommendation systems described herein to determine a nutritional profile that meets the received request and associated data for the user.

In operation 3830, the system 3700 transmits the determined nutritional profile to the requesting device, machine or system. The receiving device, machine, or system, in operation 3840, matches the received nutritional profile to beverage profiles of available beverages (e.g., beverages associated with pods contained by the device).

In operation 3850, the device, such as a smoothie making entity, displays one or more available smoothies that match the nutritional profile for user selection, and in response to a selection, makes, in operation 3860, the selected smoothie (e.g., using one or more associated pods). In operation 3870, the system 3730 receives an indication that the smoothie was made for the user, and updates various databases with the nutritional profile for the smoothie and the consumption of the smoothie by the user.

Figure 39:
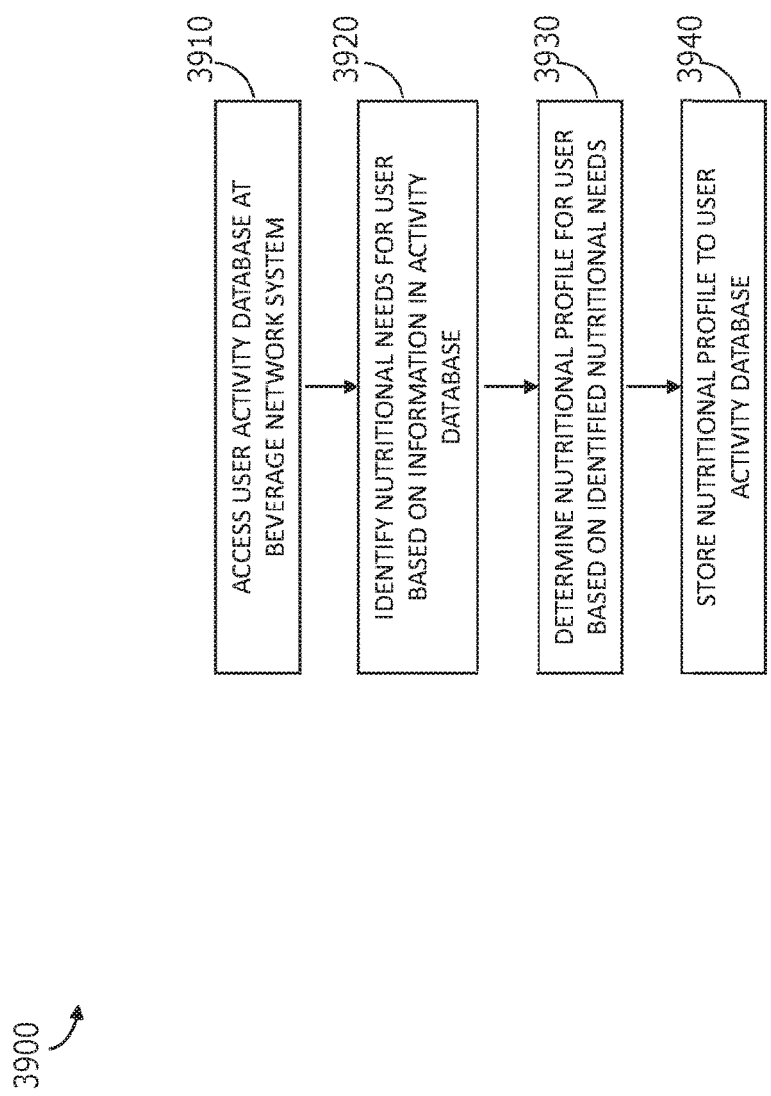
FIG. 39 is a flow diagram illustrating a method for determining a nutritional profile for a user.

FIG. 39 is a flow diagram illustrating a method 3900 for determining a nutritional profile for a user. Aspects of the method 3900 may be performed by the system 3700 or various connected devices and, accordingly, is described herein merely by way of reference thereto. It will be appreciated that the method 3900 may be performed on any suitable hardware.

In operation 3910, the system 3700 accesses a user activity database of the beverage network server 2430, and, in operation 3920, identifies nutritional needs for the user based on the information. For example, the database may store data received from one or more wearable devices 2415 and/or via one or more online systems 2460 associated with wellness programs that include the user as a member.

In operation 3930, the system 3700 determines a nutritional profile for the user based on identified nutritional needs. As described herein, the system 3700 may access health goal information or user health information to identify the nutritional needs for the user. In operation 3940, the system 3700 stores the nutritional profile to one or more health databases 3740 of the system.

Figure 40:
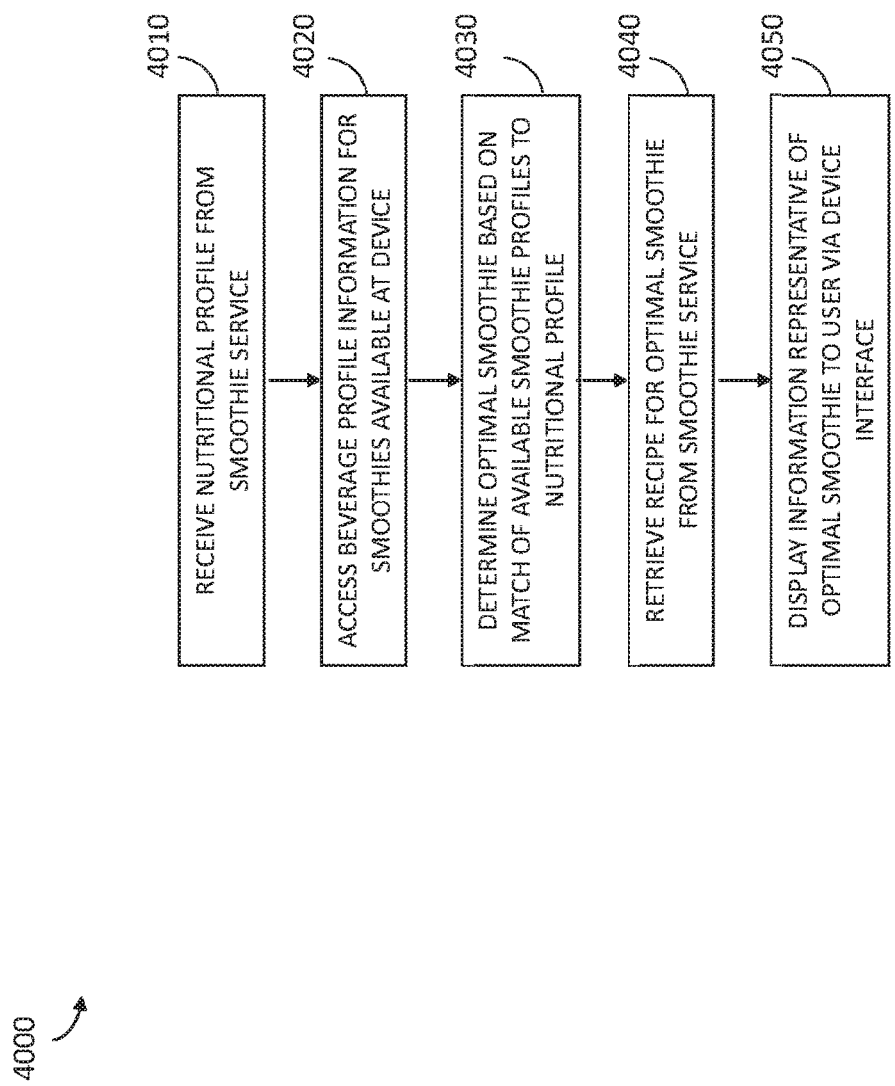
FIG. 40 is a flow diagram illustrating a method for determining a customized beverage for a user based on the user's nutritional profile.

FIG. 40 is a flow diagram illustrating a method 4000 for determining a customized beverage for a user based on the user's nutritional profile. Aspects of the method 4000 may be performed by the system 3700 or various connected devices and, accordingly, is described herein merely by way of reference thereto. It will be appreciated that the method 4000 may be performed on any suitable hardware.

In operation 4010, a smoothie making entity (e.g., a connected device or beverage machine 2420) receives a nutritional profile from the system 3700 (e.g., a "smoothie service"). In operation 4020, the entity accesses beverage profile information for smoothies available at the entity.

In operation 4030, the entity determines an optimal smoothie based on matching the profiles of the available smoothies to the received nutritional profile, and, in operation 4040, retrieves a recipe for the smoothie. Using the recipe, the entity, in operation 4050, displays information representative of the available smoothie or smoothies via an interface of the entity. Upon receiving a selection of a displayed smoothie, the entity makes the smoothie (or, orders the related smoothie pods) for the user.

Figure 41:
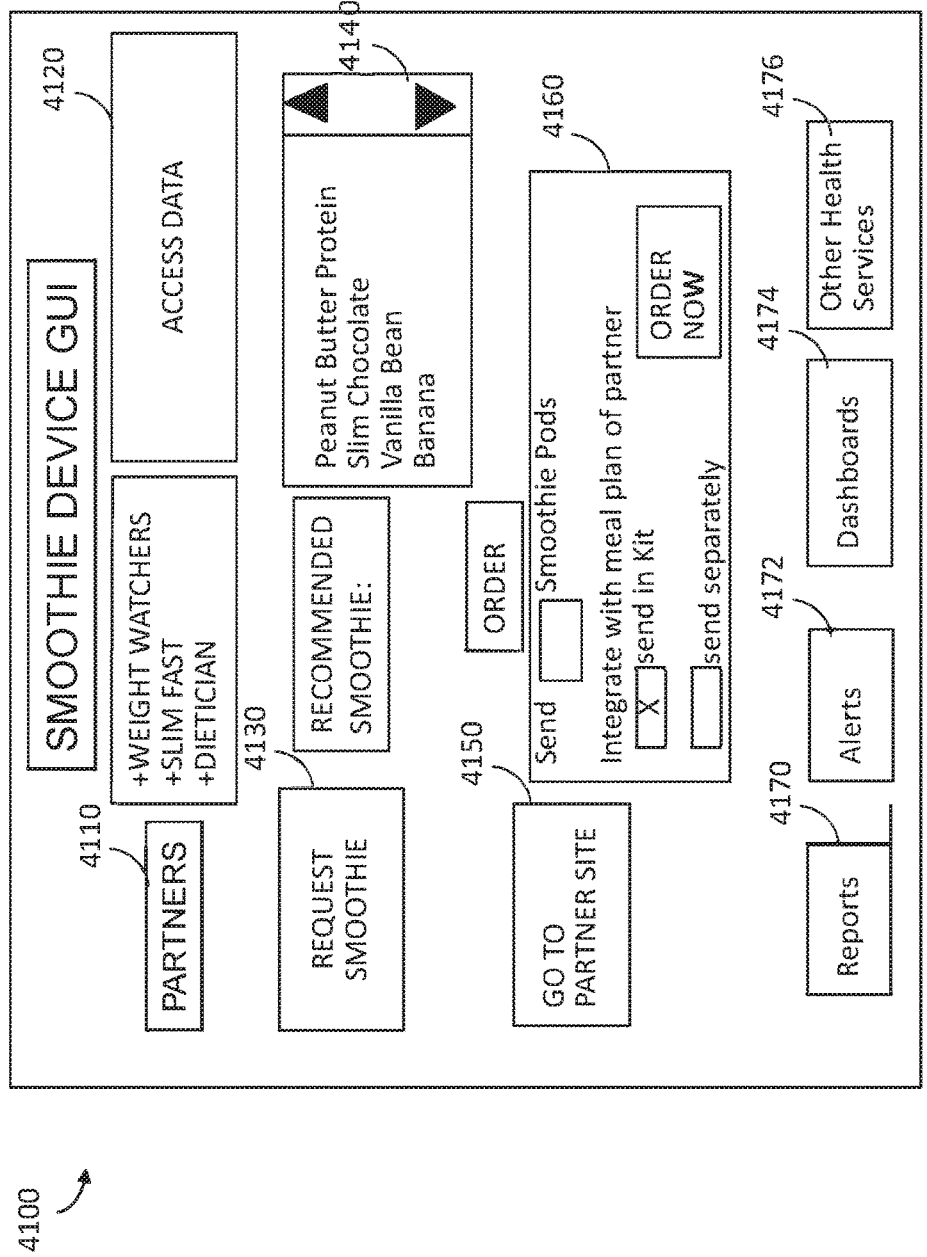
FIG. 41 is a display diagram illustrating a user interface that presents recommended beverages to a user and facilitates making and ordering of beverages on behalf of the user.

For example, FIG. 41 is a display diagram illustrating a user interface 4100 that presents recommended beverages to a user and facilitates making and ordering of beverages on behalf of the user. The user interface 4100 presents options to select a partner 4110 and access data 4120 associated with the user. The user interface also presents options to request a smoothie, and displays recommended smoothies 4140. Further displayed options include partner site navigation options 4150, options to order associated smoothie pods 4160, and other user-selectable elements associated with ordering or making recommended smoothies for the user.

Further, the interface 4100 includes user-selectable elements associated with the system 3700 generating reports 4170, sending or setting alerts 4122, presenting dashboards 4174, or performing other services 4176. Thus, the interface 4100 may facilitate the access of reports, alerts, dashboards (e.g., trends, and so on) and other health service information.

In addition, the system 3700 may provide other aspects or features, including:

Allow partner systems to disable aspects of the recommendations, such as after determining a user is over their calorie allotment for the day, preventing the user from further hurting their diet;

Receiving data from various wearable tracking devices, including: communicating previous exercise data (e.g., 3 mile run burning 380 calories) to the system, which may modify smoothie recommendations, and inform the user how the calories burned by the exercise translates to consumption, educating the user about the results of exercise (e.g., how much work it takes to burn off enough calories), or communicating calories of a recommended beverage to the fitness tracker to give the user a goal calorie amount to burn, which informs the user about how many calories their smoothie was, and that amount is set as a goal for the user during their workout session;

Facilitating connections to POS devices, so a user's food order may be automatically uploaded to a partner system, enabling immediate ordering of the user's meal choice, allowing the partner to make smoothie suggestions based on up to date information, allowing automatic logging of user choices, and so on;

Directly logging exercise data (e.g., at the gym) for a user to directly log their workout data, as well as have smart gym equipment (e.g., treadmill) send data to the system, which can then be uploaded to the partner sites. The system may also prompt the user to enter their previous meals for the day if the user hasn't done so, ensuring the partner receives updates of exercise/diet data before making a smoothie suggestion; and so on.

Thus, in some embodiments, the systems and methods receive, via an application programming interface (API), a request for a smoothie from a smoothie making entity associated with a user, determine a nutritional profile for the user that is based on a wellness goal associated with the user and daily consumption data of the user, and send the nutritional profile to the smoothie making entity, which makes a pod-based smoothie having the nutritional profile. As described herein, the smoothie making entity may be a restaurant that communicates with the API using an online ordering system, a networked smoothie making machine or device, an online diet program, and so on.

Therefore, in some embodiments, the systems and methods provide a smoothie SaaS for various smoothie making (or, smoothie pod ordering) endpoints, such as restaurants, networked machines, and so on. The endpoints receive requests from users, access the various processes provided by the SaaS, and provide users with smoothies based on recommendations or instructions received from the smoothie SaaS.

The invention claimed is:

1. A method for designing a smoothie pod, the method comprising:

receiving input from a user via a user device that communicates with a beverage profile system over a communications network, wherein the input is received via a graphical user interface and includes selections of ingredients to be added to the smoothie pod;

determining, via the beverage profile system, that a flavor profile of the smoothie pod that is based on the ingredients selected by the user includes at least one flavor type having a percentage of the flavor profile that is outside of an acceptable threshold percentage range of the flavor profile;

presenting a suggestion via the graphical user interface of one or more additional ingredients to be added to the smoothie pod to modify the percentage of the flavor type to be within the acceptable threshold percentage range of the flavor profile;

determining whether the at least one flavor type is within the acceptable threshold percentage range of the flavor profile based on a user selection of the one or more additional ingredients; and when the flavor types are determined to be within the acceptable threshold percentage range, presenting the user with the options to save the user's selection or order the smoothie pod.

2. The method of claim 1, wherein the graphical user interface is a graphical user interface of the user device.

3. The method of claim 1, wherein presenting a suggestion to modify the percentage of the flavor type to be within the acceptable threshold percentage range of the flavor profile includes presenting information that displays a modified flavor profile via the graphical user interface.

4. The method of claim 1, wherein determining that a flavor profile of the smoothie pod that is based on the ingredients selected by the user includes at least one flavor type having a percentage of the flavor profile that is outside of an acceptable threshold percentage range of the flavor profile includes determining the flavor type is associated with a percentage above a maximum percentage amount acceptable for a single flavor type of the flavor profile.

5. The method of claim 1, wherein determining that a flavor profile of the smoothie pod that is based on the ingredients selected by the user includes at least one flavor type having a percentage of the flavor profile that is outside of an acceptable threshold percentage range of the flavor profile includes determining the flavor type is associated with a percentage below a minimum percentage amount acceptable for a single flavor type of the flavor profile.

6. The method of claim 1, wherein a flavor type is a bitter flavor, sweet flavor, salty flavor, savory flavor, or sour flavor.

7. A non-transitory computer-readable medium whose contents, when executed by a beverage profile system, cause the beverage profile system to perform a method for designing a smoothie pod, the method comprising:

receiving input from a user via a user device that communicates with the beverage profile system over a communications network, wherein the input is received via a graphical user interface and includes selections of ingredients to be added to the smoothie pod;

determining, via the beverage profile system, that a flavor profile of the smoothie pod that is based on the ingredients selected by the user includes at least one flavor type having a percentage of the flavor profile that is outside of an acceptable threshold percentage range of the flavor profile;

presenting a suggestion via the graphical user interface of one or more additional ingredients to be added to the smoothie pod to modify the percentage of the flavor type to be within the acceptable threshold percentage range of the flavor profile;

determining whether the at least one flavor type is within the acceptable threshold percentage range of the flavor profile based on a user selection of the one or more additional ingredients; and when the flavor types are determined to be within the acceptable threshold percentage range, presenting the user with the options to save the user's selection or order the smoothie pod.

8. The non-transitory computer-readable medium of claim 7, wherein the graphical user interface is a graphical user interface of the user device.

9. The non-transitory computer-readable medium of claim 7, wherein presenting a suggestion to modify the percentage of the flavor type to be within the acceptable threshold percentage range of the flavor profile includes presenting information that displays a modified flavor profile via the graphical user interface.

10. The non-transitory computer-readable medium of claim 7, wherein determining that a flavor profile of the smoothie pod that is based on the ingredients selected by the user includes at least one flavor type having a percentage of the flavor profile that is outside of an acceptable threshold percentage range of the flavor profile includes determining the flavor type is associated with a percentage above a maximum percentage amount acceptable for a single flavor type of the flavor profile.

11. The non-transitory computer-readable medium of claim 7, wherein determining that a flavor profile of the smoothie pod that is based on the ingredients selected by the user includes at least one flavor type having a percentage of the flavor profile that is outside of an acceptable threshold percentage range of the flavor profile includes determining the flavor type is associated with a percentage below a minimum percentage amount acceptable for a single flavor type of the flavor profile.

12. The non-transitory computer-readable medium of claim 7, wherein a flavor type is a bitter flavor, sweet flavor, salty flavor, savory flavor, or sour flavor.

* * * * *